US008053558B2

(12) United States Patent
Pardoll et al.

(10) Patent No.: US 8,053,558 B2
(45) Date of Patent: *Nov. 8, 2011

(54) DENDRITIC CELL CO-STIMULATORY MOLECULES

(75) Inventors: Drew M. Pardoll, Brookville, MD (US);
Haruo Tsuchiya, Baltimore, MD (US);
Kevin S. Gorski, Baltimore, MD (US);
Su-Yi Tseng, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 639 days.

This patent is subject to a terminal disclaimer.

(21) Appl. No.: 11/931,653

(22) Filed: Oct. 31, 2007

(65) Prior Publication Data

US 2008/0226662 A1    Sep. 18, 2008

Related U.S. Application Data

(60) Continuation of application No. 11/361,057, filed on Feb. 24, 2006, now Pat. No. 7,560,540, which is a division of application No. 09/794,210, filed on Feb. 28, 2001, now Pat. No. 7,030,219.

(60) Provisional application No. 60/200,580, filed on Apr. 28, 2000, provisional application No. 60/240,169, filed on Oct. 13, 2000.

(51) Int. Cl.
*C07K 14/00* (2006.01)

(52) U.S. Cl. ...................................... 530/350

(58) Field of Classification Search .................. None
See application file for complete search history.

(56) References Cited

U.S. PATENT DOCUMENTS

| | | | |
|---|---|---|---|
| 4,272,398 A | 6/1981 | Jaffe |
| 4,376,110 A | 3/1983 | David et al. |
| 4,650,764 A | 3/1987 | Temin et al. |
| 4,769,330 A | 9/1988 | Paoletti et al. |
| 4,861,627 A | 8/1989 | Mathiowitz et al. |
| 4,861,719 A | 8/1989 | Miller |
| 4,925,673 A | 5/1990 | Steiner et al. |
| 4,980,289 A | 12/1990 | Temin et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,225,336 A | 7/1993 | Paoletti |
| 5,225,538 A | 7/1993 | Capon et al. |
| 5,240,846 A | 8/1993 | Collins et al. |
| 5,278,056 A | 1/1994 | Bank et al. |
| 5,284,656 A | 2/1994 | Platz et al. |
| 5,451,569 A | 9/1995 | Wong et al. |
| 5,521,288 A | 5/1996 | Linsely et al. |
| 5,567,584 A | 10/1996 | Sledziewski et al. |
| 5,675,848 A | 10/1997 | Kappel |
| 5,714,147 A | 2/1998 | Capon et al. |
| 5,750,375 A | 5/1998 | Sledziewski et al. |
| 5,843,725 A | 12/1998 | Sledziewski et al. |
| 5,861,310 A | 1/1999 | Freeman et al. |
| 5,942,607 A | 8/1999 | Freeman et al. |
| 6,018,026 A | 1/2000 | Sledziewski et al. |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,630,575 B2 | 10/2003 | Coyle et al. |
| 6,635,750 B1 * | 10/2003 | Coyle et al. .................. 536/23.5 |
| 6,743,619 B1 | 6/2004 | Tang et al. |
| 6,919,193 B2 | 7/2005 | Tang et al. |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,560,540 B2 | 7/2009 | Pardoll et al. |
| 7,563,869 B2 | 7/2009 | Honjo et al. |
| 7,595,048 B2 | 9/2009 | Honjo et al. |
| 7,709,214 B2 | 5/2010 | Freeman et al. |
| 7,723,479 B2 | 5/2010 | Mikesell et al. |

(Continued)

FOREIGN PATENT DOCUMENTS

EP    1074617 A    10/2000

(Continued)

OTHER PUBLICATIONS

Singh et al., Nature Biotechnology, 1999, 17: 1075-1081.* GenBank Accession No. AF142780, 3 pages (1999).*
Sequence alignment, 1 page (2010).*
Attwood T., Science, 2000; 290:471-473.*
Skolnick et al., Trends in Biotech. 2000; 18(1):34-39.*
Gerstmayer, et al., "Costimulation of T cell proliferation by a chimeric B7-2 antibody fusion protein specifically targeted to cells expressing the erbB2 proto-oncogene," *J. Immunol.*, 158(10): 4584-90 (1997).
Guo, et al., "A novel fusion protein of IP10-scFv retains antibody specificity and chemokine function," *Biochem. Biophys. Res. Commun.*, 320(2):506-13 (2004).
Lewinski, et al., "Retroviral DNA integration: viral and cellular determinants of target-site selection," *PLoS Pathog.*, 2(6):e60 (2006).
Lu, et al., "EGF-IL-18 fusion protein as a potential anti-tumor reagent by induction of immune response and apoptosis in cancer cells," *Cancer Lett.*, 60(1-2):187-97 (2008).

(Continued)

*Primary Examiner* — Ilia Ouspenski
(74) *Attorney, Agent, or Firm* — Pabst Patent Group LLP

(57) ABSTRACT

A novel costimulatory protein molecule, B7-DC, which is a member of the B7 family, is described as is DNA coding therefor and expression vectors comprising this DNA. B7-DC protein, fragments, fusion polypeptides/proteins and other functional derivatives, and transformed cells expressing B7-DC are useful in vaccine compositions and methods. Compositions and methods are disclosed for inducing potent T cell mediated responses that can be harnessed for anti-tumor and anti-viral immunity.

31 Claims, 8 Drawing Sheets

U.S. PATENT DOCUMENTS

| | | | |
|---|---|---|---|
| 2002/0091246 | A1 | 7/2002 | Pardoll et al. |
| 2002/0095024 | A1 | 7/2002 | Mikesell et al. |
| 2002/0106730 | A1 | 8/2002 | Coyle et al. |
| 2002/0107363 | A1 | 8/2002 | Fox et al. |
| 2002/0110836 | A1 | 8/2002 | Freeman et al. |
| 2002/0164600 | A1 | 11/2002 | Freeman et al. |
| 2003/0142359 | A1 | 7/2003 | Bean et al. |
| 2003/0171551 | A1 | 9/2003 | Rosenblatt et al. |
| 2003/0208058 | A1 | 11/2003 | Fiscella et al. |
| 2003/0232323 | A1 | 12/2003 | Freeman et al. |
| 2004/0010134 | A1 | 1/2004 | Rosen et al. |
| 2005/0228170 | A1 | 10/2005 | Fox et al. |
| 2005/0260716 | A1 | 11/2005 | Moore et al. |
| 2006/0034826 | A1 | 2/2006 | Carreno et al. |
| 2006/0084794 | A1 | 4/2006 | Rosen et al. |
| 2006/0110383 | A1 | 5/2006 | Honjo et al. |
| 2006/0223088 | A1 | 10/2006 | Rosen et al. |
| 2007/0037206 | A1 | 2/2007 | Rosen et al. |
| 2007/0041963 | A1 | 2/2007 | Rosen et al. |
| 2007/0065427 | A1 | 3/2007 | Freeman et al. |
| 2007/0092504 | A1 | 4/2007 | Carreno et al. |
| 2007/0099833 | A1 | 5/2007 | Rosen et al. |
| 2007/0122378 | A1 | 5/2007 | Freeman et al. |
| 2007/0224663 | A1 | 9/2007 | Rosen et al. |
| 2008/0025979 | A1 | 1/2008 | Honjo et al. |
| 2008/0118511 | A1 | 5/2008 | Freeman et al. |
| 2008/0241175 | A1 | 10/2008 | Pardoll et al. |
| 2009/0042292 | A1 | 2/2009 | Chen |
| 2009/0075338 | A1 | 3/2009 | Moore et al. |
| 2009/0269783 | A1 | 10/2009 | Coyle et al. |

FOREIGN PATENT DOCUMENTS

| | | | |
|---|---|---|---|
| WO | WO 90/07861 | | 7/1990 |
| WO | WO 91/10741 | | 7/1991 |
| WO | WO 91/17271 | | 11/1991 |
| WO | WO 92/00092 | | 1/1992 |
| WO | WO 92/01047 | | 1/1992 |
| WO | WO 92/20791 | | 11/1992 |
| WO | WO93/01222 | | 1/1993 |
| WO | WO 95/05464 | | 2/1995 |
| WO | WO 95/07707 | | 3/1995 |
| WO | WO 97/17613 | | 5/1997 |
| WO | WO 97/17614 | | 5/1997 |
| WO | WO 97/24447 | | 7/1997 |
| WO | WO 98/23635 | | 6/1998 |
| WO | WO 98/33914 | | 8/1998 |
| WO | WO 99/64597 | | 12/1999 |
| WO | WO 00/55375 | | 9/2000 |
| WO | WO 00/61612 | | 10/2000 |
| WO | WO 01/34629 | | 5/2001 |
| WO | WO 01/70979 | | 9/2001 |
| WO | WO 01/94413 | A2 | 12/2001 |
| WO | WO 02/00692 | A2 | 1/2002 |
| WO | WO 02/00730 | | 1/2002 |
| WO | WO 02/02587 | | 1/2002 |
| WO | WO 02/02587 | A1 | 1/2002 |
| WO | WO 02/08279 | A2 | 1/2002 |
| WO | WO 02/02891 | A2 | 3/2002 |
| WO | WO 02/24891 | | 3/2002 |
| WO | WO 02/057453 | A2 | 7/2002 |
| WO | WO 02/078731 | A1 | 10/2002 |
| WO | WO 02/079474 | A2 | 10/2002 |
| WO | WO 02/081731 | A2 | 10/2002 |
| WO | WO 03/008583 | | 1/2003 |
| WO | WO 2006/050172 | | 5/2006 |
| WO | WO 2008/037080 | | 4/2008 |
| WO | WO 2009/029342 | | 3/2009 |
| WO | WO 2009/114110 | | 9/2009 |

OTHER PUBLICATIONS

International Search Report for PCT/US01/13430 dated Feb. 20, 2002.

Tseng S. et al., "B7-DC, a new dendritic cell molecule with potent costimulatory properties for T cells," *J. Exper. Med.*, vol. 193, No. 7, (Apr. 2, 2001), pp. 839-845.

Database EM_MUS [Online] EMBL; Accession No. AF142780 (Jun. 1, 1999).

Database EM_HUM [Online] EMBL; Accession No. AK001872 (Feb. 22, 2000).

Chen L. et al., "Costimulation of Antitumor Immunity by the B7 Counterreceptor of the T Lymphocyte Molecules CD28 and CTLA-4," *Cell*, vol. 71, (Dec. 24, 1992), pp. 1093-1102.

Gerstmayer B. et al., "Costimulation of T-cell proliferation by a chimeric B7-antibody fusion protein," *Cancer Immunology Immunotherapy*, vol. 45, No. 3-4, (Nov. 1997), pp. 156-158.

Henry, J. et al., "Structure and evolution of the extended B7 family," *Immunology Today*, vol. 20, No. 6, (Jun. 1999), pp. 285-288.

Yoshinga S.K. et al., "T-cell co-stimulation through B7RP-1 and ICOS," *Nature* vol. 402, (Dec. 16, 1999) pp. 827-832.

Townsend S.E. et al, Tumor Rejection After Direct Costimulation of CD8+T Cells by B7-Transfected Melanoma Cells, *Science*, vol. 259, (Jan. 15, 1993), pp. 368-370.

H. Henry, "Structure and Evolution of the Extended by Family," vol. 20, Immunology Today, No. 6, Jun. 1999, pp. 285-288.

Gordon J. Freeman, "Cloning of B7-2: A CTLA-4 Counter-Receptor that Costimulates Human T Cell Proliferation," vol. 262, Science, No. 1993, pp. 909-911.

Gordon J. Freeman, "B7, A New Member of the Ig Superfamily With Unique Expression on Activated and Neoplastic B Cells," vol. 143, No. 8, Oct. 1989, The Journal of Immunology, pp. 2714-2722.

Ziba Razi-Wolf, "Expression and Function of the Murine B7 Antigen, The Major Costimulatory Molecule Expressed by Peritoneal Exudate Cells," vol. 89, Proc. Natl. Acad. Sci., May 1992, pp. 4210-4214.

Peter S. Linsley, "T-Cell Antigen CD28 Mediates Adhesion With B Cells by Interacting With Activation Antigen B7/BB-1," vol. 87, Proc. Natl. Acad. Sci., Jul. 1990, pp. 5031-5035.

D. Lenschow, "Expression and Functional Significance of an Additional Ligand for CTLA-4," vol. 90, Proc. Natl. Acad. Sci., Dec. 1993, pp. 11054-11058.

C. Gimmi et al., "B-Cell Surface Antigen B7 Provides a Costimulatory Signal That Induces T Cells to Proliferate and Secrete Interleukin 2," vol. 88, Proc. Natl. Acad. Sci., Aug. 1991, pp. 6575-6579.

P. Linsley et al., "Binding of the B Cells Activation Antigen B7 to CD28 Costimulates T Cell Proliferation and Interleukin 2 mRNA Accumulation," vol. 173, J. Exp. Med., Mar. 1991, pp. 721-730.

G. Freeman et al., "Structure, Expression, and T Cell Costimulatory Activity of the Murine Homologue of the Human B Lymphocyte Activation Antigen B7," vol. 174, J. Exp. Med., Sep. 1991, pp. 625-631.

G. Freeman et al., "Engagement of the PD-1 Immunoinhibitory Receptor by a Novel B7 Family Member Leads to Negative Regulation of Lymphocyte Activation," vol. 192, J. Exp. Med., No. 7, Oct. 2000, pp. 1027-1034.

J. Henry et al., "Cloning, Structural Analysis, and Mapping of the B30 and B7 Multigen Families to the Major Histocompatibility Complex (MHC) and Other Chromosomal Regions," vol. 46, Immunogenetics, 1997, pp. 383-395.

Tazi-Ahnini at al., "Cloning, Localization, and Structure of New Members of the Butyrophilin Gene Family in the Juxta-Telomeric Region of the Major Histocompatibility Complex," vol. 47, Immunogenetics, 1997, pp. 55-63.

R. Schwartz, "Costimulation of T Lymphocytes: The Role of CD28, CTLA-4, and B7/BB1 in Interluekin-2 Production and Immunotherapy," vol. 71, Cell, Dec. 1992, pp. 1065-1068.

L. Chen et al., "Costimulation of Antitumor Immunity by the B7 Counterreceptor for the T Lymphocyte Molecules CD28 and CTLA-4," vol. 71, Cell, Dec. 1992, pp. 1093-1102.

H. Dong et al., "By-H1, a Third Member of the B7 Family, Co-Stimulates T-Cell Proliferation and Interluekin-10 Secretion," vol. 5, No. 12, Nature.Medicine, Dec. 1999, pp. 13465-1369.

S. Wang et al., "Costimulation of T Cells by B7-H2, a B7-Like Molecule that Binds ICOS," vol. 96 No. 8, Immunobiology-Blood, Oct. 2000, pp. 2808-2813.

M. Swallow et al., "B7h, a Novel Costimulatory Homolog B B7.1 and B7.2, is Induced by TNF-Alpha," vol. 11, Immunity, Oct. 1999, pp. 423-432.

S. Yoshinaga, "T-Cell Co-Stimulation Through ByRP-1 and ICOS," vol. 402, Nature, Dec. 1999, pp. 827-832.

Metzler et al. Nature Structural Biol. 1997; 4:527-531.
Coyle et al. Nature Immunol. 2:203-209 2001.
Peach et al. J. Biol. Chem. 1995; 270:21181-21187.
Acsadi, et al., "Direct gene transfer and expression into rat heart in vivo", *The New Biologist*, 3:71-81 (1991).
Agata, et al., "Expression of the PD-1 antigen on the surface of stimulated mouse T and B lymphocytes", *Int. Immunol.*, 8:765-772 (1996).
Aldovini and Young, "Humoral and cell-mediated immune responses to live recombinant BCG-HIV vaccines", *Nature*, 351:479-482 (1991).
Anderson, "Human gene therapy", *Science*, 256:808-813 (1992).
Attwood, et al., "Genomics. The babel of bioinformatics", *Science*, 290(5491):471-3 (2000).
Bajorath, et al., "Molecular modeling of CD28 and three-dimensional analysis of residue conservation in the CD28/CD152 family", *J. Mol. Graph. Model.*, 15:135-139, 108-11 (1997).
Benita, et al., "Characterization of drug-loaded poly(d,l-lactide) microspheres", *J. Pharm. Sci.*, 73:1721-1724 (1984).
Berman, et al., "The Protein Data Bank", *Nucl. Acids Res.*, 28:235-242 (2000).
Bona and Hiernaux, et al., "Immune response: Idiotype anti-idiotype network", *CRC Crit. Rev. Immunol.*, 33-81 (1981).
Bonifaz, et al., "Efficient targeting of protein antigen to the dendritic cell receptor DEC-205 in the steady state leads to antigen presentation on major histocompatibility complex class I products and peripheral CD8+ T cell tolerance", *J. Exp. Med.*, 196(12):1627-38 (2002).
Bonifaz, et al., "In vivo targeting of antigens to maturing dendritic cells via the DEC-205 receptor improves T cell vaccination", *J. Exp. Med.*, 199(6):815-24 (2004).
Braquet, et al., "Effect of Endothelin-1 on Blood Pressure and Bronchopulmonary System of the Guinea Pig", *J. Cardiovascular Pharmacology*, 13(S5):S143-S146 (1989).
Chakrabarti, et al., "Vaccinia virus expression vector: coexpression of beta-galactosidase provides visual screening of recombinant virus plaques", *Molec. Cell. Biol.*, 5:3403-3409 (1985).
Chambers and Allison, Co-stimulation in T cell responses *Curr. Opin. Immunol.*, 9:396-404 (1997).
Chapoval, et al., "B7-H3: a costimulatory molecule for T cell activation and IFN-gamma production", *Nature Immunol.*, 2:269-274 (2001).
Choi, et al., "Genomic organization and expression analysis of B7-H4, an immune inhibitory molecule of the B7 family", *J. Immunol.*, 171:4650-4654 (2003).
Cone and Mulligan, "High-efficiency gene transfer into mammalian cells: generation of helper-free recombinant retrovirus with broad mammalian host range", *Proc. Natl. Acad. Sci. USA*, 81:6349-6353 (1984).
Crystal, "Gene therapy strategies for pulmonary disease" *Amer. J. Med.*, 92(suppl 6A):44S-52S (1992).
Debs, et al., "Lung-specific delivery of cytokines induces sustained pulmonary and systemic immunomodulation in rat", *J. Immunol.*, 140:3482-3488 (1988).
Dong, et al., "Immune regulation by novel costimulatory molecules", *Immunol. Res.*, 28(1):39-48 (2003).
Dunussi-Joannopoulos, et al., "Gene Therapy with B7.1 and GM-CSF Vaccines in a Murine AML Model", *J. Pediatr. Hematol. Oncol.*, 19(6):536-540 (1997).
EMBL-EBI Accession No. AF142780 (Jun. 1, 1999).
EMBL-EBI Accession No. Q9WUL5 (Nov. 1, 1999).
Falkner, et al., "pUV I: a new vaccinia virus insertion and expression vector", *Nucl. Acids Res*, 15:7192 (1987).
Fechteler, et al., "Prediction of protein three-dimensional structures in insertion and deletion regions: a procedure for searching data bases of representative protein fragments using geometric scoring criteria", *J. Mol. Biol.*, 253:114-131 (1995).
Fuerst, et al., "Transfer of the inducible lac repressor/operator system from *Escherichia coli* to a vaccinia virus expression vector", *Proc. Natl. Acad. Sci. USA*, 86:2549-2553 (1989).
Guatelli, et al., "Isothermal, in vitro amplification of nucleic acids by a multienzyme reaction modeled after retroviral replication", *Proc. Natl. Acad. Sci. USA*, 87:1874-1878 (1990).

Hatzoglou, et al., "Hepatic gene transfer in animals using retroviruses containing the promoter from the gene for phosphoenolpyruvate carboxykinase" *J. Biol. Chem.* 265:17285-93 (1990).
Hawiger, et al., "Dendritic cells induce peripheral T cell unresponsiveness under steady state conditions in vivo", *J. Exp. Med.*, 194(6):769-79 (2001).
Henikoff and Henikoff, "Amino acid substitution matrices from protein blocks", *Proc. Natl. Acad. Sci. U.S.A.*, 89:10915-10919 (1992).
Hiroishi, et al., "Interferon-alpha gene therapy in combination with CD80 transduction reduces tumorigenicity and growth of established tumor in poorly immunogenic tumor models", *Gene Ther.*, 6:1988-1994 (1999).
Hochman, et al., "An active antibody fragment (Fv) composed of the variable portions of heavy and light chains", *Biochemistry*, 12:1130-1135 (1973).
Hock and Miller, "Retrovirus-mediated transfer and expression of drug resistance genes in human haematopoietic progenitor cells", *Nature*, 320:275-77 (1986). Cited as 257.
Hoiseth and Stocker, "Aromatic-dependent *Salmonella typhimurium* are non-virulent and effective as live vaccines", *Nature*, 291, 238-239 (1981).
Hubbard, et al., "Anti-neutrophil-elastase defenses of the lower respiratory tract in alpha 1-antitrypsin deficiency directly augmented with an aerosol of alpha 1-antitrypsin", Annals of Internal Medicine, 3:206-212 (1989).
Hyrup and Nielsen, "Peptide nucleic acids (PNA): synthesis, properties and potential applications", Bioorgan. Med. Chem., 4:5-23 (1996).
Ikemizu, et al., "Structure and dimerization of a soluble form of B7-1", *Immunity*, 12:51-60 (2000).
Ikonomidis, "Delivery of a viral antigen to the class I processing and presentation pathway by Listeria monocytogenes", *J. Exp. Med.*, 180:2209-2218 (1994).
Ishida, et al., "Differential expression of PD-L1 and PD-L2, ligands for an inhibitory receptor PD-1, in the cells of lymphohematopoietic tissues" *Immunol. Lett.*, 84:57-62 (2002).
Ishida, et al., "Induced expression of PD-1, a novel member of the immunoglobulin gene superfamily, upon programmed cell death", *EMBO J.*, 11:3887-3895 (1992).
Jerne, "Towards a network theory of the immune system", *Ann. Immunol.* 125C:373-389 (1974).
Johnston, et al., "Biolistic Transformation of Animal Tissue", In Vitro *Cell. Dev. Biol.*, 27P:11-14 (1991).
Kaleko, et al., "Persistent gene expression after retroviral gene transfer into liver cells in vivo" *Human Gene Therapy*, 2:27-32 (1991).
Kaufman, et al., "A phase I trial of intra lesional RV-B7.1 vaccine in the treatment of malignant melanoma", *Hum. Gene Ther.*, 11:1065-1082 (2000).
Koehler and Milstein, "Continuous cultures of fused cells secreting antibody of predefined specificity", *Nature*, 256:495-497 (1975).
Kohn, et al., "Gene therapy for genetic diseases", Cancer Invest., 7:179-192 (1989).
Krummel and Allison, "CTLA-4 engagement inhibits IL-2 accumulation and cell cycle progression upon activation of resting T cells", J. Exp. Med., 183:2533-2540 (1996).).
Kuiper, et al., "B7.1 and cytokines. Synergy in cancer gene therapy", Adv. Exp. Med. Biol., 465:381-390 (2000).
Latchman, et al., "PD-L2 is a second ligand for PD-1 and inhibits T cell activation", *Nature Immunol.*, 2(3):261-268 (2001).
Lenshow, et al., "CD28/B7 system of T cell costimulation", *Annu. Rev. Immunol.*, 14:233-258 (1996).
Levitt, "Accurate modeling of protein conformation by automatic segment matching", *J. Mol. Biol.*, 226:507-533 (1992).
Mann, et al., "Construction of a retrovirus packaging mutant and its use to produce helper-free defective retrovirus" *Cell*, 33:153-159 (1983).
Martin, et al.,"Combination gene therapy with CD86 and the MHC class II transactivator in the control of lung tumor growth", *J. Immunol.*, 162:6663-6670 (1999).
Mathiowitz and Langer, "Polyanhydride microspheres as drug carriers. I. Hot-melt microencapsulation", *J. Controlled Release*, 5:13-22 (1987).

Mathiowitz, "Novel microcapsules for delivery systems", *Reactive Polymers*, 6:275-283 (1987).

Mathiowitz, "Polyanhydride microspheres as drug carriers. II. microencapsulation by solvent removal", *J. Appl. Polymer Sci.*, 35:755-774 (1988).

Mathiowitz, et al., "Morphology of polyanhydride microsphere delivery systems", *Scanning Microscopy*,4:329-340 (1990).

Mathiowitz, et al., "Polyanhydride microspheres. IV. Morphology and characterization of systems made by spray drying", *J. Appl. Polymer Sci.* 45:125-134 (1992).

McLachlin, et al., "Retroviral-mediated gene transfer",*Prog. Nuc. Acid Res. Molec. Biol.* 38:91-135 (1990).

Miller, "Human gene therapy comes of age", Nature, 357:455-460 (1992).

Miller, et al., "Generation of helper-free amphotropic retroviruses that transduce a dominant-acting, methotrexate-resistant dihydrofolate reductase gene", Molec. Cell. Biol., 5:431-437 (1985).

Miller, et al., "Redesign of retrovirus packaging cell lines to avoid recombination leading to helper virus production", Molec. Cell. Biol., 6:2895-2902 (1986).

Miller, et al., Gene transfer by retrovirus vectors occurs only in cells that are actively replicating at the time of infection, *Mol. Cell. Biol.*, 10:4239 (1990).

Moss, "Poxvirus expression vectors", *Curr. Top. Microbiol. Immunol.*, 158:25-38 (1992).

Moss, "Poxvirus vectors: cytoplasmic expression of transferred genes", *Curr. Opin. Genet. Dev.*, 3:86-90 (1993).

Moss, "Use of vaccinia virus as an infectious molecular cloning and expression vector", *Gene Amplif Anal* 3:201-213 (1983).

Moss, "Vaccinia virus vectors", *Biotechnology*, 20:345-362 (1992).

Moss, "Vaccinia virus: a tool for research and vaccine development", *Science* 252:1662-1667 (1991).

Nabel, et al., "Recombinant gene expression in vivo within endothelial cells of the arterial wall", *Science*, 244(4910):1342-4 (1989).

Needleman and Wunsch, "A general method applicable to the search for similarities in the amino acid sequence of two proteins", *J. Mol. Biol.*, 48:443-453 (1970).

Newmark, et al., "Preparation and properties of adducts of streptokinase and streptokinase-plasmin complex with polyethylene glycol and pluronic Polyol F38", *J. Appl. Biochem.*, 4:185-189 (1982).

Nicolau, et al., "In vivo expression of rat insulin after intravenous administration of the liposome-entrapped gene for rat insulin I", *Proc. Natl. Acad. Sci. USA*, 80:1068-72 (1983).

Nishimura, et al., "Autoimmune dilated cardiomyopathy in PD-1 receptor-deficient mice", Science, 291:319-322 (2001).

Nishimura, et al., "Development of lupus-like autoimmune diseases by disruption of the PD-1 gene encoding an ITIM motif-carrying immunoreceptor", Immunity, 11:141-151 (1999).

Nishimura, et al., "Immunological studies on PD-1 deficient mice: implication of PD-1 as a negative regulator for B cell responses", Int. Immunol., 10:1563-1572 (1998).

Ostrov and Shi, "Structure of murine CTLA-4 and its role in modulating T cell responsiveness", *Science*, 90:816-819 (2000).

Penix, et al., Two essential regulatory elements in the human interferon gamma promoter confer activation specific expression in T cells, *J. Exp. Med.* 178:1483-1496 (1993).

Piccini and Paoletti, "Vaccinia: virus, vector, vaccine", *Adv. Virus Res.*, 34:43-64 (1988).

Plueckthun and Skerra, "Expression of functional antibody Fv and Fab fragments in *Escherichia coli*", *Methods Enzymol.*, 178:497-515 (1989).

Poirier, et al., "Protective immunity evoked by oral administration of attenuated aroA *Salmonella typhimurium* expressing cloned streptococcal M protein", *J. Exp. Med.*, 168:25-32 (1988).

Ponder and Richards, "Tertiary templates for proteins. Use of packing criteria in the enumeration of allowed sequences for different structural classes", *J. Mol. Biol.*, 193:775-791 (1987).

Prasad, et al., "B7S1, a novel B7 family member that negatively regulates T cell activation", *Immunity*, 18:863-873 (2003).

Rajewesky and Takemori, "Genetics, expression, and function of idiotypes", Ann. Rev. Immunol., 1:569-607 (1983).

Rathmell and Thompson, "The central effectors of cell death in the immune system", Annu. Rev. Immunol., 17:781-828 (1999).

Rosenfeld, et al., "Adenovirus-mediated transfer of a recombinant alpha 1-antitrypsin gene to the lung epithelium in vivo", Science, 252:431-3 (1991).

Rousseaux, et al., "Optimal conditions for the preparation of proteolytic fragments from monoclonal IgG of different rat IgG subclasses", *Meth. Enzymol.*, 121:663-69 (1986).

Sadoff, "Oral *Salmonella typhimurium* vaccine expressing circumsporozoite protein protects against malaria", *Science*, 240:336-338 (1988).

Salib, et al., "Utilization of sodium alginate in drug microencapsulation", *Pharmazeutische Industrie*, 40(11A):1230-34 (1978).

Samulski, et al., "Targeted integration of adeno-associated virus (AAV) into human chromosome 19", *EMBO J.*, 10:3941-3950 (1991).

Sanni, et al., "Evolution of aminoacyl-tRNA synthetase quaternary structure and activity: *Saccharomyces cerevisiae* mitochondrial phenylalanyl-tRNA synthetase",*Proc. Natl. Acad. Sci. USA*, 88:8387-91 (1991).

Sawhney, et al., "Bioerodible hydrogels based on photopolymerized poly(ethylene glycol)-co-poly(.alpha.-hydroxy acid) diacrylate macromers", *Macromolecules*, 26:581-587 (1993).

Schafer, et al., "Induction of a cellular immune response to a foreign antigen by a recombinant Listeria monocytogenes vaccine", *J. Immunol.*, 149:53-59 (1992).

Schwartz, et al., "Structural basis for co-stimulation by the human CTLA-4/B7-2 complex", *Nature*, 410:604-608 (2001).

Schwartz, et al., "Structural mechanisms of costimulation", Nature Immunol., 3:427-434 (2002).

Sharon and Givol, "Preparation of Fv fragment from the mouse myeloma XRPC-25 immunoglobulin possessing anti-dinitrophenyl activity", Biochemistry, 15:1591-1594 (1976).

Shin, et al., "Cooperative B-7-1/2 (CD80/CD86) and B7-DC costimulation of CD4+ T cells independent of the PD-1 receptor", J. Exp. Med., 198(1):31-38 (2003).

Sica, et al., "B7-H4, a molecule of the B7 family, negatively regulates T cell immunity", *Immunity*, 18:849-861 (2003).

Skerra and Plueckthun, "Assembly of a functional immunoglobulin Fv fragment in *Escherichia coli*", *Science*, 240: 1038-1041 (1988).

Skolnick, et al., "From genes to protein structure and function: novel applications of computational approaches in the genomic era", *Trends in Biotechnology*, 18(1):34-39 (2000).

Smith, et al., "Pulmonary deposition and clearance of aerosolized alpha-1-proteinase inhibitor administered to dogs and to sheep", *J. Clin. Invest.*, 84:1145-1146 (1989).

Sorge, et al., "Amphotropic retrovirus vector system for human cell gene transfer", *Molec. Cell. Biol.*, 4:1730-1737 (1984).

Soriano, et al., "Targeted and nontargeted liposomes for in vivo transfer to rat liver cells of a plasmid containing the preproinsulin I gene", *Proc. Natl. Acad. Sci. USA*, 80:7128-7131 (1983).

Stamper, et al., "Crystal structure of the B7-1/CTLA-4 complex that inhibits human immune responses", *Nature*, 410:608-611 (2001).

Summerton and Weller, "Morpholino antisense oligomers: design, preparation, and properties", *Antisense Nucleic Acid Drug Dev.* 7:187-195 (1997).

Sutter and Moss, "Nonreplicating vaccinia vector efficiently expresses recombinant genes", *Proc. Natl. Acad. Sci. USA*, 89:10847-10851 (1992).

Tamura, "B7-H1 costimulation preferentially enhances CD28-independent T-helper cell function", Blood, 97:1809-1816 (2001).

Temin, "Safety Considerations in Somatic Gene Therapy of Human Disease with Retrovirus Vectors", Human Gene Therapy, 1:111-23 (1990).

Thompson, et al., "cis-acting sequences required for inducible interleukin-2 enhancer function bind a novel Ets-related protein, Elf-1" Mol. Cell. Biol. 12:1043-1053 (1992).

Titomirov, et al., "In vivo electroporation and stable transformation of skin cells of newborn mice by plasmid DNA", Biochim. Biophys. Acta., 1088:131-134 (1991).

Todd, et al., "Transcription of the interleukin 4 gene is regulated by multiple promoter elements", *J. Exp. Med.* 177:1663-1674 1993).

Wahl, et al., "Improved radioimaging and tumor localization with monoclonal F(ab')2", *J. Nuc. Med.*, 24:316-325 (1983).

Walunas, et al., "CTLA-4 ligation blocks CD28-dependent T cell activation", *J. Exp. Med.*, 183:2541-2550 (1996).

Wang, "pH-sensitive immunoliposomes mediate target-cell-specific delivery and controlled expression of a foreign gene in mouse", *Proc. Natl. Acad. Sci. USA*, 84:7851 (1987).

Wang, et al., "Ligand binding sites of inducible costimulator and high avidity mutants with improved function", *J. Exp. Med.*, 195:1033-1041 (2002).

Wang, et al., "Molecular modeling and functional mapping of B7-H1 and B7-DC uncouple costimulatory function from PD-1 interaction", *J. Exp. Med.*, 197(9):1083-91 (2003). Epub Apr. 28, 2003.

Weiss, "Hot prospect for new gene amplifier", Science 254:1292-1293 (1991).

Williams and Barclay, "The immunoglobulin superfamily—domains for cell surface recognition", Annu. Rev. Immunol., 6:381-405 (1988).

Williams, et al., "Introduction of foreign genes into tissues of living mice by DNA-coated microprojectiles", Proc. Natl. Acad. Sci. USA, 88:2726 (1991).

Winter and Milstein, "Man-made antibodies.", Nature, 349:293-299 (1991).

Wolff, "Direct gene transfer into mouse muscle in vivo", *Science*, 247:1465-1468 (1990).

Wong, et al., "Human GM-CSF: molecular cloning of the complementary DNA and purification of the natural and recombinant proteins", *Science*, 228:810-815 (1985).

Wu and Wu, "Receptor-mediated gene delivery and expression in vivo", *J. Biol. Chem.*, 263:14621-14624 (1988).

Wu, et al., "Targeting genes: delivery and persistent expression of a foreign gene driven by mammalian regulatory elements in vivo", *J. Biol. Chem.*, 264:16985-16987 (1989).

Yang, "Gene transfer into mammalian somatic cells in vivo", *Crit. Rev. Biotechnol.*, 12:335-356 (1992).

Yang, et al., "In vivo and in vitro gene transfer to mammalian somatic cells by particle bombardment", *Proc. Natl. Acad. Sci. USA*, 87:9568-72 (1990).

Zang, et al., "B7x: a widely expressed B7 family member that inhibits T cell activation", *Proc. Natl. Acad. Sci. U.S.A.*, 100:10388-10392 (2003).

Zelenin, et al., "Genetic transformation of mouse cultured cells with the help of high-velocity mechanical DNA injection", *FEBS Lett.*, 244:65-7 (1989).

Zelenin, et al., "High-velocity mechanical DNA transfer of the chloramphenicolacetyl transferase gene into rodent liver, kidney and mammary gland cells in organ explants and in vivo", *FEBS Lett.*, 280:94-6 (1991).

Zwiebel, et al., "Drug delivery by genetically engineered cell implants", *Ann. N.Y. Acad. Sci.*, 618:394-404 (1991).

U.S. Appl. No. 11/932,471, filed Oct. 31, 2007, Chen.

European Examination Report for Bristol-Myers Squibb Co., App. No. 07 023 993.4-1521, Dated May 19, 2010.

GenBank Accession No. AK001872.1, "*Homo sapiens* cDNA FLJ11010 fis, clone PLACE1003145", pp. 1-2, (submitted Feb. 16, 2000).

GenBank Accession No. AL162253, "Human DNA sequence from clone RP11-574F11 on chromosome 9 Contains the gene for B7-H1 protein (PD-L1); the gene for programmed-death ligand 2 (PDL2) (PDCD1L2) and a novel gene", pp. 1-36 (Mar. 24, 2000).

Goodwin, et al., "Molecular Cloning and Expression of the Type 1 and Type 2 Murine Receptors for the Tumor Necrosis Factor", *Mol. and Cell. Biol.*, 11(6):3020-3026 (1991).

Linsley, et al., "Extending the B7 (CD80) gene family", *Protein Sci.*, 3(8):1341-1343 (1994).

Nechiporuk, et al., "The mouse SCA2 gene: cDNA sequence, alternative splicing and protein expression", *Human Mol Gen.*, 7(8):1301-1309 (1998).

Renauld, et al., "Expression cloning of the murine and human interleukin 9 receptor cDNAs", *Proc. Natl. Acad. Sci. USA*, 89:5690-5694 (1992).

Stammers, et al., "BTL-11: A polymorphic locus with homology to the butyrolphilin gene family, located at the border of the major histocompatibility complex class II and class III regions in human and mouse", *Immunogenetics*, 51(4-5):373-382 (2000).

Office Action in U.S. Appl. No. 11/932,327 mailed May 12, 2011.

* cited by examiner

SEQUENCE LISTING

```
<160> NUMBER OF SEQ ID NOS: 16

<210> SEQ ID NO 1
<211> LENGTH: 819
<212> TYPE: DNA
<213> ORGANISM: Homo sapiens
<220> FEATURE:
<221> NAME/KEY: CDS
<222> LOCATION: (1)..(819)
<223> OTHER INFORMATION:

<400> SEQUENCE: 1 atg atc ttc ctc ctg cta atg ttg agc ctg gaa ttg cag ctt cac cag      48
Met Ile Phe Leu Leu Leu Met Leu Ser Leu Glu Leu Gln Leu His Gln
1               5                   10                  15 ata gca gct tta ttc aca gtg aca gtc cct aag gaa ctg tac ata ata      96
Ile Ala Ala Leu Phe Thr Val Thr Val Pro Lys Glu Leu Tyr Ile Ile
            20                  25                  30 gag cat ggc agc aat gtg acc ctg gaa tgc aac ttt gac act gga agt      144
Glu His Gly Ser Asn Val Thr Leu Glu Cys Asn Phe Asp Thr Gly Ser
        35                  40                  45 cat gtg aac ctt gga gca ata aca gcc agt ttg caa aag gtg gaa aat      192
His Val Asn Leu Gly Ala Ile Thr Ala Ser Leu Gln Lys Val Glu Asn
```

```
           50                  55                  60
gat aca tcc cca cac cgt gaa aga gcc act ttg ctg gag gag cag ctg      240
Asp Thr Ser Pro His Arg Glu Arg Ala Thr Leu Leu Glu Glu Gln Leu
 65                  70                  75                  80 ccc cta ggg aag gcc tcg ttc cac ata cct caa gtc caa gtg agg gac      288
Pro Leu Gly Lys Ala Ser Phe His Ile Pro Gln Val Gln Val Arg Asp
                 85                  90                  95 gaa gga cag tac caa tgc ata atc atc tat ggg gtc gcc tgg gac tac      336
Glu Gly Gln Tyr Gln Cys Ile Ile Ile Tyr Gly Val Ala Trp Asp Tyr
            100                 105                 110 aag tac ctg act ctg aaa gtc aaa gct tcc tac agg aaa ata aac act      384
Lys Tyr Leu Thr Leu Lys Val Lys Ala Ser Tyr Arg Lys Ile Asn Thr
        115                 120                 125 cac atc cta aag gtt cca gaa aca gat gag gta gag ctc acc tgc cag      432
His Ile Leu Lys Val Pro Glu Thr Asp Glu Val Glu Leu Thr Cys Gln
    130                 135                 140 gct aca ggt tat cct ctg gca gaa gta tcc tgg cca aac gtc agc gtt      480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc      528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt      576
Thr Ser Val Leu Arg Leu Lys Pro Pro Pro Gly Arg Asn Phe Ser Cys
            180                 185                 190 gtg ttc tgg aat act cac gtg agg gaa ctt act ttg gcc agc att gac      624
Val Phe Trp Asn Thr His Val Arg Glu Leu Thr Leu Ala Ser Ile Asp
        195                 200                 205 ctt caa agt cag atg gaa ccc agg acc cat cca act tgg ctg ctt cac      672
Leu Gln Ser Gln Met Glu Pro Arg Thr His Pro Thr Trp Leu Leu His
    210                 215                 220 att ttc atc ccc tcc tgc atc att gct ttc att ttc ata gcc aca gtg      720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac      768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct      816
Thr Thr Lys Arg Pro Val Thr Thr Thr Lys Arg Glu Val Asn Ser Ala
            260                 265                 270 atc                                                                  819
Ile

<210> SEQ ID NO 2
<211> LENGTH: 273
<212> TYPE: PRT
<213> ORGANISM: Homo sapiens

<400> SEQUENCE: 2

Met Ile Phe Leu Leu Leu Met Leu Ser Leu Glu Leu Gln Leu His Gln
  1               5                  10                  15

Ile Ala Ala Leu Phe Thr Val Thr Val Pro Lys Glu Leu Tyr Ile Ile
                 20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
 65                  70                  75                  80
```

-continued

```
Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 3
<211> LENGTH: 1655
<212> TYPE: DNA
<213> ORGANISM: Murinae gen. sp.
<220> FEATURE:
<221> NAME/KEY: CDS
<222> LOCATION: (210)..(953)
<223> OTHER INFORMATION:

<400> SEQUENCE: 3

```
gaattcggca cgaggtcaaa tgtggcatat ctttgttgtc tccttctgtc tcccaactag     60
agagaacaca cttacggctc ctgtcccggg caggtttggt gtcggtgtg attggcttcc    120 agggaacctg atacaaggag caactgtgtg ctgccttttc tgtgtctttg cttgaggagc    180
tgtgctgggt gctgatattg acacagacc atg ctg ctc ctg ctg ccg ata ctg     233
                                 Met Leu Leu Leu Leu Pro Ile Leu
                                  1               5 aac ctg agc tta caa ctt cat cct gta gca gct tta ttc acc gtg aca     281
Asn Leu Ser Leu Gln Leu His Pro Val Ala Ala Leu Phe Thr Val Thr
     10                  15                  20 gcc cct aaa gaa gtg tac acc gta gac gtc ggc agc agt gtg agc ctg     329
Ala Pro Lys Glu Val Tyr Thr Val Asp Val Gly Ser Ser Val Ser Leu
25                  30                  35                  40 gag tgc gat ttt gac cgc aga gaa tgc act gaa ctg gaa ggg ata aga     377
Glu Cys Asp Phe Asp Arg Arg Glu Cys Thr Glu Leu Glu Gly Ile Arg
                45                  50                  55 gcc agt ttg cag aag gta gaa aat gat acg tct ctg caa agt gaa aga     425
Ala Ser Leu Gln Lys Val Glu Asn Asp Thr Ser Leu Gln Ser Glu Arg
            60                  65                  70 gcc acc ctg ctg gag gag cag ctg ccc ctg gga aag gct ttg ttc cac     473
Ala Thr Leu Leu Glu Glu Gln Leu Pro Leu Gly Lys Ala Leu Phe His
        75                  80                  85
```

| | | | | | | | | | | | | | | | |
|---|---|---|---|---|---|---|---|---|---|---|---|---|---|---|---|
|atc|cct|agt|gtc|caa|gtg|aga|gat|tcc|ggg|cag|tac|cgt|tgc|ctg|gtc|
|Ile|Pro|Ser|Val|Gln|Val|Arg|Asp|Ser|Gly|Gln|Tyr|Arg|Cys|Leu|Val|
| |90| | | |95| | | |100| | | | | | |

521 atc tgc ggg gcc gcc tgg gac tac aag tac ctg acg gtg aaa gtc aaa  569
Ile Cys Gly Ala Ala Trp Asp Tyr Lys Tyr Leu Thr Val Lys Val Lys
105             110                 115                 120 gct tct tac atg agg ata gac act agg atc ctg gag gtt cca ggt aca  617
Ala Ser Tyr Met Arg Ile Asp Thr Arg Ile Leu Glu Val Pro Gly Thr
            125                 130                 135 ggg gag gtg cag ctt acc tgc cag gct aga ggt tat ccc cta gca gaa  665
Gly Glu Val Gln Leu Thr Cys Gln Ala Arg Gly Tyr Pro Leu Ala Glu
        140                 145                 150 gtg tcc tgg caa aat gtc agt gtt cct gcc aac acc agc cac atc agg  713
Val Ser Trp Gln Asn Val Ser Val Pro Ala Asn Thr Ser His Ile Arg
    155                 160                 165 acc ccc gaa ggc ctc tac cag gtc acc agt gtt ctg cgc ctc aag cct  761
Thr Pro Glu Gly Leu Tyr Gln Val Thr Ser Val Leu Arg Leu Lys Pro
170                 175                 180 cag cct agc aga aac ttc agc tgc atg ttc tgg aat gct cac atg aag  809
Gln Pro Ser Arg Asn Phe Ser Cys Met Phe Trp Asn Ala His Met Lys
185                 190                 195                 200 gag ctg act tca gcc atc att gac cct ctg agt cgg atg gaa ccc aaa  857
Glu Leu Thr Ser Ala Ile Ile Asp Pro Leu Ser Arg Met Glu Pro Lys
            205                 210                 215 gtc ccc aga acg tgg cca ctt cat gtt ttc atc ccg gcc tgc acc atc  905
Val Pro Arg Thr Trp Pro Leu His Val Phe Ile Pro Ala Cys Thr Ile
        220                 225                 230 gct ttg atc ttc ctg gcc ata gtg ata atc cag aga aag agg atc tag  953
Ala Leu Ile Phe Leu Ala Ile Val Ile Ile Gln Arg Lys Arg Ile
    235                 240                 245 gggaagctgt attacggaag aagtggtctc ttcttcccag atctggacct gcggtcttgg   1013
gagttggaag gatctgatgg gaaaccctca agagacttct ggactcaaag tgagaatctt   1073
gcaggacctg ccatttgcac ttttgaaccc tttggacggt gacccagggc tccgaagagg   1133
agcttgtaag actgacaatc ttccctctgt ctcaagactc tctgaacagc aagaccccaa   1193 tggcactttta gacttacccc tgggatcctg accccagtg agggcctaag gctcctaatg   1253
actttcaggg tgagaacaaa aggaattgct ctccgcccca cccccacctc ctgctttccg   1313
cagggagaca tggaaattcc cagttactaa aatagattgt caatagagtt atttatagcc   1373
ctcatttcct ccggggactt ggaagcttca gacagggttt ttcataaaca aagtcataac   1433
tgatgtgttt tacagcatcc tagaatcctg gcagcctctg aagttctaat taactggaag   1493
catttaagca acacgtcaag tgcccctgct gtggtatttg tttctacttt tctgttttta   1553
aagtgtgagt cacaaggtaa ttgttgtaac ctgtgatatc actgtttctt gtgtctcttc   1613
tttcaactac atctttaaa acaaaaaaaa aaaaaaaaa aa                      1655

<210> SEQ ID NO 4
<211> LENGTH: 247
<212> TYPE: PRT
<213> ORGANISM: Murinae gen. sp.

<400> SEQUENCE: 4

Met Leu Leu Leu Leu Pro Ile Leu Asn Leu Ser Leu Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
        35                  40                  45

```
Cys Thr Glu Leu Glu Gly Ile Arg Ala Ser Leu Gln Lys Val Glu Asn
     50                  55                  60

Asp Thr Ser Leu Gln Ser Glu Arg Ala Thr Leu Leu Glu Glu Gln Leu
 65                  70                  75                  80

Pro Leu Gly Lys Ala Leu Phe His Ile Pro Ser Val Gln Val Arg Asp
                 85                  90                  95

Ser Gly Gln Tyr Arg Cys Leu Val Ile Cys Gly Ala Ala Trp Asp Tyr
             100                 105                 110

Lys Tyr Leu Thr Val Lys Val Lys Ala Ser Tyr Met Arg Ile Asp Thr
             115                 120                 125

Arg Ile Leu Glu Val Pro Gly Thr Gly Glu Val Gln Leu Thr Cys Gln
130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190

Met Phe Trp Asn Ala His Met Lys Glu Leu Thr Ser Ala Ile Ile Asp
            195                 200                 205

Pro Leu Ser Arg Met Glu Pro Lys Val Pro Arg Thr Trp Pro Leu His
210                 215                 220

Val Phe Ile Pro Ala Cys Thr Ile Ala Leu Ile Phe Leu Ala Ile Val
225                 230                 235                 240

Ile Ile Gln Arg Lys Arg Ile
                245

<210> SEQ ID NO 5
<211> LENGTH: 744
<212> TYPE: DNA
<213> ORGANISM: Murinae gen. sp.

<400> SEQUENCE: 5
atgctgctcc tgctgccgat actgaacctg agcttacaac ttcatcctgt agcagcttta      60
ttcaccgtga cagcccctaa agaagtgtac accgtagacg tcggcagcag tgtgagcctg     120
gagtgcgatt ttgaccgcag agaatgcact gaactggaag ggataagagc cagtttgcag     180
aaggtagaaa atgatacgtc tctgcaaagt gaaagagcca ccctgctgga ggagcagctg     240
cccctgggaa aggctttgtt ccacatccct agtgtccaag tgagagattc cgggcagtac     300
cgttgcctgg tcatctgcgg ggccgcctgg gactacaagt acctgacggt gaaagtcaaa     360
gcttcttaca tgaggataga cactaggatc ctggaggttc caggtacagg ggaggtgcag     420
cttacctgcc aggctagagg ttatccccta gcagaagtgt cctggcaaaa tgtcagtgtt     480
cctgccaaca ccagccacat caggaccccc gaaggcctct accaggtcac cagtgttctg     540
cgcctcaagc tcagcctag cagaaacttc agctgcatgt tctggaatgc tcacatgaag     600
gagctgactt cagccatcat tgaccctctg agtcggatgg aacccaaagt ccccagaacg     660
tggccacttc atgtttttcat cccggcctgc accatcgctt tgatcttcct ggccatagtg     720
ataatccaga gaaagaggat ctag                                           744

<210> SEQ ID NO 6
<211> LENGTH: 26
<212> TYPE: DNA
<213> ORGANISM: Artificial Sequence
<220> FEATURE:
```

-continued

<223> OTHER INFORMATION: primer

<400> SEQUENCE: 6
ggagctactg catgttgatt gttttg                                              26

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
tgcaaactga ggcactgaaa agtc                                                24

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ttgttgtctc cttctgtctc ccaac                                               25

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
acagttgctc cttgtatcag gttc                                                24

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gtaacggccg ccagtgtgct g                                                   21

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
cgccagtgtg atggatatct gca                                                 23

<210> SEQ ID NO 12
<211> LENGTH: 11
<212> TYPE: PRT
<213> ORGANISM: Murinae gen. sp.

<400> SEQUENCE: 12

Ser Phe Glu Arg Phe Glu Ile Phe Pro Lys Glu
1               5                   10

<210> SEQ ID NO 13
<211> LENGTH: 9

```
<212> TYPE: PRT
<213> ORGANISM: Unknown
<220> FEATURE:
<223> OTHER INFORMATION: binding sequence
<220> FEATURE:
<221> NAME/KEY: misc_feature
<222> LOCATION: (4)..(6)
<223> OTHER INFORMATION: Xaa at positions 4-6 can be any amino acid

<400> SEQUENCE: 13

Ser Gln Asp Xaa Xaa Xaa Glu Leu Tyr
1               5

<210> SEQ ID NO 14
<211> LENGTH: 8
<212> TYPE: PRT
<213> ORGANISM: Unknown
<220> FEATURE:
<223> OTHER INFORMATION: binding sequence
<220> FEATURE:
<221> NAME/KEY: misc_feature
<222> LOCATION: (1)..(3)
<223> OTHER INFORMATION: Xaa at positions 1-3 can be any amino acid
<220> FEATURE:
<221> NAME/KEY: misc_feature
<222> LOCATION: (5)..(6)
<223> OTHER INFORMATION: Xaa at positions 5-6 can be any amino acid

<400> SEQUENCE: 14

Xaa Xaa Xaa Tyr Xaa Xaa Arg Thr
1               5

<210> SEQ ID NO 15
<211> LENGTH: 10
<212> TYPE: PRT
<213> ORGANISM: Murinae gen. sp.

<400> SEQUENCE: 15

Phe Glu Arg Phe Glu Ile Phe Pro Lys Glu
1               5                   10

<210> SEQ ID NO 16
<211> LENGTH: 290
<212> TYPE: PRT
<213> ORGANISM: Murinae gen. sp.

<400> SEQUENCE: 16

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140
```

```
-continued

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
                180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
        210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
                260                 265                 270

Gly Val Glu Asp Thr Ser Ser Lys Asn Arg Asn Asp Thr Gln Phe Glu
            275                 280                 285

Glu Thr
290
```

DENDRITIC CELL CO-STIMULATORY MOLECULES

CROSS-REFERENCED TO RELATED APPLICATION

This application is a continuation of pending prior application Ser. No. 11/361,057 filed Feb. 24, 2006, now U.S. Pat. No. 7,560,540 which is a divisional of U.S. Ser. No. 09/794,210 filed Feb. 28, 2001, now U.S. Pat. No. 7,030,219, which claims priority to U.S. Ser. No. 60/200,580 filed Apr. 28, 2000, and U.S. Ser. No. 60/240,169 filed Oct. 13, 2000.

STATEMENT OF RIGHTS TO INVENTIONS MADE UNDER FEDERALLY SPONSORED RESEARCH

This invention was funded in part by grants from National Institutes of Health, which provides to the United States government certain rights in this invention.

BACKGROUND OF THE INVENTION

1. Field of the Invention

The invention in the field of biochemistry and medicine relates to novel proteins that are selectively expressed on the surface of dendritic cells and can be used as cell surface molecules or in soluble form in vaccine compositions to stimulate immune responses.

2. Description of the Background Art

The generation of a T lymphocyte response is a complex process involving cell-cell interactions and production of soluble mediators (cytokines or lymphokines). This response is regulated by several T-cell surface molecules acting as "receptors," including the T-cell receptor (TCR) complex and other "accessory" surface molecules many of which are cell surface "differentiation antigens" that were first defined by monoclonal antibodies ("CD molecules")

Optimal activation of all lymphocytes is believed to require two signals: an antigen specific or clonal signal, as well as a second, antigen non-specific signal (Janeway, C., *Cold Spring Harbor Symp. Quant Biol.* 54:1-14 (1989)). If a lymphocyte encounters an antigen alone, without co-stimulation by so-called co-stimulatory molecules (such as B7 described below), it will respond with either clonal inactivation also called "anergy" (Schwartz, R. *Science* 248:1349 (1990)) or apoptosis programmed cell death); if the co-stimulatory signal is provided it will respond with conal expansion specific for the stimulating antigen. No significant amplification of an immune response against a given antigen occurs without co-stimulation (June et al. (*Immunology Today* 15:321-331, 1994); Chen et al. (*Immunology Today* 14:483-486); Townsend, S E and Allison, J P (1993) *Science* 259:368-370).

The quality and potency of an immune response depends in large part on the type of antigen presenting cells (APC) that process and present the antigen to T cells. The density of the peptide antigen/MHC ligand available for engagement of the TCR and the provision of soluble and/or membrane-bound co-stimulatory signals by APCs at the time of T cell engagement and activation is critical. It is for these reasons that immunotherapeutic strategies have begun to focus on providing (a) the target antigen to the appropriate APC types and (b) appropriate co-stimulatory molecules to enhance T cell activation.

APCs that provide the signals required for activation of T cells include monocytes/macrophages, B lymphocytes, and, most importantly dendritic cells (DCs). In the past, activated macrophages were believed to be the critical APCs that initiated T cell responses in vivo. This notion was based on their ability to phagocytose antigens effectively and process them for surface display and presentation. More recently, attention has shifted to DC as the major initiator in vivo of antigen-specific T cell responses. DCs have a distinct phenotype from activated macrophages and are classified into different subtypes capable of initiating distinct immune responses. A functional hallmark of DCs is their approximately 100-fold greater potency then macrophages to activate naïve T cells in vitro. To date, the explanation of this potency has been based on quantitative differences in molecules known to be important for antigen presentation. The present invention is based on the discovery of an important qualitative difference.

The first signal in antigen presentation is initiated by interaction of the TCR with antigen presented in the context of class II major histocompatibility complex (MHC) molecules on the APC (Allen, *Immunol. Today* 8:270 (1987)). Co-stimulatory signals come from other molecules, the best characterized of which is the B7 family (namely B7.1, B7.2, and possibly B7.3) which are also present on APCs Two proteins expressed on the surface of T cells are the best-characterized ligands or counter-receptors for co-stimulatory molecules such as B7. CD28 is a homodimeric glycoprotein of the immunoglobulin (Ig) superfamily (Aruffo and Seed, *Proc. Natl. Acad. Sci.* 84:8573-8577 (1987)) found on most mature human T cells that functions in T cell activation. CD28, is constitutively expressed on resting T cells and increases after activation. After signaling through the T cell receptor, ligation of CD28 induces T cells to proliferate and secrete IL-2 (Linsley, P S, et al. (1991) *J. Exp. Med.* 173, 721-730; Gimmi, C D, et al. (1991) *Proc. Natl. Acad. Sci. USA.* 88, 6575-6579; Thompson, C. B., et al. (1989) *Proc. Natl. Acad. Sci. USA.* 86, 1333-1337; June, C. H., et al. (1990) *Immunol. Today.* 11, 211-6; Harding, F. A., et al. (1992) *Nature.* 356, 607-609.). CD28 mediates cell-cell contact ("intercellular adhesion"), a form of antigen-independent intercellular interaction that is essential for immune responses (Springer et al., *Ann. Rev. Immunol.* 5:223-252 (1987)).

CTLA4 is a T cell surface molecule highly homologous to CD28 but is not expressed on resting T cells and appears following T cell activation (Brunet, J. F., et al., (1987) *Nature* 328, 267-270). CTLA-4 was originally identified by differential screening of a murine cytolytic T cell cDNA library, Brunet et al., supra. The role of CTLA-4 as a second receptor for 87 is discussed in Linsley et al. (1991) *J. Exp. Med.* 174:561-569, which also noted that B7 has a higher affinity for CTLA4 than for CD28. Freeman et al. (1993) *Science* 262:907-909 discussed CTLA-4 in 87 deficient mice. Ligands for CTLA-4 are described in Lenschow et al. (1993) *Proc. Nat'l. Acad. Sci.* 90:11054-11058.

Th cells secrete growth and differentiation-inducing cytokines such as IL-2, IL-4 and IL-6 possibly in a focused manner in the area of Th-B cell contact which serves to ensure activation of only B cells presenting antigen to Th cells and avoid activation of bystander B cells.

CD28 and CTLA-4 interact with a co-stimulatory molecule generally known as B7. B7 was originally described as a B cell activation antigen because it was found on B cells and was termed B7/BB-1 (Linsley et al, *Proc. Natl. Acad. Sci. USA* 87:5031-5035 (1990). Hereafter, this molecule will be referred to as B7, B7-1 or B7.1). B7 and more recently described 137 homologues are also members of the Ig superfamily. In contrast to CD28 and CTLA-4, B7 comprises two extracellular Ig domains, an N-terminal variable (V)-like domain followed by a constant (C)-like domain.

B7 family members are generally expressed on APCs and, as noted, are of critical importance to the activation of naive T cells. These family members include B7-1 (=B7, also designated CD80) and B7-2 (also designated CD86). References describing B7-1 include Schwartz, R. H. *Cell* 71:1065-1068, 1992; Chen, L. et al. Cell 71:1093-1102, 1992; Freeman, G. J. et al. *J. Immunol* 143:2714-2722, 1989; and Freeman, G. J. et al. *J. Exp. Med.* 174:625-631, 1991)). References describing B7-2 include (Freeman, G. J. et al. *Science* 262:909-911 813-960, 1993). To date, both murine B7-1 and B7-2 and human B7-1 and B7-2 have been described (Freeman et al., 1989, supra; 1991, supra; and 1993, supra). Activated human B lymphocytes express CTLA4/CD28 binding counter-receptors B7-2 and B7-3, both of which can deliver costimulatory signals to T cells via either CD28 or CTLA4.

B7-2 is expressed by B cells at about 24 hours following stimulation with either anti-Ig or anti-MHC class II mAbs. B7-2 induces detectable IL-2 secretion and T cell proliferation. At about 48 to 72 hours post activation, B cells express both B7-1 and a third CTLA4 counter-receptor identified by a mAb BB-1 (Yokochi, T, et al. (1982) *J. Immunol.* 128, 823-827), termed B7-3. B7-3 is also expressed on B7-negative activated B cells and can costimulate T cell proliferation without detectable IL-2 production, indicating that the B7-1 and B7-3 molecules are distinct. B7-3 is expressed on a wide variety of cells including activated B cells, activated monocytes, dendritic cells, Langerhans cells and keratinocytes. At 72 hours post B cell activation, the expression of B7-1 and B7-3 begins to decline. The presence of these CTLA4/CD28 binding counter-receptors on the surface of activated B lymphocytes indicates that T cell costimulation is regulated, in part, by the temporal expression of these molecules following B cell activation.

The importance of the B7:CD28/CTLA4 costimulatory pathway(s) has been demonstrated in vitro and in vivo. A direct relationship exists between increased T cell activity and increased B7 expression (Razi-Wolf et al., *Proc. Natl. Acad. Sci. USA,* 89:4210-4214 (1992)). T cells are rendered anergic when they, encounter peptides antigens on cells lacking a costimulatory ligand that binds CD28 Blockade of this costimulatory pathway results in the development of antigen specific tolerance in murine and humans systems (Harding et al., supra; Lenschow, D. J. et al. (1992) *Science.* 257, 789-792; Turka, L A et al. (1992) *Proc. Natl. Acad. Sci. USA.* 89, 11102-11105; Gimmi, C D et al. (1993) *Proc. Natl. Acad. Sci. USA* 90, 6586-6590; Boussiotis, V. et al. (1993) *J. Exp. Med.* 178, 1753-1763). Conversely, expression of B7 by B7-negative murine tumor cells induces T-cell mediated specific immunity accompanied by tumor rejection and long lasting protection to tumor challenge (Chen, L, et al. (1992) *Cell* 71:1093-1102; Townsend et al., supra; Baskar, S, et al. (1993) *Proc. Natl. Acad. Sci.* 90, 5687-5690.). Therefore, manipulation of the B7:CD28/CTLA4 pathway offers great potential to stimulate or suppress immune responses in humans.

Interactions between CD28 and B7 have been characterized using genetic fusions of the extracellular portions of B7 or CD28 with Ig Cγ1 chains (Linsley et al, *J. Exp. Med.* 173:721-730 (1991)). When B7Ig fusion proteins are immobilized, or when B7 is expressed on the surface of a cell, such as a transfected CHO cell, they costimulate T cell proliferation. T cell stimulation with B7+CHO cells also specifically stimulates increased levels of transcripts for IL-2.

U.S. Pat. No. 5,521,288 describes a method for regulating immune responses by contacting CD28 positive T cells with fragments encoded by parts of DNA encoding B7, primarily corresponding to the extracellular domain (ECD) of B7. Immune responses were also regulated by derivatives of B7 that were are fusion protein constructs including at least a portion of B7 ECD and another protein, such as the human IgCγ1 domain that altered the solubility, binding affinity and/or valency of B7. For example DNA encoding amino acid residues from positions 1-215 of the B7 ECD was joined to DNA encoding amino acid residues of the sequences corresponding to the hinge, CH2 and CH3 regions of human IgCγ1 to form a DNA fusion product which encoded a B7Ig fusion protein. Also disclosed was a method for treating an immune system disease mediated by T cells by administering B7 or B7Ig fusion protein to react with T cells by binding the CD28 receptor. T cell proliferation in graft versus host disease was inhibited by reacting CD28+ T cells with B7 antigen or B7Ig fusion protein in combination with an immunosuppressant.

U.S. Pat. No. 5,861,310 discloses tumor cells modified to express one or more T cell costimulatory molecules, including B7-2 and B7-3. One embodiment includes further expression of B7. Modification was by transfection with nucleic acid encoding the B7-2, 137-3 or B7 proteins. Tumor cells could also be genetically modified in vivo. Such modified tumor cells said to be useful for treating a patient with a tumor, to prevent or inhibit metastatic spread or inhibit recurrence of the tumor. This document disclosed a method for specifically inducing a CD4+ T cell response against a tumor.

U.S. Pat. No. 5,942,607 discloses isolated nucleic acids encoding novel CTLA4/CD28 ligands which costimulate T cell activation. In one embodiment, the isolated nucleic acid encoded B7-2. Also disclosed was a nucleic acid comprising at least a portion of the disclosed full length B7-2 sequence. According to this document, the nucleic acid sequences could be integrated into various expression vectors which could direct the synthesis of the corresponding proteins or peptides in a variety of host cells including mammalian and insect cells. Also disclosed were host cells transformed to produce proteins or peptides encoded by these nucleic acid sequences and isolated proteins and peptides which comprise at least a portion of the B7-2 sequence.

Dong H et al., *Nat Med* 1999 5:1365-1399, described a third member of the 137 family, designated B7-H1 that does not bind CD28, CTLA4 or ICOS (inducible co-stimulator). Ligation of B7-H1 co-stimulated T-cell responses to polyclonal stimuli and alloantigens, and preferentially stimulated the production of interleukin-10. IL-2, produced in small amounts, was required for the effect of B7-H1 co-stimulation. This study defined a previously unknown co-stimulatory molecule that may be involved in the negative regulation of cell-mediated immune responses. The same laboratory (Wang S et al., *Blood.* 2000; 96:2808-2813) described a new human B7-like gene designated B7-H2, the expression of which was detected on the surface of monocyte-derived immature DCs. Soluble B7-H2 and an Ig fusion protein, B7-H2Ig, bound to activated, but not resting, T cells. This binding was inhibited by a soluble form of ICOS (ICOSIg) but not by CTLA4Ig. ICOSIg stained CHO cells transfected with the B7-H2 gene. Using suboptimal cross-linking of CD3 as a stimulus, costimulation of T-cell proliferation by B7-H2Ig was found to be dose-dependent and correlated with secretion of IL-2, whereas optimal CD3 ligation preferentially stimulated IL-10 production. The authors concluded that B7-H2 is a putative ligand for the ICOS T-cell molecule.

Swallow M M et al., Immunity, 1999, 11:423-432 reported cloning of a novel gene, b7h, a is a close homolog of B7 molecules that are expressed on APCs. B7h costimulated proliferation of purified T cells by acting on a receptor distinct from CD28 or CTLA-4. Surprisingly, although B7h was expressed in unstimulated B cells, its expression was induced in nonlymphoid cells (3T3 cells; embryonic fibroblasts)

treated with TNFα and was upregulated in nonlymphoid tissue of mice treated with LPS, a potent activator of TNFα. These studies defined a novel costimulatory ligand of T cells and suggested that induction of B7h by TNFα may directly augment recognition of self during inflammation Yoshinaga S K et al., *Nature*, 1999, 402:827-832, described a new murine costimulatory receptor-ligand pair. The receptor, related to CD28, was the murine homologue of the human protein ICOS, and was expressed on activated T cells and resting memory T cells. The ligand, which was homologous to B7 molecules was designated B7-related protein-1 (B7RP-1). B7RP-1 is a type 1 transmembrane protein with 20% and 19% amino acid identity to murine B7.1 (CD80) and B7.2 (CD86), respectively. This homology is significant as B7.1 and B7.2 share only 27% amino acid identity (Freeman, G J et al., *J. Exp. Med.* 178:2185-2192 (1993)). This homology includes the cysteines that are important for Ig loop formation at conserved locations (residues 62, 138, 185 and 242 from the initiating methionine). The overall length and relative position of the transmembrane domain of B7RP-1 are similar to those of the B7 molecules (Greenfield, E A et al., *Crit. Rev. Immunol.* 18:389-418 (1998)). B7RP-1 was shown to be expressed on B cells and macrophages. ICOS and B7RP-1 did not interact with proteins in the CD28-B7 pathway, and B7RP-1 co-stimulated T cells independently of CD28. Transgenic mice expressing a fusion protein between B7RP-1 and the Fc portion of Ig ("B7-RP1-Fc") had lymphoid hyperplasia in spleen, lymph nodes and Peyer's patches. Co stimulatory activity of B7RP-1 in vivo was found by demonstrating enhanced delayed-type hypersensitivity in antigen-presensitized mice treated with B7RP-1-Fc at the time of antigen challenge. The authors concluded that ICOS and B7RP-1 define a distinct new receptor-ligand pair that is structurally related to CD28-B7 and is involved in the adaptive immune response.

Yoshinaga S K et al., Int Immunol, 2000 October, 12:1439-1447, reported co-stimulation of human T cells through the human B7RP-1 and ICOS interaction. This ligand-receptor pair interacted with a $K_D$ of approximately 33 nM and an off-rate having a $t_{(1/2)}$ of >10 min. TNFα differentially regulated expression of human B7RP-1 on B cells, monocytes and DC. TNFα enhanced B7RP-1 expression on B cells and monocytes, but inhibits expression on DC. A human B7RP-1-Fc protein, or cells that expressed membrane-bound B7RP-1, co-stimulated T cell proliferation in vitro. Specific cytokines, such as IFNγ and IL-10, were induced by B7RP-1 co-stimulation. Although IL-2 levels were not significantly increased, B7RP-1-induced co-stimulation was dependent on IL-2. These studies defined the human ortholog to murine 137RP-1 and characterized its interaction with human ICOS.

PD-1 is an immuno-inhibitory receptor expressed by activated T, B and myeloid cells. Mice deficient in PD-1 showed multiple forms of autoimmunity due to the loss of peripheral tolerance, Freeman, G J et al., J. Exp. Med. 192:1027-1034 (2000) reported that the ligand of PD-1 (PD-L1) is a member of the B7 gene family. Engagement of PD-1 by PD-L1 resulted in inhibition of TCR-mediated lymphocyte activation (proliferation, cytokine secretion). In addition, PD-1 signaling inhibited suboptimal levels of CD28-mediated costimulation. PD-L1 is expressed by APCs (human monocytes stimulated with IFNγ, activated human DCs). In addition, PD-L1 was shown to be expressed in heart and lung. The authors speculated that relative magnitude of inhibitory PD-L1 signals and costimulatory B7-1/B7-2 signals on APCs may determine the extent of T cell activation and the threshold between tolerance and autoimmunity. The presence of PD-L1 on nonlymphoid tissues may contribute to the magnitude of immune responses at sites of inflammation.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

In order to identify genes encoding novel dendritic cell (DC) specific costimulatory molecules for T cell activation, the inventors screened a subtracted cDNA library between DCs and activated macrophages. This cDNA subtraction approach defines genes expressed by DCs but not by activated macrophages. Use of this approach has led to discover of several novel DC-specific genes that are useful in enhancing the potency of vaccines that depend on activation of T cells. The present application focuses on one such gene.

Based on presence in the DC library and absence from the activated macrophage library, a novel coding sequence, termed "B7-DC" was identified. The B7-DC gene is a member of the B7 family of genes encoding costimulatory molecules. B7-DC is the first B7 family member with DC-specific expression and different receptor specificity. The product of this gene has an important role in mediating the unique ability of DCs to stimulate T cells. Functional analysis indicated that B7-DC is more active than B7-1 in stimulating IFNγ production by T cells. B7-DC DNA and polypeptides are therefore useful in compositions and methods to enhance the efficacy of cellular and molecular vaccine compositions, whether antigen-specific or not.

In one embodiment, the present invention provides an isolated nucleic acid molecule that encodes a mammalian protein termed B7-DC that is selectively expressed on dendritic cells as compared to activated macrophages. The nucleic acid molecule preferably comprises a nucleotide sequence selected from SEQ ID NO:1 (of human origin) or SEQ ID NO:5. (of murine origin). The invention is also directed to an isolated nucleic acid that hybridizes with the above nucleic acid molecule under stringent hybridization conditions. Preferred stringent conditions include incubation in 6× sodium chloride/sodium citrate (SSC) at about 45° C., followed by a wash in about 0.2×SSC at a temperature of about 50° C. Preferably the above nucleic acid molecule comprises the nucleotide sequence SEQ ID NO:1. A preferred nucleic acid molecule as above encodes a protein having an amino acid sequence selected from SEQ ID NO:2 and SEQ ID NO:4 or encodes a biologically active fragment, homologue or other functional derivative of the protein. Preferably, the nucleic acid molecule encodes the protein having the sequence SEQ ID NO:2 (B7-DC of human origin) or encodes the biologically active fragment, homologue or other functional derivative of SEQ ID NO:2.

In a preferred embodiment, the nucleic acid molecule encodes the extracellular domain of the B7-DC protein, which includes residues 26-221, which encodes a co-stimulatory homologue, fragment or other functional derivative thereof.

In another embodiment, the above nucleic acid molecule of encodes a B7-DC fusion protein which comprises:
(a) a first nucleic acid sequence encoding a first polypeptide that is all or a part of a B7-DC protein (preferably SEQ ID NO:2 or SEQ ID NO:4);

(b) optionally, fused in frame with the first nucleic acid sequence a linker nucleic acid sequence encoding a linker peptide; and
(c) a second nucleic acid sequence that is linked in frame to the first nucleic acid sequence or to the linker nucleic acid sequence and that encodes a second polypeptide.

The second polypeptide preferably consists of one or more domains of an Ig heavy chain constant region, preferably the two C domains of human IgG, preferably IgG1.

Also provided is an expression vector comprising any of the above nucleic acid molecules operatively linked to
(a) a promoter and
(b) optionally, additional regulatory sequences that regulate expression of the nucleic acid in a eukaryotic cell.

The above expression vector may be a plasmid or a viral vector. These vectors include self replicating RNA replicons (DNA-launched or RNA), suicide RNA vectors DNA viruses (such as adenovirus, vaccina virus, etc.) and RNA virions grown on packaging cell lines.

The vector DNA or RNA may be complexed to gold particles for gene gun-mediated introduction to a host or complexed with other polymers, for example, in controlled release formulations, that enhance delivery to the desired target cells and tissues.

Also included is a vector composition which comprises:
(a) a first recombinant expression vector having incorporated in its sequence a nucleotide sequence encoding an antigen of interest against which an immune response is to be induced; and
(b) a second recombinant expression vector having incorporated in its nucleic acid sequence or more nucleotide sequences encoding a co-stimulator polypeptide, at least one of which polypeptides is B7-DC, or a biologically active fragment, homologue or other functional derivative thereof,
wherein the expression vectors are able to co-infect or co-transfect a host cell resulting in co-expression of the antigen and the costimulator polypeptide, fragment, homologue or derivative.

In a modification of the above embodiment, the invention provides a third nucleic sequence encoding a targeting protein that (i) promotes spread of the expressed product (antigen) between cells, preferably APCs, (ii) increases the display of the antigen on APCs in which the nucleic acid is expressed, and/or (iii) promotes the re-presentation (cross-priming) and display of the antigen in APCs of a host into which the vector is introduced. The targeting protein-encoding nucleic acid may be fused to the nucleic acid encoding the antigen or the co-stimulator or both acid the first or the second vector includes nucleic acid. In one embodiment, the vector composition combines the antigen-encoding nucleic acid, the co-stimulator-encoding nucleic acid (preferably B7-DC) and a "targeting" protein-encoding nucleic acid into a single fused construct.

This invention includes a cell transformed or transfected with any of the above nucleic acid molecules or expression vectors. The cell is preferably a eukaryotic cell, more preferably a mammalian cell, most preferably a human cell. The cell may be a dendritic cell or a progenitor thereof. In another embodiment, the cell is a tumor cell, preferably a tumor cell that bears an antigen that is the same as, or cross-reactive with, an antigen on a tumor in the host against which an immune response is desired.

A preferred embodiment is an isolated mammalian tumor cell transfected with an exogenous nucleic acid molecule encoding a mammalian B7-DC protein preferably SEQ ID NO:2 or SEQ ID NO:4) or a biologically active fragment, homologue or other functional derivative thereof, such that when the protein, fragment, homologue or derivative is expressed by the tumor cell, and the tumor cell is contacted with T cells
(i) the B7-DC protein, fragment, homologue or derivative binds to the T cells; and
(ii) the tumor cell costimulates the T cells to proliferate and/or to produce and secrete cytokines.

The present invention is also directed to a polypeptide that is selectively expressed on dendritic cells as compared to activated macrophages and has the following functional properties:
(a) binds to a binding partner on T cells; and
(b) costimulates T cells to proliferate and/or to produce and secrete cytokines.

Also included are biologically active fragments, homologues or other functional derivatives of the polypeptide.

The polypeptide, fragment, homologues or functional derivative is preferably encoded by a nucleic acid molecule having the sequence SEQ ID NO:1 or SEQ ID NO:5, or a fragment, homologue or equivalent of the nucleic acid molecule. A preferred polypeptide has the amino acid sequence SEQ ID NO:2 or SEQ ID NO:4.

The polypeptide or a biologically active fragment, homologues or other functional derivative of the polypeptide may be produced by recombinant expression of one of the above nucleic acids.

A preferred polypeptide comprises the extracellular domain of the B7-DC protein, preferably
(a) amino acid residues 26-221 of SEQ ID NO:2 (human) or
(b) amino acid residues 26-221 of SEQ ID NO:4 (mouse).

The above polypeptide may consist essentially of the extracellular domain of B7-DC Also provided is a B7-DC fusion polypeptide having a first fusion partner comprising all or a part of a B7-DC protein fused
(i) directly to a second polypeptide or,
(ii) optionally, fused to a linker peptide sequence that is fused to the second polypeptide.

The above A B7-DC fusion protein may also be fused to a second polypeptide, preferably one of more domains of an Ig heavy chain constant region, preferably having an amino acid sequence corresponding to the hinge, $C_H2$ and $C_H3$ regions of a human immunoglobulin Cγ1 chain.

In one embodiment of the above fusion protein, the first fusion partner is the extracellular domain of a B7-DC protein, the full length sequence of which is SEQ ID NO:2 or SEQ ID NO:4.

The fusion protein preferably binds to a binding partner on T cells and co-stimulates T cells in the presence of an adequate stimulus to the T cell receptor.

Also provided is a dimeric or trimeric fusion protein which is a dimer or trimer of the above fusion proteins. Preferably, the chains are tandemly linked via disulfide bonds or other interchain covalent bonds.

In a preferred dimeric fusion protein, the dimer results from the covalent bonding of Cys residue in the $C_H$ regions of two of the Ig heavy chains that are the same Cys residues that are disulfide linked in dimerized normal Ig H chains.

The fusion protein of the invention may comprise a multimer of two or more repeats of the first fusion partner linked end to end, directly or with a linker sequence between one or more monomers.

The present invention also provides an antibody that is specific for an epitope of a B7-DC protein, which epitope is not present in a known member of a B7 family protein. The epitope may be a linear or conformational epitope of a polypeptide of SEQ ID NO:2 or SEQ ID NO:4. The antibody is preferably a monoclonal antibody, more preferably a human or humanized (via engineering) monoclonal antibody.

Also provided is a method of using the above antibody to identify or quantitate cells expressing a B7-DC polypeptide on their surface in a cell population, comprising
(a) contacting cells of the population with the above antibody so that the antibody binds to cells expressing the epitope;
(b) assessing the presence of or quantitating the number of cells to which the antibody is bound.

Another method is provided for isolating cells expressing a B7-DC polypeptide on their surface from a cell population, comprising
(a) contacting the population with the above antibody so that the antibody binds to cells expressing the epitope;
(b) positively selecting cells to which the antibody has bound or negatively selecting cells to which the antibody has not bound.

Also provided is a method of detecting the presence or quantitating a B7-DC polypeptide, fragment or homologue in a sample, comprising the steps of:
(a) contacting the sample with the antibody of claim 43 such that the antibody binds to any polypeptides or fragments bearing the epitope;
(b) detecting the presence of, or quantitating the polypeptides or fragments bound to the antibody.

The present invention is also directed to a method of inducing or increasing the expression of a B7-DC polypeptide in an antigen presenting cell or a progenitor thereof to increase the ability of the cell to co-stimulate T cells in vitro or in vivo in the presence of an adequate stimulus to the T cell receptor, comprising transforming or transfecting the antigen presenting cell or progenitor cell with the expression vector as described above, such that the expression of the B7-DC polypeptide is induced or increased on the cells. The antigen presenting cells are preferably dendritic cells and the progenitors are dendritic cell progenitors.

The present invention provides method for stimulating immune responses using cellular co-stimulatory compositions as well as polypeptide co-stimulators. One method for increasing the T cell response of a mammalian subject to antigenic stimulation comprises administering to the subject an effective amount of cells as described above, preferably tumor cells, in conjunction with an antigenic stimulus, wherein the cells are effective to increase the T cell response of the subject to the antigenic stimulation. The foregoing is preferably accomplished by co-injection of the antigen and the co-stimulatory composition.

A method for increasing the T cell response of a mammalian subject to antigenic stimulation with a tumor-associated antigen, comprises administering to the subject an effective amount of tumor cells as described above, wherein the tumor cells express the antigen, the administration of the tumor cells being effective to increase the T cell response of the subject to the tumor antigen stimulation.

A method for increasing the T cell response of a mammalian subject to antigenic stimulation, comprising administering to the subject an effective amount of a polypeptide, fragment, homologue or functional derivative as above, or a fusion polypeptide or protein as above, in conjunction with an antigenic stimulus, wherein the administration of the polypeptide is effective to increase the T cell response of the subject to the antigenic stimulation.

This invention also provides a method for inhibiting a T cell response of a mammalian subject to antigenic stimulation, comprising administering to the subject an effective amount of an antibody as described, wherein the administration of the antibody is effective to block stimulation of T cells or to eliminate antigen-reactive T cells, thereby inhibiting the T cell response. These methods are particularly useful for treating a subject with a tissue or organ transplant to inhibit transplant rejection and/or to promote engraftment. In the case of an autoantigen, the method blocks or diminishes autoimmune reactions and their pathologic sequelae.

The present invention provides therapeutic methods using T cells that have undergone ex vivo stimulation with the compositions of this invention. One method for increasing the immune response of a mammalian subject to antigenic stimulation comprises:
(a) obtaining T cells from the subject, from an immunologically compatible donor for said subject, or from an immunologically acceptable cultured cell line;
(b) contacting the T cells ex vivo with an effective amount of cells as described above, wherein the contacting is effective to increase the response of the T cells to antigenic stimulation; and
(c) administering the T cells of step (b) to the subject, thereby increasing the immune response of the subject.

In another embodiment, the method for increasing the immune response of a mammalian subject to antigenic stimulation comprises:
(a) obtaining T cells from obtaining T cells from the subject, from an immunologically compatible donor for said subject, or from an immunologically acceptable cultured cell line;
(b) contacting the T cells ex vivo with an effective amount of (i) a polypeptide, fragment, homologue or functional derivative as described above, or (ii) a fusion polypeptide as above, wherein the contacting is effective to increase the response of the r cells to antigenic stimulation; and
(c) administering the T cells of step (b) to the subject, thereby increasing (or generating) an immune response of the subject.

Also provided herein is a vaccine composition comprising
(a) (i) cells as described above that express a B7-DC construct, (ii) a B7-DC polypeptide, fragment, homologue or functional derivative, (iii) a B7-DC fusion polypeptide or protein
(b) generally, an additional source of antigen to which an immune response is desired—though this may not be required in the case of the cell-based vaccine wherein the cells themselves expresses the antigen (as in the case of tumor antigen-bearing tumor cells);
(c) optionally, a general immunostimulatory agent or adjuvant; and
(d) a pharmaceutically and immunologically acceptable excipient or carrier for (a), b) and (c).

A method for inducing or enhancing an immune response to an antigen in a mammalian subject comprises administering to the subject an effective amount of the above vaccine composition.

Also provided is a co-stimulatory composition for use with an antigen or a vaccine, comprising:
(a) a B7-DC polypeptide (preferably SEQ ID NO:2 or SEQ ID NO:4), a fragment, a homologue or a functional derivative thereof, or a B7-DC fusion polypeptide, and
(b) a pharmaceutically and immunologically acceptable excipient or carrier.

A method for potentiating an immune response to an antigen or a vaccine in a mammalian subject, comprises administering to the subject, in combination with the antigen or vaccine, the above costimulatory composition.

A method of stimulating a systemic immune response to a tumor in a subject, comprises administering to the subject genetically altered tumor cells which cells
(a) are derived from a tumor in the subject, and
(b) are genetically altered by introduction ex vivo of a B7-DC nucleic acid as descried above, the expression of which provides a costimulatory signal in the subject,
wherein the administering results in stimulation of the systemic immune response directed to the tumor.

The tumor cells are preferably treated, preferably by irradiation, to prevent their growth after they have been administered.

The subject may be subjected to a tumor-reducing regimen of chemotherapy, irradiation or surgical resection prior to the administering of the above therapeutic compositions.

Also provided is a method of inducing an antitumor response in a mammal having an antigen-positive tumor, comprising:
(a) providing cells of the tumor or of a tumor cell line that
  (i) express antigens shared with the tumor of the mammal;
  (ii) are transfected with a B7-DC-encoding nucleic acid vector as above, that when expressed, s a B7-DC molecule causes the cells to co-stimulate a T cell response to antigens of the tumor;
  (iii) optionally, are irradiated prior to step (b);
(b) administering an effective number of the cells to the mammal, which cells express the antigens and the B7-DC molecule;
thereby inducing an antitumor response In the above method, the antitumor response is characterized by:
  (A) at least a 50% decrease in the sum of the products of maximal perpendicular diameters of all measurable lesions;
  (B) no evidence of new lesions, and
  (C) no progression of any preexisting lesions.

Also provided is a method of inducing regression or attenuation of primary growth or regrowth of a tumor in a mammal bearing the tumor, comprising:
(a) providing cells of the tumor or of a tumor cell line that
  (i) express antigens shared with the tumor of the mammal;
  (ii) are transfected with a B7-DC-encoding nucleic acid vector as above, that, when expressed, as a B7-DC molecule causes the cells to co-stimulate a T cell response to antigens of the tumor;
  (iii) optionally, are irradiated prior to step (b);
(b) administering an effective number of the cells to the mammal, which cells express the antigens and the B7-DC molecule;
thereby inducing a systemic immune response specific to the tumor antigens of the melanoma, thereby inducing the regression or the attenuation A method of inhibiting recurrent growth of an antigen-positive tumor in a mammal, comprises:
(a) providing cells of the tumor or of a tumor cell line that
  (i) express antigens shared with the tumor of the mammal;
  (ii) are transfected with a B7-DC-encoding nucleic acid vector as above, that, when expressed, causes the cells to co-stimulate a T cell response to antigens of the tumor;
  (iii) optionally, are irradiated prior to step (b);
(b) administering an effective number of the cells to the mammal, which cells express the antigens and the B7-DC molecule;
thereby inducing a systemic immune response specific to the tumor antigens in the mammal, which immune response inhibits the recurrent growth of the tumor.

Another embodiment is directed to a method of providing a co-stimulatory signal in the vicinity of locally-administered antigen in a mammalian subject to promote the local generation of an inflammatory and immune response that results in a state of systemic immunity to the antigen, the method comprising administering to a local site in the subject
(a) cells that express a costimulation-effective amount of B7-DC polypeptide, fragment, homologue or functional derivative as above, and
(b) the antigen
such that costimulation in physical proximity with the antigen promotes the local generation of the response and results in the state of systemic immunity.

In the above method, the antigen is preferably a tumor antigen that is administered in (b) in the form of tumor cells or subcellular antigenic material. The tumor cells may also be the cells that express the B7-DC polypeptide, fragment, homologue or derivative in (a).

DESCRIPTION OF THE PREFERRED EMBODIMENTS

Figure 1:
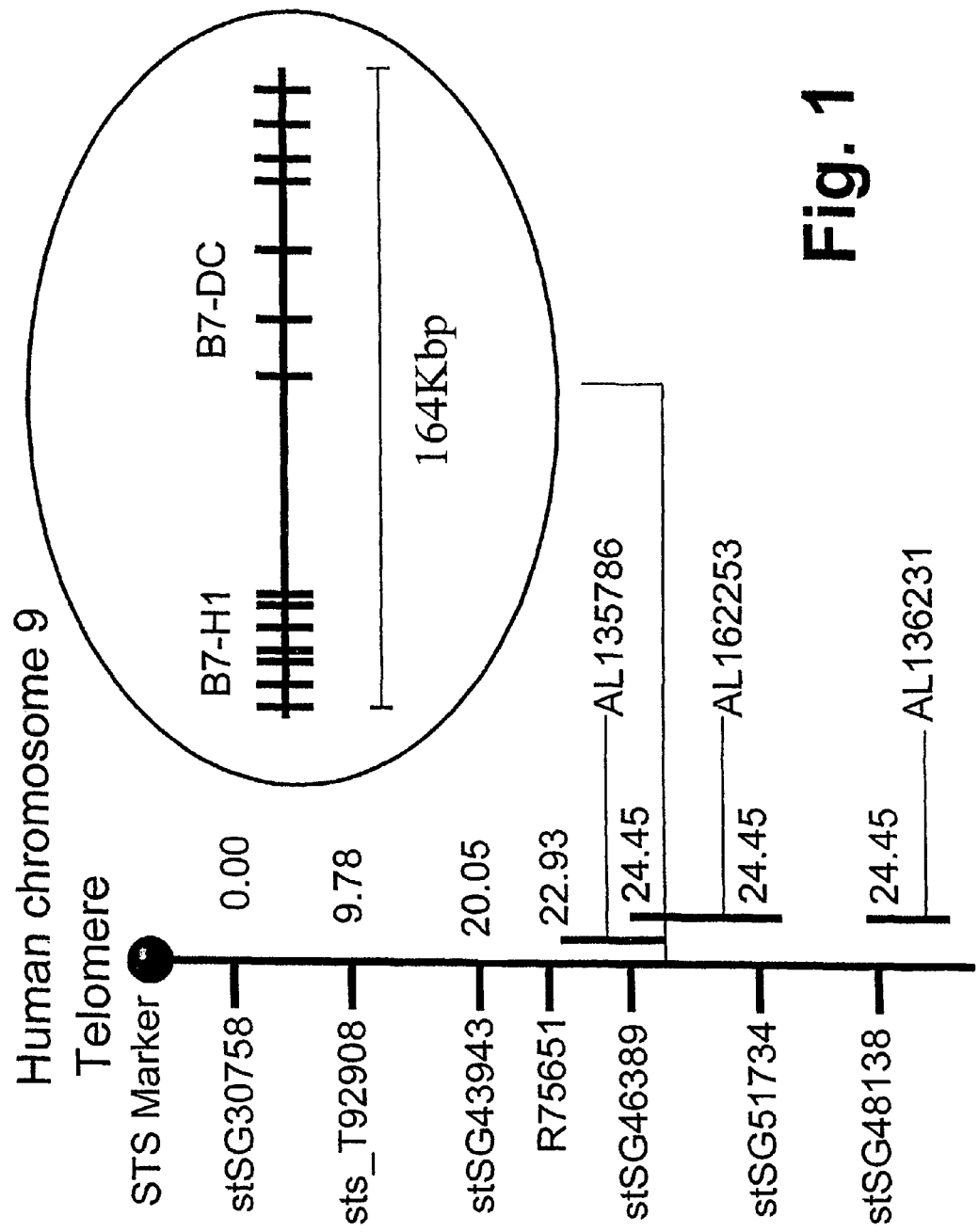
FIG. 1 is a diagram showing shows the map of hB7-DC which is localized on human chromosome 9p24. hB7-DC maps to BAC clone RPCI-11.2.

The present inventors have now identified new proteins and nucleic acids that serve as the basis for improved immunotherapeutic compositions and methods. Human and murine forms of a novel costimulatory protein named B7-DC have been discovered and are disclosed herein.

DNA encoding human B7-DC has the nucleotide sequence SEQ ID NO:1, show below.

```
  1 atgatcttcctcctgctaatgttgagcctggaattgcagcttcaccagatagcagcttta 61 ttcacagtgacagtccctaaggaactgtacataatagagcatggcagcaatgtgaccctg 121 gaatgcaactttgacactggaagtcatgtgaaccttggagcaataacagccagtttgcaa 181 aaggtggaaaatgatacatccccacaccgtgaaagagccactttgctggaggagcagctg 241 cccctagggaaggcctcgttccacatacctcaagtccaagtgagggacgaaggacagtac 301 caatgcataatcatctatggggtcgcctgggactacaagtacctgactctgaaagtcaaa 361 gcttcctacaggaaaataaacactcacatcctaaaggttccagaaacagatgaggtagag 421 ctcacctgccaggctacaggttatcctctggcagaagtatcctggccaaacgtcagcgtt 481 cctgccaacaccagccactccaggacccctgaaggcctctaccaggtcaccagtgttctg 541 cgcctaaagccaccccctggcagaaacttcagctgtgtgttctggaatactcacgtgagg 601 gaacttactttggccagcattgaccttcaaagtcagatggaacccaggacccatccaact 661 tggctgcttcacattttcatccctcctgcatcattgctttcatttcatagccacagtg 721 atagccctaagaaaacaactctgtcaaaagctgtattcttcaaaagacacaacaaaaga 781 cctgtcaccacaacaaagagggaagtgaacagtgctatc                        819
```

The human B7-DC protein has the amino acid sequence SEQ ID NO:2, shown below (with leader sequence, transmembrane domain and cytoplasmic tail annotated):

```
                putative leader sequence
    1 MIFLLLMLSL  ELQLHQIAAL  FTVTVPKELY  IIEHGSNVTL  ECNFDTGSHV   50

51 NLGAITASLQ  KVENDTSPHR  ERATLLEEQL  PLGKASFHIP  QVQVRDEGQY  100

101 QCIIIYGVAW  DYKYLTLKVK  ASYRKINTHI  LKVPETDEVE  LTCQATGYPL  150

151 AEVSWPNVSV  PANTSHSRTP  EGLYQVTSVL  RLKPPPGRNF  SCVFWNTHVR  200 putative TM domain
  201 ELTLASIDLQ  SQMEPRTHPT  WLLHIFIPSC  IIAFIFIATV  IALRKQLCQKL 250

251 LYSSKDTTKR  PVTTTKREVN  SAI                                 273
         cytoplasmic tail
```

The extracellular domain of this protein is from residue P[26] through residue W[221].

A DNA clone that includes the coding sequence encoding murine B7-DC has the nucleotide sequence SEQ ID NO:3, show below. The coding sequence (underscored, set off in triplets) begins from the methionine codon atg (bolded) beginning at nucleotide 210 and terminates with the tag stop codon (bolded) (nucleotides 951-953)

```
gaattcggcacgaggtcaaatgtggcatatctttgttgtctccttctgtctcccaactag      60
agagaacacacttacggctcctgtcccgggcaggtttggttgtcggtgtgattggcttcc     120
agggaacctgatacaaggagcaactgtgtgctgccttttctgtgtctttgcttgaggagc     180
tgtgctgggtgctgatattgacacagacc                                    209
atg ctg ctc ctg ctg ccg ata ctg aac ctg agc tta caa ctt cat cct   257
gta gca gct tta ttc acc gtg aca gcc cct aaa gaa gtg tac acc gta   305
gac gtc ggc agc agt gtg agc ctg gag tgc gat ttt gac cgc aga gaa   353
tgc act gaa ctg gaa ggg ata aga gcc agt ttg cag aag gta gaa aat   401
gat acg tct ctg caa agt gaa aga gcc acc ctg ctg gag gag cag ctg   449
ccc ctg gga aag gct ttg ttc cac atc cct agt gtc caa gtg aga gat   497
tcc ggg cag tac cgt tgc ctg gtc atc tgc ggg gcc gcc tgg gac tac   545
aag tac ctg acg gtg aaa gtc aaa gct tct tac atg agg ata gac act   593
agg atc ctg gag gtt cca ggt aca ggg gag gtg cag ctt acc tgc cag   641
gct aga ggt tat ccc cta gca gaa gtg tcc tgg caa aat gtc agt gtt   689
cct gcc aac acc agc cac atc agg acc ccc gaa ggc ctc tac cag gtc   737
acc agt gtt ctg cgc ctc aag cct cag cct agc aga aac ttc agc tgc   785
atg ttc tgg aat gct cac atg aag gag ctg act tca gcc atc att gac   833
cct ctg agt cgg atg gaa ccc aaa gtc ccc aga acg tgg cca ctt cat   881
gtt ttc atc ccg gcc tgc acc atc gct ttg atc ttc ctg gcc ata gtg   929
ata atc cag aga aag agg atc tag                                   953
gggaagctgtattacggaagaagtggtctcttcttcccagatctggacctgcggtcttgg    1013
gagttggaaggatctgatgggaaaccctcaagagacttctggactaaaagtgagaatctt    1073
gcaggacctgccatttgcacttttgaaccctttggacggtgacccagggctccgaagagg    1133
agcttgtaagactgacaatcttccctctgtctcaagactctctgaacagcaagaccccaa    1193
tggcactttagacttacccctgggatcctggaccccagtgagggcctaaggctcctaatg    1253
actttcagggtgagaacaaaaggaattgctctccgccccaccccacctcctgctttccg     1313
cagggagacatggaaattcccagttactaaaatagattgtcaatagagttatttatagcc    1373
ctcatttcctccggggacttggaagcttcagacagggttttcataaacaaagtcataac     1433
tgatgtgttttacagcatcctagaatcctggcagcctctgaagttctaattaactggaag    1493
catttaagcaacacgtcaagtgccctgctgtggtatttgtttctacttttctgttttta     1553
aagtgtgagtcacaaggtaattgttgtaacctgtgatatcactgtttcttgtgtctcttc    1613
tttcaactacatcttttaaaacaaaaaaaaaaaaaaaaaaa                        1655
```

SEQ ID NO:5 is the coding sequence part of SEQ ID NO:3.

The murine B7-DC protein, encoded by the coding region of SEQ ID NO:3, (i.e., by SEQ ID NO:5) has the amino acid sequence SEQ ID NO:4 shown below (with leader sequence, transmembrane domain and cytoplasmic tail annotated):

```
         putative leader sequence
  1 MLLLLLPILNL SLQLHPVAAL FTVTAPKEVY TVDVGSSVSL ECDFDRRECT      50

51 ELEGIRASLQ KVENDTSLQS ERATLLEEQL PLGKALFHIP SVQVRDSGQY      100

101 RCLVICGAAW DYKYLTVKVK ASYMRIDTRI LEVPGTGEVQ LTCQARGYPL      150

151 AEVSWQNVSV PANTSHIRTP EGLYQVTSVL RLKPQPSRNF SCMFWNAHMK      200 putative TM domain
201 ELTSAIIDPL SRMEPKVPRT WPLHVFIPAC TIALIFLAIV IIQRKRI         247
                                                      cyto-
    . tail
```

The extracellular domain of this protein is from residue $P^{26}$ through residue $W^{221}$ The complete DNA sequence of murine B7-DC (originally termed "butyrophilin-like Protein" or "Btdc") has the Genbank accession number AF142780.2

Basic Molecular Approach

This approach is described in more detail in the Examples. The inventors utilized the PCR Select approach which incorporate two important features. First, the initial PCR reaction prior to the hybridization steps requires only small quantity of RNA. This technique allows the use of highly purified mature DCs that have been rendered substantially free of contaminating macrophages, progenitor cells or other potential contaminating cells. Such highly purified DCs are known to be difficult to obtain in very large numbers. Second, the PCR Select procedure enabled cloning of low copy number, differentially expressed genes.

To identify genes differentially expressed by DCs relative to their cellular counterpart, the activated macrophage, and to identify genes associated with DC-specific functions, the present inventors applied a cDNA subtraction approach. They used a modified PCR-based "representative differential analysis" (RDA) combined with suppression PCR (PCR Select™) (Diatchenko, L. et al., *Proc. Natl. Acad. Sci. USA* 93:66025-6030 (1996)).

General Recombinant DNA Methods

Basic texts disclosing general methods of molecular biology, all of which are incorporated by reference, include: Sambrook, X et al., *Molecular Cloning. A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning. A Practical Approach*, vol. I & II, IRE Press, 1985; Albers, B. et al., *Molecular Biology of the Cell*, 2$^{nd}$ Ed., Garland Publishing, Inc., New York, N.Y. (1989); Watson, J D et al., *Recombinant DNA*, 2$^{nd}$ Ed., Scientific American Books, New York, 1992; and Old, R W et al, *Principles of Gene Manipulation: An Introduction to Genetic Engineering*, 2$^{nd}$ Ed., University of California Press, Berkeley, Calif. (1981).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (b) or base pairs (bp). These are estimates derived from agarose or poly-acrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to B7-DC or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of B7-DC, or its fragment or derivative by appropriate host cells, for example COS or CHO cells.

This invention includes isolated nucleic acids having a nucleotide sequence encoding the novel B7-DC, fragments thereof or equivalents thereof. The term nucleic acid as used herein is intended to include such fragments or equivalents. The nucleic acid sequences of this invention can be DNA or RNA. A preferred nucleic acid is cDNA encoding human B7-DC having the sequence SEQ ID NO:1 or equivalents thereof.

Preferably, the nucleic acid of the present invention is a cDNA molecule encoding at least a portion of B7-DC. This cDNA can be made from mRNA extracted from mature DCs or other cells naturally expressing this protein. A nucleic acid sequence encoding B7-DC is obtainable from DC genomic DNA. Thus, DNA encoding B7-DC can be cloned from, a cDNA or a genomic library in accordance with known protocols.

A cDNA nucleotide sequence encoding B7-DC can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism of the B7-DC nucleotide sequence (especially at the third base of a codon) may be manifest as "silent" mutations which do not change the amino acid sequence. However, polymorphisms that involve amino acid sequence changes in B7-DC may exist in a human (or other mammalian) population. Those of skill in the art will appreciate that these allelic variants that have changes in one or more nucleotides (up to about 34% of the total coding sequence) will likely be found in a human population due to natural allelic variation. Any and all such allelic variations and resulting nucleic acid and polypeptide polymorphisms in the DNA encoding B7-DC are within the scope of the invention.

Furthermore, there may be one or more naturally occurring isoforms or related, immunologically cross-reactive family members of the B7-DC protein described herein. Such isoforms or family members are defined as proteins that share function amino acid sequence similarity to B7-DC, even if they are encoded by genes at different loci.

Fragment of Nucleic Acid

A fragment of the nucleic acid sequence is defined as a nucleotide sequence having fewer nucleotides than the nucleotide sequence encoding the full length B7-DC protein. This invention includes such nucleic acid fragments that encode polypeptides which retain (1) the ability of B7-DC to bind to its natural ligand(s) on T cells and (2) to enhance or inhibit (depending on how they are presented) activated T cell mediated immune responses (measured as cytokine production and/or T cell proliferation by T cells that have received a primary activation signal).

For example, a nucleic acid fragment as intended herein encodes a B7-DC polypeptide that retains the ability to bind to the surface of T cells to a receptor that has not yet been identified (but is does not appear to be CD28 or CTLA-4) and deliver a costimulatory signal to T lymphocytes. By another criterion, the present nucleic acid fragment is one that hybridizes with a nucleic acid from another animal species and is therefore useful in screening assays to detect novel proteins that are "cross-reactive" with B7-DC.

Generally, the nucleic acid sequence encoding a fragment of the B7-DC polypeptide comprises of nucleotides from the sequence encoding the mature protein. However, in some instances it may be desirable to include all or part of the leader sequence portion of the nucleic acid. Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

In one embodiment, DNA encoding the amino acid sequence corresponding to the ECD of B7-DC, containing amino acids from about position 26-221, is joined to DNA encoding the amino acid sequences corresponding to the hinge, $C_H2$ and $C_H3$ regions of human Ig Cγ1, using PCR, to form a construct that is expressed as B7-DC-Ig fusion protein.

An analogous DNA molecule encoding a B7-Ig fusion protein was disclosed in U.S. Pat. No. 5,521,288 and deposited with the American Type Culture Collection in Rockville, Md., under accession number 68627.

The techniques for assembling and expressing DNA encoding B7-DC and soluble B7-DC fusion proteins such as synthesis of oligonucleotides, PCR, transforming cells, constructing vectors, expression systems, and the like are well-established in the art. Those of ordinary skill are familiar with the standard resource materials for specific conditions and procedures.

In other embodiments, the DNA encoding a domain or fragment of B7-DC is fused with a nucleic acid encoding most or all of the remaining portion of another B7 family protein, sch as B7.1, B7.2 or B7.3. The complete DNA sequence of human 17.1 (CD80) has the Genbank accession number X60958; the accession number for the mouse sequence is X60958; the accession number for the rat sequence is U05593. The complete cDNA sequence of human B7.2 (CD86) has the Genbank accession number L25259; the accession number for the mouse sequence is L25606.

Expression Vectors and Host Cells

This invention includes an expression vector comprising a nucleic acid sequence encoding a B7-DC polypeptide operably linked to at least one regulatory sequence. "Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of B7-DC: full length protein and its functional derivatives (defined herein) including polypeptide fragments, variants, fusion proteins, etc. Thus, in one embodiment, the expression vector comprises a nucleic acid encoding at least a portion of the B7-DC protein such as the ECD, alone or fused to another protein.

Such expression vectors are used to transfect host cells for expression of the DNA and production of the encoded proteins which include fusion proteins or peptides. It will be understood that a genetically modified cell expressing the B7-DC polypeptide may transiently express the exogenous DNA for a time sufficient for the cell to be useful for its stated purpose. Thus, if the cell is to serve as an immunogen having an augmented costimulatory capacity in vivo or ex vivo, the length of time that expression is required, or that the cell remain alive, is the time necessary for the cell to exert its immunogenic and/or costimulatory function. For example, in the case of a transduced tumor cell expressing the B7-DC of the present invention, expression of B7-DC may be for as little as 6 hours, preferably 24 hours, more preferably for at least 2-4 days. Of course, expression may also be stable (i.e., for the life of the cell). Appropriate expression vectors and regulatory elements (e.g., (e.g., inducible or constitutive promoters) discussed below are selected in accordance with the desired or required stability of expression.

The present in invention provides methods for producing the B7-DC protein, fragments and derivatives. For example, a host cell transfected with a nucleic acid vector that encodes at least a portion of the B7-DC protein is cultured under appropriate conditions to allow expression of B7-DC polypeptide.

Host cells may also be transfected with one or more expression vectors that singly or in combination comprise DNA encoding at least a portion of the B7-DC protein and DNA encoding at least a portion of a second protein, so that the host cells produce fusion polypeptides that include both the portions.

When the recombinant expression vector comprises DNA encoding a portion of B7-DC and DNA encoding another protein, such as human IgCγ1, the resulting fusion protein may have altered solubility, binding affinity and/or valency. A B7-DC Ig fusion protein, for example, is preferably secreted by transfected host cells in cultures and is therefor isolated from the culture medium. Alternatively, if protein is retained in the cytoplasm, the cells are harvested and lysed and the protein isolated from this lysate.

A culture typically includes host cells, appropriate growth media and other byproducts. Suitable culture media are well known in the art. B7-DC protein can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology*, 22: 233-577

(1971)). Once purified, partially or to homogeneity, the recombinant B7-DC proteins of the invention can be utilized in pharmaceutical compositions as described in more detail herein.

Prokaryotic or eukaryotic host cells transformed or transfected to express B7-DC or a homologue or functional derivative thereof are within the scope of the invention. For example, B7-DC may be expressed in bacterial cells such as E. coli, insect cells (baculovirus), yeast, or mammalian cells such as Chinese hamster ovary cells (CHO) or human cells. Other suitable host cells may be found in Goeddel, (1990) supra or are otherwise known to those skilled in the art.

Expression in eukaryotic cells leads to partial or complete glycosylation and/or formation of relevant inter- or intrachain disulfide bonds of the recombinant protein.

Examples of vectors for expression in yeast S. cerevisiae include pYepSec1 (Baldari et al., (1987) EMBO J. 6:229-234), pMFa (Kujan et al. (1982) Cell 30:933-943), pJRY88 (Schultz et al., (1987) Gene 54:113-123), and pYES2 (Invitrogen Corporation, San Diego, Calif.). Baculovirus vectors available for expression of proteins in cultured insect cells (SF 9 cells) include the pAc series (Smith et al., (1983) Mol Cell Biol. 3: 2156-2165,) and the pVL series (Lucklow, V. A., and Summers, M. D., (1989) Virology 170: 31-39). Generally, COS cells (Gluzman, Y., (1981) Cell 23:175-182) are used in conjunction with such vectors as pCDM 8 (Aruffo A. and Seed, B., supra, for transient amplification/expression in mammalian cells, while CHO (dhfr-negative CHO) cells are used with vectors such as pMT2PC (Kaufman et al. (1987), EMBO J. 6: 187-195) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) Gene 69: 301-315) and pET 11d (Studier et al., Gene Expression Technology: Methods in Enzymology 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21 (DE3) or HMS174(DE3) from a resident λ prophage harboring a T7gn1 under the transcriptional control of the lacUV 5 promoter.

One embodiment of this invention is a transfected cell which expresses novel B7-DC de novo. In the case of a cell already expressing B7-DC, such as a mature DC, the transfected cell expresses increased amounts of B7-DC proteins or fragments thereof on the cell surface.

For example, a tumor cell such as a sarcoma, melanoma, leukemia, lymphoma, carcinoma or neuroblastoma is transfected with an expression vector directing the expression of B7-DC on the tumor cell surface. Such transfected tumor cells can be used as immunogens to induce therapeutic anti-tumor immunity as described herein.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., Nature (1981) 292:756; Nambair, K. P., et al., Science (1984) 223:1299; and Jay, E., J Biol Chem (1984) 259:6311.

Synthetic oligonucleotides are prepared by either the phosphotriester method as described by references cited above or the phosphoramidite method as described by Beaucage, S. L., and Caruthers, M. H., Tet Lett (1981) 22:1859; and Matteucci, M. D., and Caruthers, M. H., J Am Chem Soc (1981) 103:3185 and can be prepared using commercially available automated oligonucleotide synthesizers. Kinase treatment of single strands prior to annealing or for labeling is achieved using an excess, e.g., about 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma$-$^{32}$P-ATP (2.9 mCi/mmole), 0.1 mM spermidine, 0.1 mM EDTA.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques, A general description of size separations is found in Methods in Enzymology (1980) 65:499-560.

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are typically performed in 15-50 ml volumes under the following standard conditions and temperatures: for example, 20 mM Tris-HCl pH 7.5, 10 mM MgCl$_2$, 10 mM DTT, 33 µg/ml BSA, 10-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 mM total ends concentration.

In vector construction employing "vector fragments", the fragment is commonly treated with bacterial alkaline phosphatase (BAP) or calf intestinal alkaline phosphatase (CIAP) in order to remove the 5' phosphate and prevent self-ligation. Digestions are conducted at pH 8 in approximately 10 mM Tris-HCl, 1 mM EDTA using BAP or CIAP at about 1 unit/mg vector at 60° for about one hour. The preparation is extracted with phenol/chloroform and ethanol precipitated. Alternatively, re-ligation can be prevented in vectors which have been double digested by additional restriction enzyme and separation of the unwanted fragments.

Any of a number of methods are used to introduce mutations into the coding sequence to generate the variants of the invention. These mutations include simple deletions or insertions, systematic deletions, insertions or substitutions of clusters of bases or substitutions of single bases.

For example, modifications of B7-DC DNA sequence (cDNA or genomic DNA) are created by site-directed mutagenesis, a well-known technique for which protocols and reagents are commercially available (Zoller, M J et al., *Nucleic Acids Res* (1982) 10:6487-6500 and Adelman, J P et al., *DNA* (1983) 2:183-193)). Correct ligations for plasmid construction are confirmed, for example, by first transforming *E. coli* strain MC1061 (Casadaban, M., et al., *J Mol Biol* (1980) 138:179-207) or other suitable host with the ligation mixture. Using conventional methods, transformants are selected based on the presence of the ampicillin-, tetracycline- or other antibiotic resistance gene (or other selectable marker) depending on the mode of plasmid construction. Plasmids are then prepared from the transformants with optional chloramphenicol amplification optionally following chloramphenicol amplification ((Clewell, D B et al., *Proc Natl Acad Sci USA* (1969) 62:1159; Clewell, D. B., *J Bacteriol* (1972) 110:667). Several mini DNA preps are commonly used. See, e.g., Holmes, D S, et al., *Anal Biochem* (1981) 114:193-197; Birnboim, H C et al., *Nucleic Acids Res* (1979) 7:1513-1523. The isolated DNA is analyzed by restriction and/or sequenced by the dideoxy nucleotide method of Sanger (*Proc Natl Acad Sci USA* (1977) 74:5463) as flirter described by Messing, et al., *Nucleic Acids Res* (1981) 9:309, or by the method of Maxam et al. *Methods in Enzymology* (1980) 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69: 301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21 (DE3) or HMS174(DE3) from a resident λ prophage harboring a T7gn1 under the transcriptional control of the lacUV 5 promoter.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably liked" it is not necessary that two sequences be immediately adjacent to one another in the linear sequence.

The preferred promoter sequences of the present invention must be operable in mammalian cells and may be either eukaryotic or viral promoters. Suitable promoters may be inducible, repressible or constitutive. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al, *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-310 (1981)); and the yeast gal4 gene promoter (Johnston, S. A., et al., *Proc. Natl. Acad. Sci.* (*USA*) 79:6971-6975 (1982); Silver, P. A., et al., *Proc. Natl. Acad. Sci.* (*USA*) 81:5951-5955 (1984)). Other illustrative descriptions of transcriptional factor association with promoter regions and the separate activation and DNA binding of transcription factors include: Keegan et al., *Nature* (1986) 231:699; Fields et al., *Nature* (1989) 340:245; Jones, *Cell* (1990) 61:9; Lewin, *Cell* (1990) 61:1161; Ptashne et al., *Nature* (1990) 346:329; Adams et al., *Cell* (1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., *Genes IV*, Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency on the B7-DC-encoding DNA molecule of the present invention.

The nucleic acid sequences of the invention can also be chemically synthesized using standard techniques. Various methods of chemically synthesizing polydeoxy-nucleotides are known, including solid-phase synthesis which, like peptide synthesis, has been fully automated with commercially available DNA synthesizers (See, e.g., Itakura et al. U.S. Pat. No. 4,598,049; Caruthers et at U.S. Pat. No. 4,458,066; and Itakura U.S. Pat. Nos. 4,401,796 and 4,373,071, incorporated by reference herein).

Proteins and Polypeptides

The present invention includes an "isolated" B7-DC protein having the sequence SEQ ID NO:2 or SEQ ID NO:4. While the present disclosure exemplifies the full length human and murine B7-DC protein (and DNA), it is to be understood that homologues of B7-DC from other mammalian species and mutants thereof that possess the characteristics disclosed herein are intended within the scope of this invention.

Also included is a "functional derivative" of B7-DC which is means an amino acid substitution variant, a "fragment," or a "chemical derivative" of B7-DC, which terms are defined below. A functional derivative retains measurable B7-DC activity, preferably that of binding to a receptor on T cells and costimulating T cell activity, which permits its utility in accordance with the present invention. "Functional derivatives" encompass "variants" and "fragments" regardless of whether the terms are used in the conjunctive or the alternative herein.

A functional homologue must possess the above biochemical and biological activity. In view of this functional characterization, use of homologous proteins-B7-DC from other species, including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence. For example, when aligning a second sequence to the human B7-DC protein amino acid sequence (SEQ ID NO:2) having 276 amino acid residues, at least 83, preferably at least 10, more preferably at least 138, even more preferably at least 166, and even more preferably at least 193, 221 or 248 amino acid residues are aligned). The amino acid residues (or nucleotides) at corresponding amino acid positions (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to human or murine B7-DC nucleic acid molecules. BLAST protein searches can be performed with the XBLAST program, score=50, wordlength 3 to obtain amino acid sequences homologous to human or murine B7-DC protein molecules of the invention. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nhn.nih.gov.

Thus, a homologue of the B7-DC protein described above is characterized as having (a) functional activity of native B7-DC, and (b) sequence similarity to a native B7-DC protein (such as SEQ ID NO:2 or SEQ ID NO:4, when determined above, of at least about 30% (at the amino acid level), preferably at least about 50%, more preferably at least about 70%, even more preferably at least about 90%.

It is within the skill in the art to obtain and express such a protein using DNA probes based on the disclosed sequences of B7-DC. Then, the protein's biochemical and biological activity can be tested readily using art-recognized methods such as those described herein, for example, a standard T cell proliferation or cytokine secretion assay. A biological assay of T cell co-stimulation will indicate whether the homologue has the requisite activity to qualify as a "functional" homologue.

Preferred assays measure the functional characteristics of B7-DC such as stimulating T cells synthesis of cytokines, which depends on binding or cross-linking of the TCR ("primary activation signal"), as well as delivery of a costimulatory signal. The binding of B7-DC to its natural ligand(s) on T cells transmits a signal that induces increased cytokine production, such as IL-2' which in turn stimulates proliferation which can also be measured routinely.

A "variant" of B7-DC refers to a molecule substantially identical to either the full protein or to a fragment thereof in which one or more amino acid residues have been replaced (substitution variant) or which has one or several residues deleted (deletion variant) or added (addition variant). A "fragment" of B7-DC-refers to any subset of the molecule, preferably one that includes the ECD, that is, a shorter polypeptide of the full-length protein.

A number of processes can be used to generate fragments, mutants and variants of the isolated DNA sequence. Small subregions or fragments of the nucleic acid encoding the B7-DC protein, for example 1-30 bases in length, can be prepared by standard, chemical synthesis. Antisense oligonucleotides and primers for use in the generation of larger synthetic fragment.

A preferred functional derivative is a fusion protein, a polypeptide that includes a functional fragment of B7-DC. For example, a useful derivative of B7 is a B7-DC-Ig fusion protein that comprises a polypeptide corresponding to the ECD of B7-DC and an Ig C region. The presence of the fusion partner can alter the solubility, affinity and/or valency (defined here as the number of binding sites available per molecule) of the B7-DC protein. A soluble B7-DC fusion protein, while still binding to a receptor on T cells, may have a different biological effect than of the native protein expressed on an APC, i.e., inhibition of T cell stimulation by competitive binding rather than costimulation.

As used herein an extracellular domain (ECD) of B7-DC is the entire extracellular portion of the protein or any fragment thereof that recognizes and binds to PD-1 or to another receptor on T cells that is not CD28 or CTLA-4. Preferably, an ECD of B7-DC is that portion encoded by amino acid residues from about position 26 to about position 221 of SEQ ID NO:2 or SEQ ID NO:4.

By "soluble B7-DC" is intended a cell-free form of B7-DC that may be shed, secreted or otherwise extracted from the producing cells. Soluble B7-DC includes, but is not limited to, soluble fusion proteins such as B7-DC-Ig, free ECD of B7-DC, or the B7-DC ECD fused (genetically or chemically) to a biologically active molecule.

As indicated earlier, this invention also includes hybrid fusion proteins between a B7-DC domain and a domain or fragment of another B7 family protein, preferably expressed on the cell surface in costimulatory form.

A preferred group of B7-DC variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the B7-DC protein in terms of its T cell costimulatory activity. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the B7-DC polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

Chemical Derivatives of B7-DC

"Chemical derivatives" of B7-DC contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences*, 16*th* ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Also included are peptides wherein one or more D-amino acids are substituted for one or more L-amino acids.

Multimeric Peptides

The present invention also includes longer polypeptides in which a basic peptidic sequence obtained from the sequence of B7-DC is repeated from about two to about 100 is times, with or without intervening spacers or linkers. It is understood that such multimers may be built from any of the peptide variants defined herein. Moreover, a peptide multimer may comprise different combinations of peptide monomers and the disclosed substitution variants thereof. Such oligomeric or multimeric peptides can be made by chemical synthesis or by recombinant DNA techniques as discussed herein. When produced chemically, the oligomers preferably have from 2-8 repeats of the basic peptide sequence. When produced recombinantly, the multimers may have as many repeats as the expression system permits, for example from two to about 100 repeats.

In tandem multimers, preferably dimers and trimers, of the B7-DC peptide or polypeptide, the chains bonded by interchain disulfide bonds or other "artificial" covalent bonds between the chains such that the chains are "side-by-side" rather than "end to end." Preferred dimers and trimers are those between fusion proteins of B7-DC such as B7-DC-Ig, as described herein.

Antibodies Specific for Epitopes of B7-DC

In the following description, reference will be made to various methodologies known to those of skill in the art of immunology, cell biology, and molecular biology. Publications and other materials setting forth such known methodologies to which reference is made are incorporated herein by reference in their entireties as though set forth in fall. Standard reference works setting forth the general principles of immunology include A. K. Abbas et al., *Cellular and Molecular Immunology* (Fourth Ed.), W.B. Saunders Co., Philadelphia, 2000; C. A. Janeway et al, *Immunobiology. The Immune System in Health and Disease*, Fourth ed., Garland Publishing Co., New York, 1999; Roitt, I. et al., *Immunology*, (current ed.) C. V. Mosby Co., St. Louis, Mo. (1999); Klein, J., *Immunology*, Blackwell Scientific Publications, Inc., Cambridge, Mass., (1990).

Monoclonal antibodies (mAbs) and methods for their production and use are described in Kohler and Milstein, *Nature* 256:495-497 (1975); U.S. Pat. No. 4,376,110; Hartlow, E. et al., *Antibodies: A Laboratory Manual*, Cold Spring Harbor Laboratory Press, Cold Spring Harbor, N.Y., 1988); *Monoclonal Antibodies and Hybridomas: A New Dimension in Biological Analyses*, Plenum Press, New York, N.Y. (1980); H. Zola et al., in *Monoclonal Hybridoma Antibodies: Techniques and Applications*, CRC Press, 1982)).

Immunoassay methods are also described in Coligan, J. E. et al., eds., *Current Protocols in Immunology*, Wiley-Interscience, New York 1991 (or current edition); Butt, W. R. (ed.) *Practical Immunoassay: The State of the Art*, Dekker, New York, 1984; Bizollon, Ch. A., ed., *Monoclonal Antibodies and New Trends in Immunoassays*, Elsevier, N.Y., 1984; Butler, J. E., ELISA (Chapter 29), In: van Oss, C. J. et al., (eds), *IMMUNOCHEMISTRY*, Marcel Dekker, Inc., New York, 1994, pp. 759-803; Butler, J. E. (ed.), *Immunochemistry of Solid-Phase Immunoassay*, CRC Press, Boca Raton, 1991; Weintraub, B., *Principles of Radioimmunoassays*, Seventh Training Course on Radioligand Assay Techniques, The Endocrine Society, March, 1986; Work, T. S. et al, *Laboratory Techniques and Biochemistry in Molecular Biology*, North Holland Publishing Company, NY, (1978) (Chapter by Chard, T., "An Introduction to Radioimmune Assay and Related Techniques").

Anti-idiotypic antibodies are described, for example, in *Idiotypy in Biology and Medicine*, Academic Press, New York, 1984; *Immunological Reviews Volume* 79, 1984; *Immunological Reviews* Volume 90, 1986; *Curr. Top. Microbiol., Immunol.* Volume 119, 1985; Bona, C. et al., *CRC Crit. Rev. Immunol*, pp. 33-81 (1981); Jerne, N K, *Ann. Immunol*. 125C: 373-389 (1974); Jerne, N K, In: *Idiotypes—Antigens on the Inside*, Westen-Schnurr, I., ed., Editiones Roche, Basel, 1982, Urbain, J et al., *Ann. Immunol.* 133D:179-(1982); Rajewsky, K. et al., *Ann. Rev. Immunol* 1:569-607 (1983)

The present invention provides antibodies, both polyclonal and monoclonal, reactive with novel epitopes of B7-DC that are absent from known B7 family proteins. The antibodies may be xenogeneic, allogeneic, syngeneic, or modified forms thereof, such as humanized or chimeric antibodies. Antiidiotypic antibodies specific for the idiotype of an anti-B7-DC antibody are also included. The term "antibody" is also meant to include both intact molecules as well as fragments thereof that include the antigen-binding site and are capable of binding to a B7-DC epitope. These include, Fab and F(ab')$_2$ fragments which lack the Fc fragment of an intact antibody, clear more rapidly from the circulation, and may have less non-specific tissue binding than an intact antibody (Wah et al., *J. Nucl. Med.* 24:316-325 (1983)). Also included are Fv fragments (Hochman, J. et al. (1973) *Biochemistry* 12:1130-1135; Sharon, J. et al. (1976) Biochemistry 15:1591-1594).).

These various fragments are be produced using conventional techniques such as protease cleavage or chemical cleavage (see, e.g., Rousseaux et al., *Meth. Enzymol.*, 121:663-69 (1986))

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography (see Zola et al., supra).

The immunogen may comprise the complete B7-D6 protein, or fragments or derivatives thereof. Preferred immunogens comprise all or a part of the ECD of human B7-DC (amino acid residues 26-221), where these residues contain the post-translation modifications, such as glycosylation, found on the native B7-DC. Immunogens comprising the extracellular domain are produced in a variety of ways known in the art, e.g., expression of cloned genes using conventional recombinant methods, isolation from cells of origin, cell populations expressing high levels of B7-DC, etc.

The mAbs may be produced using conventional hybridoma technology, such as the procedures introduced by Kohler and Milstein (*Nature*, 256:495-97 (1975)),—and modifications thereof (see above references). An animal, preferably a mouse is primed by immunization with an immunogen as above to elicit the desired antibody response in the primed animal.

B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques using the B7-DC-Ig fusion protein Positive clones are subcloned, e.g., by limiting dilution, and the mAbs are isolated.

Hybridomas produced according to these methods can be propagated in vitro or in vivo (in ascites fluid) using techniques known in the art (see generally Fink et al., *Prog. Clin. Pathol.*, 9:121-33 (1984)). Generally, the individual cell line is propagated in culture and the culture medium containing high concentrations of a single mnAb can be harvested by decantation, filtration, or centrifugation.

The antibody may be produced as a single chain antibody or scFv instead of the normal multimeric structure. Single chain antibodies include the hypervariable regions from an Ig of interest and recreate the antigen binding site of the native Ig while being a fraction of the size of the intact Ig (Skerra, A. et al. (1988) *Science*, 240: 1038-1041; Pluckthun, A. et al. (1989) *Methods Enzymol.* 178; 497-515; Winter, G. et al. (1991) *Nature*, 349: 293-299); Bird et al. (1988) *Science* 242:423; Huston et al. (1988) *Proc. Natl. Acad. Sci. USA* 85:5879; Jost C R et al., *J Biol Chem.* 1994 269:26267-26273; U.S. Pat. Nos. 4,704,692, 4,853,871, 4,94,6778, 5,260,203, 5,455,0Kn contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen.

In another type of "sandwich" assay the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The foregoing antibodies are useful in method for inhibiting T cell stimulation and treating diseases associated with undesired T cell activation, such as transplant rejection and autoimmunity. This method involves administering a subject in need of such treatment an effective amount of an antibody, preferably a mAb, more preferably a human or humanized mAb specific for a costimulatory epitope of B7-DC. The administration of antibody must be effective in blocking stimulation of T cells or in eliminating antigen-reactive T cells, thereby inhibiting the targeted T cell response. Relevant dose ranges are described below.

Uses of Nucleic Acids that Encode B7-DC Protein

The nucleic acids of this invention are used diagnostically to monitor the progress of a disease, by measuring the expression of B7-DC in cells from biological samples or for assaying the effect of an agent on the expression of B7-DC. This is preferably accomplished by measurement of cellular mRNA levels. For use in such diagnostic methods, the nucleic acid sequence is detectably labeled, e.g., with a radioactive or fluorescent label or biotin and used in a conventional dot blot or Northern hybridization procedure to probe mRNA molecules present in, for example, a preparation of total kor poly(A+) RNA from a biological sample.

Therapeutic Compositions and their Administration

The B7-DC polypeptide or a cell expressing this polypeptide such as a DC or a tumor cell is administered to a mammalian subject, preferably a human. Cell-associated, immobilized or otherwise aggregated forms of the polypeptide are used to enhance T lymphocyte reactivity and the resultant immunity. The B7-DC-Ig fusion protein assembles as a dimer and, as shown in the examples, co-stimulates T cells. Soluble monomeric forms of the B7-DC polypeptide can bind to the receptor on T cells without stimulating activity and can therefore be considered competitive inhibitors or antagonists of T cell co-stimulation by a stimulatory form of the molecule. Binding of a such a B7-DC antagonist may suppress ongoing T cell reactivity or may interfere with the effect of a costimulatory signal presented by endogenous B7-DC or even by other B7 family members acting via their receptors (e.g., CD28 or CTLA-4).

A composition having the activity of B7-DC as described herein is administered in a pharmaceutically acceptable carrier in a biologically effective or a therapeutically effective amount. The B7-DC polypeptide (or cell expressing the polypeptide) may be given alone or in combination with another protein or peptide such as one having the activity of another member of the B7 family or another immunostimulatory molecule Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

The following doses and amounts also pertain to the antibodies of the invention when administered to a subject.

A therapeutically effective amount is a dosage that, when given for an effective period of time, achieves the desired immunological or clinical effect.

A therapeutically active amount of a polypeptide having B7-DC activity (or an anti-B7-DC antibody) may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 ng and about 1 gram per kilogram of body weight of the recipient, more preferably between about 1 µg and 100 mg/kg, more preferably, between about 100 µg and about 100 mg/kg. Dosage forms suitable for internal administration preferably contain (for the latter dose range) from about 0.1 mg to 500 mg of active ingredient per unit. The active ingredient may vary from 0.5 to 95% by weight based on the total weight of the composition. Alternatively, an effective dose of cells expressing B7-DC, such preferably transduced cells such as DC's or inactivated tumor cells, is between about $10^4$ and $10^9$ cells, more preferably between about $10^6$ and $10^8$ cells per subject, preferably in split doses. Those skilled in the art of immunotherapy will be able to adjust these doses without undue experimentation.

The active compound (e.g., B7-DC polypeptide or cell transduced with B7-DC DNA) may be administered in a convenient manner, e.g., injection by a convenient and effective route. Preferred routes include subcutaneous, intradermal, intravenous and intramuscular routes. Other possible routes include oral administration, intrathecal, inhalation, transdermal application, or rectal administration. For the treatment of tumors which have not been completely resected, direct intratumoral injection is also intended.

Depending on the route of administration, the active compound may be coated in a material to protect the compound from the action of enzymes, acids and other natural conditions which may inactivate the compound. Thus, to a administer a polypeptide or peptide having B7-DC activity by an enteral route, it may be necessary to coat the composition with, or co-administer the composition with, a material to prevent its inactivation. For example, a peptide may be administered to an individual in an appropriate carrier, diluent or adjuvant, co-administered with enzyme inhibitors (e.g., pancreatic trypsin inhibitor, diisopropylfluorophosphate (DEP) and trasylol) or in an appropriate carrier such as liposomes (including water-in-oil-in-water emulsions as well as conventional liposomes (Strejan et al., (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chorobutanol, phenol, ascorbic acid, thimerosal, and the like.

Prolonged absorption of the injectable compositions can be brought about by including in the composition an agent which delays absorption, for example, aluminum monostearate and gelatin.

Parenteral compositions are preferably formulated in dosage unit form for case of administration and uniformity of dosage. Dosage unit form refers to physically discrete units suited as unitary dosages for a mammalian subject; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the proteins of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

Other pharmaceutically acceptable carriers for the B7-DC polypeptide according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Modification of Tumor Cells to Express B7-DC and Multiple Costimulatory Molecules Another aspect of the invention is a cell, preferably a tumor cell, modified to express multiple costimulatory molecules. The temporal expression of costimulatory molecules on activated B cells is different for B7, B7-2 and B7-3. For example, B7-2 is expressed early following B cell activation, whereas B7-3 is expressed later. The different costimulatory molecules may thus serve distinct functions during the course of an immune response. An effective T cell response may require that the T cell receive costimulatory signals from multiple costimulatory molecules.

Accordingly, the invention encompasses a tumor cell which is genetically modified or to express more than one costimulatory molecule. For example, a tumor cell can be modified to express B7-DC and one or more of B7, B7-2 and B7-3.

Before modification, a cell such as a tumor cell may not express any costimulatory molecules, or may express certain costimulatory molecules but not others. As described herein, tumor cells can be modified by transfection with nucleic acid encoding B7-DC alone or with another costimulatory molecule(s). For example, a tumor cell transfected with nucleic acid encoding B7-DC can be further transfected with nucleic acid encoding B7. The sequence of cDNA molecules encoding human or mouse B7-DC proteins are SEQ ID NO:1 and the coding portion of SEQ ID NO:3, respectively. Alternatively, more than one type of modification can be used. For example, a tumor cell transfected with a nucleic acid encoding B7-DC can be stimulated 0 with an agent which induces expression of B7-1, B7-2 or B7-3.

Antigens Associated with Pathogens

A major utility for the present invention is the use of the present compositions in therapeutic vaccine for cancer and for major chronic viral infections that cause morbidity and mortality worldwide. Such vaccines are designed to eliminate infected cells—this requires T cell responses as antibodies are ineffective. The vaccines of the present invention, include, in addition to the antigenic epitope itself:

(a) a vector such as naked DNA, naked RNA, self replicating RNA replicons and viruses including vaccinia, adenoviruses, adeno-associaged virus (AAV), lentiviruses and RNA alphaviruses;

(b) an antigen targeting or processing signal such as HSP70, calreticulin, the extracellular domain of Flt-3 ligand, domain II of *Pseudomonas* exotoxin ETA, herpes simplex VP22 targeting protein, and the like. (See commonly assigned U.S. patent application Ser. Nos. 09/421,608; 09/501,097; 09/693,450; 60/222,9002; 60/222,985; 60/268,575 and Chang, W-F et al., J. Virol. 75:2368-2376 (2001), which are hereby incorporated by reference in their entirety); and (c) a costimulatory signal, preferably the B7-DC protein of the present invention or a fusion protein, fragment or functional derivative thereof (alone or in combination with other known costimulatory proteins such as B7.1, B7.2, soluble CD40, etc.).

Tumor cells or other types of host cells, including APCs, are transformed, transfected or otherwise transduced with a nucleic encoding an antigen to which an immune response is desired. Such antigens are preferably epitopes of pathogenic microorganisms against which the host is defended by effector T cells responses, including cytotoxic T lymphocyte (CTL) and delayed type hypersensitivity. These typically include viruses, intracellular parasites such as malaria, and bacteria that grow intracellularly such as mycobacteria and *listeria*. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus (HBV) (Beasley, R. P. et al., *Lancet* 2, 1129-1133 (1981) has been implicated as etiologic agent of hepatomas. 80-90% of cervical cancers express the E6 and E7 antigens from one of four "high risk" human papillomavirus types: HPV-16, HPV-18, HPV-31 and HPV-45 (Gissmann, L. et al., *Ciba Found Symp.* 120, 190-207 (1986); Beaudenon, S., et al. *Nature* 321, 246-249 (1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic BV vaccines in Asia have decreased the incidence of hepatoma (Chang, M. H., et al *New Engl. J. Med.* 336, 1855-1859 (1997), representing a great impact on cancer prevention.

Among the most important viruses in chronic human viral infections are human papillomavirus (HPV) hepatitis B virus (HBV), hepatitis C Virus (HCV), human immunodeficiency virus (HIV), Epstein Barr Virus (EBV) and herpes simplex virus (HSV).

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine herpesviruses, Marek's disease virus in chickens and other fowl; animal retroviral diseases; pseudorabies and rabies and the like.

The following references set forth principles and current information in the field of basic, medical and veterinary virology and are incorporated by reference: *Fields Virology*, Fields, B N et at, eds., Lippincott Williams & Wilkins, NY, 1996; *Principles of Virology: Molecular Biology, Pathogenesis, and Control*, Flint, S. J. et al., eds., Amer Society for Microbiology, Washington, 1999; *Principles and Practice of*

*Clinical Virology*, 4th Edition, Zuckerman. A. J. et al., eds., John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control*, Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regemnortel, M H V et al., eds., Academic Press; NY, 2000.

Targeting Molecules

A number of proteins that have various modes of action have been implicated as "targeting" molecules to be used in conjunction with antigens, preferably as fusion polypeptides, to target the antigen to cells and subcellular compartments that promote presentation of the antigen to T cells in a more potent and effective manner.

Linkage of antigens to heat shock proteins (HSPs) represents a potential approach for increasing the potency of nucleic acid-based (and other) vaccines. HSPs appear to acct as natural biologic adjuvants in cancer and viral vaccination. Both the gp96 HSP resident in the endoplasmic reticulum (ER) and the cytosolic Hsp70 act as immunologic adjuvants (Srivastava, P K et al., *Semin. Immunol* 3, 57-64 (1991); Udono, H et al., *Proc. Natl. Acad. Sci. USA* 91, 3077-3081 (1994)). These HSPs, or chaperonins, bind a wide array of peptides (Lammert, E., et al., *Eur. J. Immunol.* 27, 923-927 (1997)). Hsp70 is a chaperonin that can target associated proteins to the proteosome—the primary cellular protease complex that generates peptides for association with MHC class I molecules. Therefore, antigens directly linked to Hsp70 are more efficiently presented by MHC class I (leading, inter alia, to CTL responses). Two features appear to be responsible for HSP adjuvanticity: (1) in vitro, peptide loaded gp96 effectively introduce antigens into the MHC class I processing pathway; (2) binding of gp96 to macrophages induces secretion of proinflammatory cytokines, thus augmenting the function of the cells to which the peptide antigen has been targeted.

Immunization with HSP complexes isolated from tumor or from virus-infected cells induces potent antitumor immunity (Srivastava, P K et al., *Int J. Cancer.* 33: 417-22, 1984; Srivastava, P K et al., *Proc Natl Acad Sci USA.* 83: 3407-11, 1986; Udono, H et al., *J Immunol.* 152: 5398-5403, 1994; Blachere, N E et al., *J Immunother.* 14: 352-6, 1993; Udono, H et al, supra; Tamura, Y et al., *Science.* 278: 117-20, 1997; Janetzki, S et al., *J Immunother.* 21: 269-76, 1998)) or antiviral immunity (Heikema, A et al., *Immunol Lett* 57: 69-74, 1997; Suto, R et al., *Science.* 269: 1585-8, 1995). Mixing peptides with HSPs in vitro generated immunogenic HSP-peptide complexes (Ciuputi, A M et al., *J Exp Med.* 187: 685-91, 1998; Blachere, N E et al., *J Exp Med.* 186: 1315-22, 1997). Some HSP-based protein vaccines involved fusion of the antigen to the HSP (Suzue, K et al, *J Immunol* 156: 873-9, 1996; Suzue, K. et al., *Proc Natl. Acad Sci USA* 94: 13146-51, 1997). More recently, the present inventors and their colleagues (e.g., Chen, C-H et al., *Canc. Res.* 60:1035-1042 (2000)) used HSPs in the form of chimeric DNA or RNA replicon vaccines. They used HPV-16 E7 as antigen fused to *Mycobacterium tuberculosis* HSP70 and showed increased expansion and activation of E7-specific CD8+ T cells which resulted in potent antitumor immunity against established tumors (Lin, K.-Y. et al., *Cancer Res.* 56: 21-26., 1996).

Another useful targeting molecule is the translocation domain of a *Pseudomonas* exotoxin A (ETA), e.g., domain II (dII) of ETA (spanning residues 253-364). A translocation domain is a polypeptide that induces translocation of protein or polypeptide to which it is linked into the cytosol of a cell. For example, similarly applicable polypeptide are derived from a *Diphtheria, Clostridia* (*botulinum, tetani*), Anthrax, *Yersinia, Vibrio cholerae*, or *Bordetella pertussis* toxin. The toxic domain of the DNA encoding the toxin is preferably mutated or deleted in the preparation of such compositions.

Calreticulin (CRT) is an abundant 46 kDa protein located in the endoplasmic reticulum (ER) lumen that displays lectin activity and is known to be involved in the folding and assembly of nascent glycoproteins (Nash (1994) *Mol. Cell. Biochem.* 135:71-78; Hebert (1997) *J. Cell Biol* 139:613-623; Vassilakos (1998) *Biochemistry* 37:3480-3490; Spiro (1996) *J. Biol. Chem.* 271:11588-11594. CRT associates with peptides transported into the ER by transporters associated with antigen processing, such as TAP-1 and TAP-2 (Spee (1997) *Eur. J. Immunol.* 27:2441-2449). CRT forms complexes in vitro with peptides. These complexes, when administered to mice, elicited peptide-specific CD8+ T cell responses (B asu (1999) *J. Exp. Med.* 189:797-802; Nair (1999) *J. Immunol* 162:6426-6432). CRT purified from mouse tumors elicited immunity specific to the tumor used as the source of CRT, but not to an antigenically distinct tumor (Basu, supra). By pulsing DCs in vitro with a CRT bound to a peptide, the peptide was re-presented in the context of DC Class I molecules and stimulated peptide-specific CTLs (air, supra).

The Flt-3 ligand stimulates growth of DC precursors and can promote generation of large numbers of DCs in vivo (Maraskovsky, E. et al., *J Exp Med.* 184: 1953-62, 1996; Shurin, M R. et al., *Cell Immunol.* 179: 174-84, 1997). Flt3, a murine tyrosine kinase receptor (Rosnet, O. et al. *Oncogene* 6: 1641-50, 1991) is a member of the III receptor kinase family (for review see Lyman, S D, *Curr Opin Hematol* 5: 192-6, 1998). In hematopoietic tissues, the expression of Flt3 is restricted to the CD34-positive progenitors. Flt3 was used to identify and subsequently clone the corresponding ligand, Flt3-ligand (Lyman, S D et al., *Cell* 75: 1157-67, 1993; Hannum, C et al., *Nature* 368: 643-8, 1994). The predominant form of Flt3-ligand is synthesized as a transmembrane protein from which the functionally similar soluble ECD is generated by proteolytic cleavage (Lyman et al., supra). These proteins bind to and activating unique tyrosine kinase receptors. Among hematopoietic cells, expression of the Flt3 receptor is primarily restricted to the most primitive progenitor cells, including DC precursors. The ECD of Flt3-ligand generated strong anti-tumor effects against several murine model tumors including fibrosarcoma, breast cancer, liver cancer, lung cancer, melanoma and lymphoma (Lynch, D H et al, *Nat. Med.* 3: 625-631, 1997; Chen, K et al., *Cancer Res.* 57: 3511-3516, 1997; Braun, S E et al., *Hum Gene Ther.* 10: 2141-2151, 1999; Peron, J M et al., *J Immunol.* 161: 6164-6170, 1998; Chakravarty, P K et al., *Cancer Res.* 59: 6028-6032, 1999; Esche, C et al, *Cancer Res.* 58: 380-383, 1998.) (19). The present inventors' colleagues linked DNA encoding BPV Ek7 protein to DNA encoding Flt3-ligand ECD. Immunization with this construct dramatically increased expansion and activation of E7 antigen-specific CD8+ T cells, resulting in potent anti-tumor immunity against established E7-expressing metastatic tumors.

The HSV-1 protein VP22 is a prototype protein that contributes, among other things, to enhanced spread of antigen due to its remarkable property of intercellular transport (Elliott, G., and P. O'Hare. 1997. *Cell* 88:223-33) can be used. For example, VP22 linked to p53 (Phelan, A. et al., 1998, *Nat Biotechnol* 16:440-443) or thymidine kinase (Dilber, M S et al., 1999, *Gene Ther* 6:12-21), facilitated the spread of linked protein to surrounding cells in vitro and the treatment of model tumors. VP22 linked to HPV-16 E7 antigen in the context of a DNA vaccine led to a dramatic increase in the number of E7-specific CD8+ T cell precursors in vaccinated mice (around 50-fold) and converted a less effective DNA vaccine into one with significant potency against E7-expressing tumors. Anon-spreading VP22 mutant failed to enhance vaccine potency. VP22 and proteins that may have a similar mode of action, contribute in several ways to enhanced vaccine potency: (1) facilitate spreading of antigen from transfected cells to surrounding APCs, thereby increasing the number of APCs that present antigen through MAC class I pathway; (2) present antigen more efficiently in transfected cells (3) carryout "cross-priming" whereby release of a VP22/antigen fusion protein leads to uptake and processing by DCs (or other APCs) for presentation via the MHC-I restricted pathway (Huang, A Y et al., 1994, *Science* 264:961-965)

Those skilled in the art will know how to identify appropriate epitopes, e.g., CTL epitopes, of the relevant proteins from the pathogens for use in accordance with this invention.

Delivery of B7-DC DNA to Cells an Animals

DNA delivery, for example to effect what is generally known as "gene therapy" involves introduction of a "foreign" DNA into a cell and ultimately, into a live animal. Several general strategies for gene therapy have been studied and have been reviewed extensively (Yang, N-S., *Crit. Rev. Biotechnol.* 12:335-356 (1992); Anderson, W. F., *Science* 256: 808-813 (1992); Miller, A. S., *Nature* 357:455-460 (1992); Crystal, R. G., *Amer. J. Med.* 92(suppl 6A):44S-52S (1992); Zwiebel, J. A. et al., *Ann. N.Y. Acad. Sci.* 618:394-404 (1991); McLachlin, J. R. et al., *Prog. Nuctl Acid Res. Molec. Biol.* 38:91-135 (1990); Kohn, D. B. et al., *Cancer Invest.* 7:179-192 (1989), which references are herein incorporated by reference in their entirety).

One approach comprises nucleic acid transfer into primary cells in culture followed by autologous transplantation of the ex vivo transformed cells into the host, either systemically or into a particular organ or tissue.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the B7-DC expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a 0"carrier".

Examples of successful "gene transfer" reported in the art include: (a) direct injection of plasmid DNA into mouse muscle tissues, which led to expression of marker genes for an indefinite period of time (Wolff, J. A. et al., *Science* 247:1465 (1990); Acsadi, G. et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M. A. et al., *Science* 252: 431 (1991); (e) Herpes simplex virus vectors achieved in vivo gene transfer into brain tissue (Almad, F. et al., eds, *Miami Short Reports—Advances in Gene Technology: The Molecular Biology of Human Genetic Disease*, Vol 1, Boerringer Manneheim Biochemicals, USA, 1991).

Retroviral-mediated human therapy utilizes amphotrophic, replication-deficient retrovirus systems (Temin, H. M., *Human Gene Therapy* 1: 111 (1990); Temin et al., U.S. Pat. No. 4,980,289; Temin et al., U.S. Pat. No. 4,650, 764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al, *Mol. Cell. Biol.* 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the B7-DC sequences may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al, *Molec. Cell. Biol.* 5:431-437 (1985); Sorge, J., et al., *Molec. Cell. Biol* 4:1730-1737 (1984); Hock, R. A. et al., *Nature* 320:257 (1986); Miller, A. D. et al., *Molec. Cell. Biol.* 6:2895-2902 (1986). Newer packaging cell lines which are efficient an safe for gene transfer have also been described (Bank et al, U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: *Virology, Fields*, B N et al., eds, Raven Press, New York, 1990, p. 1679; Berkner, K. L., *Biotechniques* 6:616 9191988), Strauss, S. E., In: *The Adenoviruses*, Ginsberg, H S, ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., *EMBO J.* 10:3941 (1991) according to the present invention.

Another vector which can express the DNA molecule of the presen invention, and is useful in the present therapeutic setting, particularly in humans, is vaccinia virus, which can be rendered non-replicating (U.S. Pat. Nos. 5,225,336; 5,204, 243; 5,155,020; 4,769,330; Sutter, G e al., *Proc. Natl. Acad. Sci. USA* (I 992) 89:10847-10851; Fuerst, T. R. et al., *Proc. Nail. Acad. Sci. USA* (1989) 86:2549-2553; Falkner F. G. et al.; *Nucl. Acids Res* (1987) 15:7192; Chakrabarti, S et al.,

*Molec. Cell. Biol.* (1985) 5:3403-3409). Descriptions of recombinant vaccinia viruses and other viruses containing heterologous DNA and their uses in immunization and DNA therapy are reviewed in: Moss, B., *Curr. Opin. Genet. Dev.* (1993) 3:86-90; Moss, B. *Biotechnology* (1992) 20: 345-362; Moss, B., *Curr Top Microbiol Immunol* (1992) 158:25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to naked DNA or RNA, or viral vectors, engineered bacteria may be used as vectors. A number of bacterial strains including *Salmonella*, BCG and *Listeria monocytogenes*(LM) (Hoiseth & Stocker, *Nature* 291, 238-239 (1981); Poirier, T P et al. *J. Exp. Med.* 168, 25-32 (1988); (Sadoff, J. C., et al., *Science* 240, 336-338 (1988); Stover, C. K., et al., *Nature* 351, 456-460 (1991); Aldovini, A. et al., *Nature* 351, 479-482 (1991); Schafer, R., et al., *J. Immunol.* 149, 53-59 (1992); Ikonomidis, G. et al., *J. Exp. Med.* 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al, *FEBS Lett.* 280:94 (1991); Zelenin, A. V. et al., *FEDS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088:131 ((1991)).

"Carrier mediated gene transfer" has also been described (Wu, C. H. et al., *J. Biol. Chem.* 264-16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immuno-liposomes, which can incorporate acylated mAbs into the lipid bilayer (Wang et al, supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Again, as noted above, for the utility of transduced B7-DC molecules according to this invention may not require stable expression. Rather, transient expression of the polypeptide may be sufficient for transduced cells to perform their immunogenic and/or costimulatory function.

Having now generally described the invention, the same will be more readily understood through reference to the following examples which are provided by way of illustration, and are not intended to be limiting of the present invention, unless specified.

Example I

Materials and Methods

Cell Preparation and Culture 6-12 week old female BALB/c mice were purchased from NCI and used for DC and macrophage preparation.

Bone marrow-derived DCs were cultured in RPMI1640 (Gibco BRL) medium supplemented with 5% fetal calf serum (FCS) (Hyclone), Penicillin/Streptomycin (JRH Biosciences), Gentamycin (Sigma), Nonessential amino acids (JRH Biosciences), L-Glutamate (JHR Biosciences), Sodium Pyruvate (Sigma), 2 mercaptoethanol (Sigma) and 1000 units/ml recombinant murine GM-CSP (Immunex) as previously described (26). Day 8 bone marrow-derived DCs were stained with monoclonal antibodies by conventional methods. Monoclonal antibody against MHC class II 14-4-4s, was purified from hybridoma supernatant. Dr. William Baldwin, Johns Hopkins University, kindly supplied CTLA4-Ig fusion molecule. Antibodies for MAC class I (28-14-8), F4/80 (C1.A3-1), B7.1 (1G10), B7.2 (GL1), FcγRII/II (2.4 G2) and Mac-1 (M1/70) were purchased from PharMingen, For tester cDNA preparation, day 8 cells were purified by cell sorter using 14-4-4-s and CTLA4-Ig at the Johns Hopkins University Oncology Center. The purity of MAC class II$^{hi}$ and B7$^{hi}$ population after sorting was 93-98%.

Bone marrow-derived macrophages were cultured with RPMI-1640 medium supplemented with 10% FCS, Penicillin/Streptomycin, non-essential amino acids, sodium pyruvate, L glutamine, 2-mercaptoethanol and 250 units/ml recombinant murine M-CSF, and they were treated with 500 units/ml γ-IFN (Pharmingen) and 5 μg/ml LPS (Sigma) as previously described (27). After stimulation, cell surface expression of MHC class II and B7 were confirmed using flow cytometric analysis on day 10 of culture.

Macrophage cell lines WEHI-3, RAW264.7, J774.A.1, PU5-1.8 were kindly provided by Dr. Joshua Farber of the NIAID, National Institutes of Health. They were cultured with ATCC recommended medium.

Allogeneic Mixed Lymphocyte Reaction

Day 8 BM-derived DCs characterized as MHC class II$^{hi}$ and B7$^{hi}$ were tested for their ability to stimulate allogeneic T cells in MLC. MLC reactions were performed in 96 well flat bottom microplates by adding increasing number of BALD/c stimulator cells s to 3×10$^5$ allogeneic C57BL/6 lymphocytes. After 3 days of culture, T cell proliferation was assessed by addition of 1 μCi of [$^3$H]-methyl-thymidine (Amersham) to each well for the final 18 h of culture. Cells were then harvested, and incorporation of radioactivity was determined using a β counter (Packard 96).

cDNA Subtractive Hybridization

Total RNA from sorted DCs and activated macrophages was extracted with TRIZOL (Gibco BRL). Messenger RNA was purified by Oligotex mRNA purification kit (Qiagen). We used the PCR based SMART cDNA synthesis system (Clonetech) to amplify cDNA followed by the PCR based subtraction system PCR Select (Clonetech). Subtraction was performed following the manufacturer's protocol. After final subtractive PCR, DNA fragments were ligated into plasmid vectors pCR2.1 (Invitrogen) or pCR Blunt (Invitrogen). After transformation, each clone was grown for plasmid DNA amplification and miniprep DNA and then digested with EcoRI to confirm the presence of inserts. Plasmid dot blot was then performed to confirm that the cDNA cloned is dendritic cell specific. Alkaline denatured miniprep DNAs were spotted on Hybond N+ membrane (Amersham) and hybridized with SMART cDNA probe-derived from sorted DCs or activated macrophages. These cDNA probes were $^{32}$P labeled using random primer labeling method (Stratagene Prime-It II). Hybridizations and washing were done as previously described(28). Membranes were exposed to a film (Amersham) for 1-2 days and developed.

Plasmid Dot Blot Analysis

Alkaline denatured miniprep DNA samples were spotted on Hybond N+membrane (Amersham) and hybridized with SMART® cDNA probe-derived from sorted DCs or activated macrophages. These cDNA probes were $^{32}$P labeled using a random primer labeling method (Stratagene Prime-It II). Hybridizations and washing were done as previously described [cites??]. For autoradiography, membranes were exposed to a film (Amersham) for 1-2 days and developed.

cDNA Library Construction and Screening—Cloning of B7-DC

Bone marrow-derived DCs were harvested on day 8 without sorting. About 20% to 40% of these cells expressed high MHC class II and B7. Total RNA extraction followed by poly A RNA purification was done as described above. For oligo dT primed DC library construction, we used Lambda ZAP Express cDNA synthesis system (Stratagene). The PCR DNA fragment of B7-DC was probed and used for screening. Membrane transfer, denaturation, renaturation, were performed using Stratagene's protocol. Radiolabeling of probes, hybridization, washing, and autoradiography were done as described above. Positive clones were isolated and 2nd screening was performed. After 2nd screening, plasmids were excised by in vivo excision and tested by dot blotting and sequencing. Sequencing was done by the Core Facility at the Johns Hopkins University School of Medicine. BLAST program was used to do homology search of the nucleotide sequence against Genbank (NCBI) for similarity to previously reported genes. The full length B7-DC cDNA clone was pulled out from the DC cDNA library. 5' RACE was performed suing SMART RACE cDNA amplification kit (Clontech). 5'-RACE products were cloned into pC2.1 vector and sequenced. Two more full length B7-DC clones were obtained by RT-PCR and their sequence were compared to avoid sequence error.

Human B7-DC was cloned as follows: human DCs were obtained from normal peripheral blood mononuclear cells by culture in either GM-CSF+IL-4 or GM-CSF+Flt-3L as described previously(29). RNA was extracted as described above. A BLAST search identified an overlapping EST clone, GenBank accession number AK001879, with homology to mouse B7-DC. 5' RACE was performed as described above. We sequenced a 5'-RACE PCR fragment and designed a primer corresponding to 5'-UTR of human B7DC. The following primers in the 5'-UTR and 3'-UTR of B7-DC was used to amplify full-length human B7-DC:

5'-GGAGCTACTGCATGTTGATTGTTTTG-3'   [SEQ ID NO: 6]
and

5'-TGCAAACTGAGGCACTGAAAAGTC-3'   [SEQ ID NO: 7]

The fall length cDNA sequences of the human and murine B7-DC cDNAs have been deposited with EMBL/GenBank/DDBS under accession number AF329193 and AF142780.

BAC (129SVJ) Library Screening/Genomic Cloning and Mapping

BAC library screening, followed manufacturer's protocol (Genome Systems, Inc.)

Primers Used:

5'-TTGTTGTCTCCTTCTGTCTCCCAAC-3'   [SEQ ID NO: 8]
and

5'-ACAGTTGCTCCTTGTATCAGGTTC-3'   [SEQ ID NO: 9]

BAC library screening obtained 3 positive clones. Chromosome location mapping was done by fluorescence in situ hybridization (Genome Systems Inc.). A total of 80 metaphase cells were analyzed with 79 exhibiting specific labeling. The human B7-DC mapping was done by using available bioinformatic tools, NCBI's BLAST program and the International RH Mapping Consortium. The hB7-DC sequence was searched in htsg and was found to map to two BAC clones RP11-574F11 (AL162253) and Rp11-635N21 (AL354744) localizing on chromosome 9.

Virtual Northern Blotting 4-6 weeks old female Balb/c mice were purchased from NCI and used for tissue RNA preparation. RNA extraction and SMART cDNA synthesis for tissues, sorted DCs and activated macrophages were performed as described above. SMART PCR cDNAs were purified by PCR purification kit (Qiagen). 0.5 µg/lane purified DNAs were run on a 1% agarose gel and transferred on a Nytran nylon membrane (Schleier and Schuell). To make radioactive probes, we amplified subtracted library derived plasmid DNAs as templates. We amplified DNA by PCR using primer sets just adjacent to the cloning site of plasmid DNA and used purified PCR DNA of each of the clones for hybridization probes. The nucleotide sequences of these primers are as follows.

5'-GTAACGGCCGCCAGTGTGCTG-3'   [SEQ ID NO: 10]
and

5'-CGCCAGTGTGATGGATATCTGCA-3'   [SEQ ID NO: 11]

Virtual Northern analysis of total RNA of human DCs and control placenta was also performed. The probes used and RNA preparation were described above. Radiolabeling of probes, hybridization, washing and autoradiography were done as described above.

Hamster Anti-mB7-DC Ab Production

Stable transfectants of B7-DC in DC2.4, RAW246.7 and RENCA cell lines were used to immunize Armenian Hamsters. The B7-DC was cloned into the modified pCAGGS vector (30). The hamsters were boosted three times with plasmids containing B7-DC (Rockland). The anti-B7-DC antibody used in this study was from one the sera of one of the three hamsters immunized.

CD28-12, CTLA4-Ig and PD-1-Ig Binding Assay 293T cells were transfected with B7.1-pCAGGS, B7-DC-pCAGG, PD-1-pCAGGS or vector alone using Lipofectamine 2000 (Gibco BRL). After 24 hrs, cells were resuspended in FACS buffer (1×HBSS, 2% calf serum, 10 mM HEPES and 0.1% NaN$_3$) and spun at 1000 rpm for 5 min at 4° C. The buffer was then decanted, antibody added to the tubes, incubated at 4° C. for 20 mm, washed 2× with FACS buffer, and repeated this for secondary antibody. The samples were run on FACScan. B7.1 antibody was used 1:5 dilution, 10 µl/sample (Cal-Tag). Recombinant CD28-g, CTLA-4-Ig and PD-1-Ig chimeras were used at 2 µg/ml, 10 µl/sample (R&D System, Inc). Goat F(ab')$_2$ anti-human IgG-PE was used at 1:20 dilution (Southern Biotechnology Associates, Inc.).

B7-DC-Ig Dimer Synthesis

The B7-DC-Ig construct was made by fusing the sequence encoding the N-terminal amino acids of B7-DC without the transmembrane domain in-frame to the sequence encoding the C-terminal amino acids of the human IgG, Fc in the pIg-Tail Plus vector (R &D systems). COS-7 cells were transiently transfected with pIg-DC using LipofectAMINE 2000 (GIBCO BRL) or GINE JAMER(Stratagene). The B7-DC-Ig fusion protein was purified from the serum-free supernatants using the saturated ammonium sulfate precipitation. SDS-PAGE and silver staining demonstrated a purity>90%.

T Cell Proliferation and Cytokine Assays

For costimulation assays with anti-CD3, 96 well flat bottom plates (Immulon 4 from Dynex) were precoated with anti-CD3 antibodies (2C11, Pharmingen) and B7.1-Ig (R&D System), B7-DC-Ig or Isotype control (Sigma) at 100 ng/ml were diluted in 1×PBS (Gibco) pH 7.4 for two hours at 37° C. The plates were then washed 3× with 1×PBS and blocked with RPM11640 medium supplemented with 10% FCS, Penicillin/Streptomycin, non-essential amino acids, sodium pyruvate, L glutamine, 2-mercaptoethanol for one half hour before adding T cells. Spleens and lymph nodes were obtained from 6-10 weeks old BALB/c mice. RBCs were lysed using ACK buffer and T cells were purified using dynabeads M-280 (Dynex), with the indirect method. The beads were washed 2× with PBS pH 7.4+1% FCS before adding the cells and an antibody cocktail composed of anti-Led and B220/CD45RO or CD8α (Pharmingen) was added to the cells and incubated at 4° C. with bi-direcional mixing for 30'. The cells were isolated by placing the tube in a Dynal MPC for 5', centrifuged at 1500 rpm for 5' and washed 2× with PBS pH 7.4+1% FCS to remove unbound Abs. The same procedure was repeated with 15' incubation, and the cells plated at $2\times10^5$ cells/well. After 72 h of incubation, 10 µl of $^3$H-thymidine (1 µCi/well) was added to each well and incubated for 18 hrs. Cells were harvested with a Packard Micromate Cell Harvester, and filters were read on a Packard Matrix 96 direct β counter.

For costimulation assays using the RENCA system to present HA antigen, RENCA cells were cultured with RPMI-1640 medium supplemented with 10% FCS, Penicillin/Streptomycin, non-essential amino acids, sodium pyruvate. It was induced with IFN-γ (75 U/ml) for 72 hours for MHC class II expression. They were then irradiated for 13,200 Rad. and plated at $2\times10^4$ cells/well (96 well flat bottom plates). HA110-120 peptide was then added at 2.5 ug/well and various concentrations of the Ig-fusion molecules were added, Transgenic I-E$^d$+HA specific T cells (kind gift of H. von Boelmer, Harvard University) were isolated as described above and plated at $4\times10^5$ cells/well. After 48 hr of incubation, 10 µl of $^3$H thymidine (1 µCi/well) was added to each well and incubated for 18 hrs. Cells were harvested with a Packard Micromate Cell Harvester and filters were read on a Packard Matrix 96 Direct β counter.

For analysis of cytokine production by ELISA, cultures were set up as described above and supernatants were harvested at the indicated times. IL-2, IL-10 and IFN-γ concentrations were determined using commercially available ELISA kits (Endogen), and IL-4 and IL-6 (R&D System).

In Vivo Costimulation

Pooled axillary, inguinal, cervical, and mesenteric LNs from the TCR transgenic mouse line 6.5 that expresses a TCR recognizing an I-Ed restricted HA epitope ($^{110}$SFERFEIF-PKE$^{120}$ [SEQ ID NO:12]) on a B10.D2 genetic background were dissociated in RPMI media (GIBCO BRL), passed over 100 µm nylon cell strainer, and washed in sterile Hank's buffer (GIBCO BRL). After FACS® staining to determine the proportion of clonotypic CD4 cells, a cell preparation containing $2.5\times10^6$ clonotypic cells in 0.2 ml sterile Hank's buffer was injected intravenously (i.v.) into the tail vein of recipient B10.D2 mice. Three days after this adoptive transfer, the animals were vaccinated via subcutaneous (s.c.) injection into the hind footpads. Each mouse received bilateral injections of one of three preparations:

(A) 10 µg synthetic HA (per footpad) (HA peptide (110-120) combined in a 1:1 v/v ratio with incomplete Freund's Adjuvant (IFA) (Sigma), (B) the HA-IFA mixture with 25 kg of B7-DC-Ig, or (C) the HA-IFA mixture with 25 µg of an isotype control antibody. 7 days later, draining LNs nodes were harvested; $1.5\times10^5$ LN cells were incubated in round-bottom 96-well tissue culture plates with the indicated concentration of synthetic HA peptide. Proliferation assays were performed by pulsing 48 h cultures with 1 µCi [$^3$H]thymidine and incubating an additional 12 h before harvest and determination of the amount of incorporated radioactivity.

Example II

Identification and Characterization Of B7-DC

B7-DC was isolated from a subtracted library between DCs and activated macrophages. The two populations used for cDNA subtraction were bone marrow-derived GM-CSF cultured DCs as the "tester" population and γ-interferon+LPS activated adherent bone marrow-derived M-CSF macrophages as the "driver" population. Day 8 MHC class II$^{hi}$B7$^{hi}$ "mature" DCs were sorted to >93% purity as the source of tester cDNA. DCs were characterized by flow cytometry as having roughly 50 fold higher MAC class II levels than macrophages. Both populations expressed B7.1 and B7.2 although B7.2 levels were significantly higher in the DCs. F4/80 and CD16 were expressed at higher levels on the macrophage population. Functional comparison of the two populations demonstrated that the DC population was roughly 100 fold more potent than the macrophage population in stimulating an allogeneic mixed lymphocyte reaction.

After RNA extraction from both populations, we used a PCR based cDNA synthesis system followed by the PCR based subtraction procedure, PCR Select. One of the differentially expressed clones encoded a novel immunoglobulin supergene family member, which we name B7-DC. The murine B7-DC cDNA is ~1.7 kb in length encoding a 247 amino acid (aa) precursor protein with a 23 aa N-terminal signal peptide and a predicted molecular weight of ~25 kd (Table 1). The putative leader sequence and transmembrane domain were identified using the SOSUI program(31). Two charged aa are found within the 23 aa transmembrane domain of mB7-DC, suggesting a possible binding partner. At the aa level, murine B7-DC is 70% identical to the human B7-DC indicating that they are orthologues (See Tables below)

TABLE 1

Amino acid sequence comparison of murine B7-DC and human B7-DC. The mB7-DC putative leader and transmembrane domain are over-lined. The alignment was done using Clustalw-Gonnet Pam250 matrix. The [*] indicates identical amino acids and [:] shows conservative substitutions. Cysteine residues that may be important in the formation of disulfide bonds inside the immunoglobulin V or C domains are italicized . . .

```
       Putative leader sequence
mB7-DC MLLLLPILNLSLQLHPVAALFTVTAPKEVYTVDVGSSVSLECDFDRRECTELEGIRASLQ hB7-DC MIFLLLMLSLELQLHQIAALFTVTVPKELYIIEHGSNVTLECNFDTGSHVNLGAITASLQ
       *::**  :*.*.**  :***.*:*  ::  **.*:*:    ..:*  .*  **** mB7-DC KVENDTSLQSERATLLEEQLPLGKALFHIPSVQVRDSGQYRCLVICGAAWDYKYLTVKVK hB7-DC KVENDTSPHRERATLLEEQLPLGKASFHIPQVQVRDEGQYQCIIIYGVAWDYKYLTLKVK
       *****  :  *********** .*.*:*:.:* *.******:* mB7-DC ASYMRIDTRILEVPGTGEVQLTCQARGYPLAEVSWQNVSVPANTSHIRTPEGLYQVTSVL hB7-DC ASYRKINTHILKVPETDEVELTCQATGYPLAEVSWPNVSVPANTSHSRTPEGLYQVTSVL
       ***  :*:*::  *.:* ***** ****** ************

Putative TM domain
mB7-DC RLKPQPSRNFSCMFWNAHMKELTSAIIDPLSRMEPKVPRTWPLHVFIPACTIALIFLAIV hB7-DC RLKPPPGRNFSCVFWNTHVRELTLASIDLQSQMEPRTHPTWLLHIFIPSCIIAFIFIATV
       **** *.***:*:*::*** * ** *:*:.    :*:* ::* * mB7-DC IIQRKRI------------------------- hB7-DC IALRKQLCQKLYSSKDTTKRPVTTTKREVNSAI
       *  **::
```

TABLE 2

Amino acid sequence comparison of mB7-DC and mB7-H1.

```
mB7-DC MLLLLPILNLSLQLHPVAALFTVTAPKEVYTVDVGSSVSLECDFDRRECTELEGIRASLQ mB7-H1 -MRIFAGIIFTACCH-LLRAFTITAPKDLYVVEYGSNVTMECRFPVERELDLLALVVYWE
        : ::. : ::    * :   :**::*.*:  **.*::**  *     .:*  .:.   :

mB7-DC K----------VENDTSLQSE----RATLLEEQLPLGKALFHIPSVQVRDSGQYRCLVIC mB7-H1 KEDEQVIQFVAGEEDLKPQHSNFRGRASLPKDQLLKGNAALQITDVKLQDAGVYCCIISY
       *              *:*  .  *  .    **:*  ::**   *:*   ::*..*:::*:* *  *::

mB7-DC GAAWDYKYLTVKVKASYMRIDTRILEVPGTGEVQLTCQARGYPLAEVSWQN-----VSVP mB7-H1 GGA-DYKRITLKVNAPYRKINQRISVDPATSEHELICQAEGYPEAEVIWTNSDHQPVSGK
       *.* ***  :*:**:*.*  :*:  **    *.*.* :* *.*  * *          ** mB7-DC ANTSHIRTPEGLYQVTSVLRLKPQPSRNFSCMFWNAH--MKELTSAIIDPLSPMEPKVPR mB7-H1 RSVTTSRTEGMLLNVTSSLRVNATANDVFYCTFWRSQPGQNHTAELIIPELPATHPPQNR
       ..: **   * :* ::.  ..  * *  .::      :.  :.    *.    .*    * mB7-DC T-WPLHVFIPACTIALIFLAIVIIQRKRI------------------------- nB7-H1 THWVLLGSILLFLIVVSTVLLFLRKQVRMLDVEKCGVEDTSSKNRNDTQFEET
       *  *  *     *     *.:   :  :..:  ::  *:
```

The hB7-DC differs slightly from the murine B7-DC in that it has a longer cytoplasmic tail.

TABLE 3

Amino acid sequence comparison of B7-DC to the B7 family members.

| Reference B7 Protein | Compared to: | % identity[1] | % similarity[2] |
|---|---|---|---|
| mB7-DC | hB7-DC | 70 | 80 |
|  | hBT3.1 | 25 | 41 |
| mB7-DC | mB7-H1 | 34 | 48 |
|  | mBT[4] | 30 | 45 |
|  | mB7.1 | — | —[3] |
|  | mB7.2 | — | — |
|  | mB7RP-1/B7h | — | — |
| MBT | mB7.1 | 24 | 48 |
|  | mB7.2 | 24 | 40 |
| MB7.1 | mB7.2 | 27 | 45 |
| MB7-H1[5] | mB7.1 | 23 | 40 |
|  | mB7.2 | 25 | 49 |
|  | mB7RP-1/B7h | 24 | 41 |
|  | mBT | 24 | 45 |

Comparison were done using NCBI blast2 search (matrix BLOSUM62).
[1]Identical amino acids at corresponding positions
[2]Similar amino acids at corresponding position - grouped as follows: (A, G); (S, T); (E, D); (R, K, H); (Q, N); (V, I, L, M); (Y, F); (W); (C); (P)
[3]no significant similarity was found using matrix BLOSUM62
[4]BT = butyrophilin
[5]=PDL-1

Through a homology search, it was found that B7-DC has significant homology to B7-H1 (34% identity, 48% similarity) (Table 2), to a lesser extent butyrophilin (30% identity, 45% similarity), and <20% identity to B7.1 and B7.2 (Table 3). Phylogenetic studies indicate that butyrophilin is likely related to the B7 family through exon shuffling(32, 33). They each possess the canonical IgV-IgC structure and a transmembrane domain. In contrast to the other B7 family members, murine B7-DC has an extremely short cytoplasmic tail (4 aa).

To determine the genomic structure of mB7-DC, the present inventors isolated a genomic clone by screening a pooled Bacterial Artificial Chromosome (BAC) library using probes from the 5' and 3' UTRs. Chromosome location mapping was performed using the BAC clones. Chromosome localization of B7-DC was done using florescent in situ hybridization (FISH). Measurements of 10 specifically labeled chromosomes 19 demonstrated that mB7-DC is located at a position which is 47% of the distance from the heterochromatic-euchromatic boundary to the telomere of chromosome 19, an area that corresponds to the interface between bands 19C2 and 19C3. Specific hybridization signals were detected by incubating the hybridized slides in fluoresceinated antidigoxigenin antibodies followed by counter staining with DAPI. This locus corresponds to a region of human chromosome 9, where hB7-H1 has been mapped.

hB7-DC was found to be located on two chromosome 9 BAC clones. In addition, both hB7-DC and hB7-H1 were found to be located on a single chromosome 9 BAC clone with an insertion size of approximately 164 kb (FIG. 1). The genomic proximity of B7-DC and B7-H1 is reminiscent of the B7.11/B7.2 pair, which map to within one megabase of each other.

Example III

B7-DC is Selectively Expressed in Dendritic Cells

Figure 2:
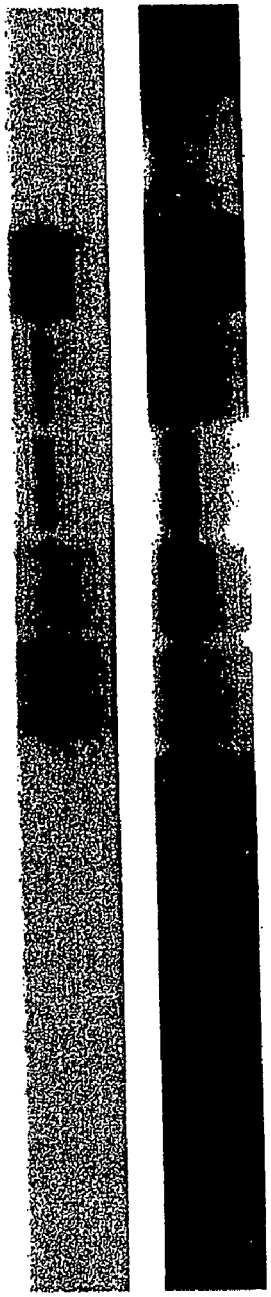
FIG. 2 shows that B7-DC is differentially expressed between DCs and macrophages. Distribution of B7-DC mRNA in bone marrow DCs, splenic DCs, macrophages, macrophage lines and tissues was assessed by virtual Northern blot analysis using 0.5 µg/lane purified DNA run on a 1% agarose gel. G3PDH was used as control. J774A1, Raw264.7, Pu5-1.8 and WEHI cells are macrophage cell lines. BM: bone marrow.
Figure 3:
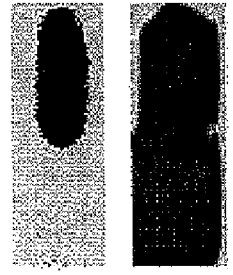
FIG. 3 shows a virtual Northern blot of B7-DC expression on human DCs. Lane 1 shows human DCs cultured with GM-CSF+Flt-3L, lane 2 shows human placenta and lane 3 shows human DCs cultured with GM-CSF+IL4. Oligonucleotides from the 5' and 3' UTR of human B7-DC were used to make PCR DNA probe for virtual Northern analysis of total RNA of human DCs. β-actin was used as control to ensure the quality of mRNA.
Figure 4:
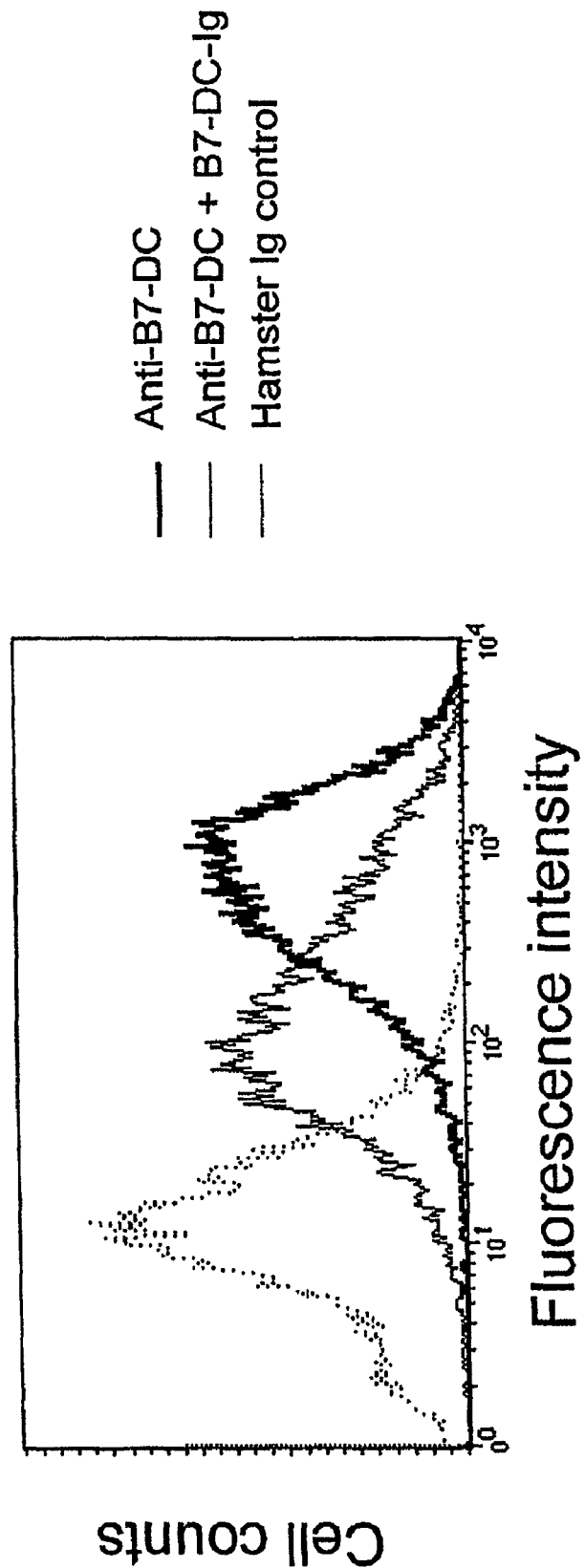
FIG. 4 represents is a flow cytometric analysis showing surface expression of B7-DC on mature BM-DCs. Day 9 murine BM-DCs were Fc-blocked and stained with control antibody or B7-DC antisera. Specificity of binding was demonstrated by adding B7-DC-Ig to compete for the binding of anti-B7-DC to the surface of DCs.

In order to determine the expression pattern of B7-DC, virtual Northern analysis was performed using RNA extracted from multiple tissues, macrophage cell lines, macrophage cultures and dendritic cells derived from both bone marrow and spleen. While strong hybridization was detected using a B7-DC probe in immature (day 4,6) and mature (day 8 and sorted MHC II$^{hi}$B7$^{hi}$) bone marrow derived DC and splenic DC, no signal was detected in any of 4 macrophage cell lines, activated SM macrophages or peritoneal macrophages (FIG. 2). Strong expression of hB7-DC was detected in human DCs grown from peripheral blood mononuclear cells with GM-CSF plus either IL-4 or Flt-3L (FIG. 3). In order to verify cell surface expression of B7-DC protein, anti-mB7-DC antibodies were used to stain DCs. Staining, blockable with soluble 87-DC-Ig, was observed on DC (FIG. 4).

B7-DC does not Bind to CD28 or CTLA4 but does Bind to PD-1

Figure 5:
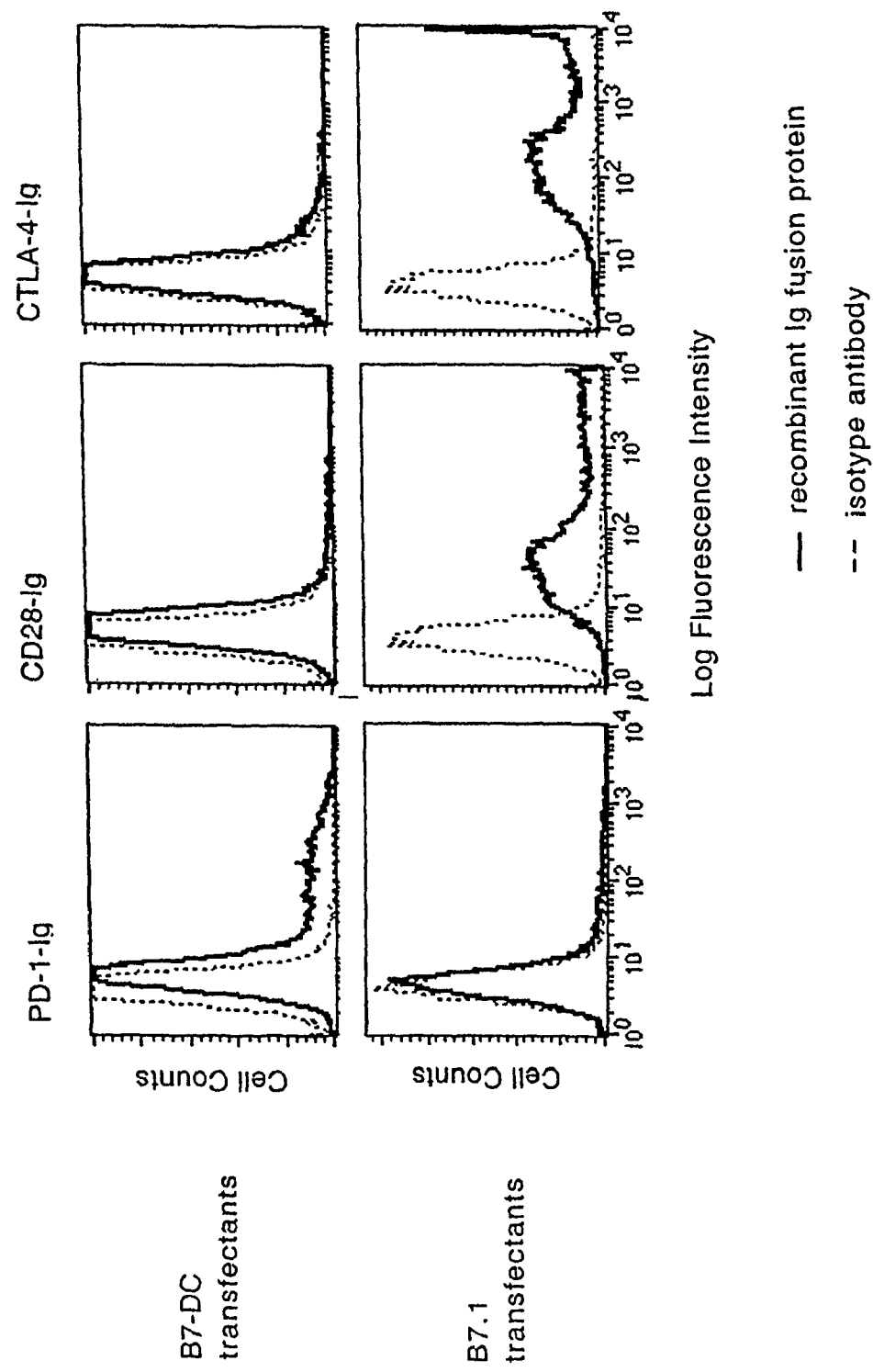
FIG. 5 shows the binding of B7-DC to PD-1 but not CTLA-4 or CD28. 293T cells were transiently transfected with pCAGGS-B7.1 o pCAGGS-B7-DC. Transfectants were stained with PD-1-Ig, 28-Ig and CTLA-4-Ig fusion molecules followed by PE-labeled secondary antibody. Staining of pCAGGS (empty vector) transfectants was negative (not shown)

Although B7-DC has structural and sequence homology to the B7 family, it does not contain the putative CD28/CTLA-4 binding sequence, SQDXXXELY [SEQ ID NO:13] or XXX-YXXRT [SEQ ID NO:14] (34) (where X=any amino acid). To directly assess binding, the ability of dimeric CD28-Ig and CTLA-4-Ig to stain 293T cells transfected with either B7-DC or B7.1 was investigated. Whereas strong binding was observed with B7.1 transfectants, there was no binding to 87-DC transfectants (FIG. 5). Based on homology and genomic proximity between B7-DC and B7-H1/PD-L1, experiments were conducted to test PD-1 as a candidate binding partner for B7-DC. Ideed, PD-110IG bound to B7-DC transfectants but not to B7.1 transfectants. The binding of BPD-1-Ig too B7-DC transfectants was lower than the binding of CTL-4-It and CD28-Ig to B7.1 transfectants, although it was specific. Further confirmation of the binding of PD-1 to B7-Dc was obtained from positive straining of stable 87-DC-GFP transfectants with PD-1-Ig. It was concluded that, as with B7-H1 and B7h/B7RP-1, B7-DC does not use CD28 or CTLA-4 as receptors. Rather, PD-1 appears to be a receptor for B7-DC.

Example IV

B7-DC Functions as a Costimulatory Molecule for T Cells

Figure 6:
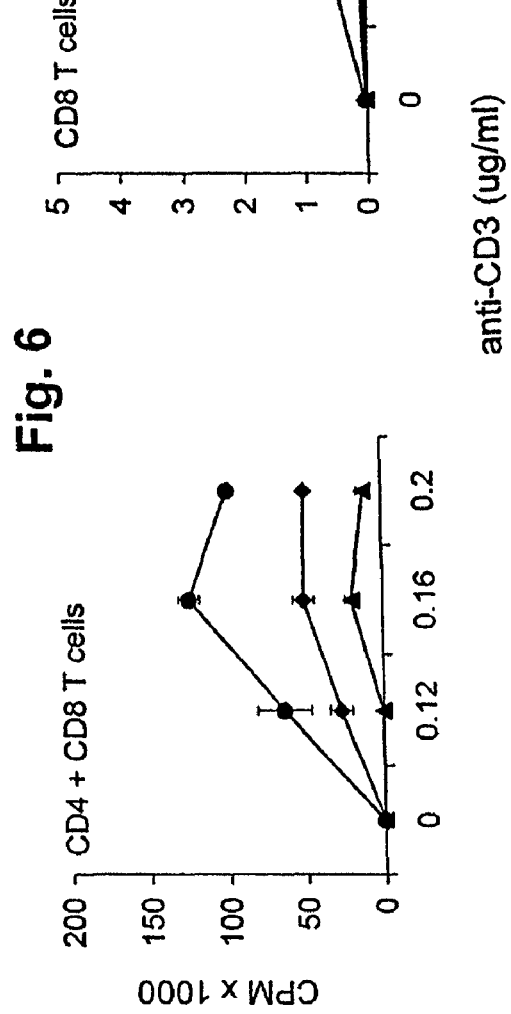
FIG. 6 (left and right panel) shows the costimulation of T cell proliferation by anti-CD3 and B7-DC-Ig. Left graph: purified T cells (CD4+CD8) were cultured in wells pre-coated with increasing concentrations of anti-CD3 (mAb 2C11) and a fixed concentration (0.1 µg/ml) of immobilized B7.1-Ig (♦), B7-DC-Ig (●) or isotype control (▲). Results depict one representative experiment of three. Cells were incubated for 72 h and labeled with $^3$H-thymidine. CPM, counts per minute. Right Graph: purified CD8 T cells were cultured in wells pre-coated with increasing concentrations of anti-CD3 and fixed concentration of immobilized B7.1-Ig (♦), B7-DC-Ig (●) or isotype control (▲) as in (a). Results are of one representative experiment of two. Cells were incubated for 72 h and labeled with ³H-thymidine. CPM, counts per minute.

A soluble B7-DC-Ig fusion protein which could be added to T cell stimulation assays was produced for use in testing whether B7-DC possessed costimulatory activity. The proliferative response of T cells was measured to stimulation by increasing amounts of immobilized anti-CD3 in the presence of either B7-DC-Ig, B7.1-Ig or an isotype control. FIG. 6 (left) shows that, in the presence of suboptimal anti-CD3 concentration, B7-DC costimulated a greater T cell proliferative response than did B7.1. Furthermore, B7-DC costimulated proliferative responses were higher in CD4 than in CD8 cells (FIG. 6, right). B7-DC failed to stimulate T cells in the absence of a TCR-focused stimulus, indicating that B7-DC was providing a true costimulatory signal.

Figure 7:
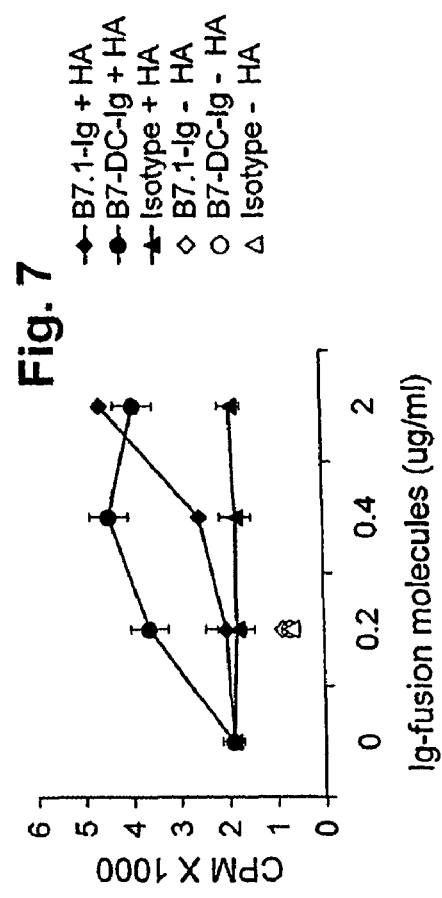
FIG. 7 shows the costimulation of antigen-specific T cell proliferative responses RENCA cells were treated with IFNγ for 72 hrs to induce MHC class II expression and incubated with 12.5 μg/ml of HA110-120 peptide. Purified HA+-I-E$^d$ specific transgenic T cells were added together with increasing concentrations of either B7.1-Ig (♦), B7-DC-Ig (●) or Isotype control (▲) in soluble form. Cells were incubated for 48 h and labeled with ³H-thymidine. CPM, counts per minute. Results are one representative experiment of three.
Figure 8:
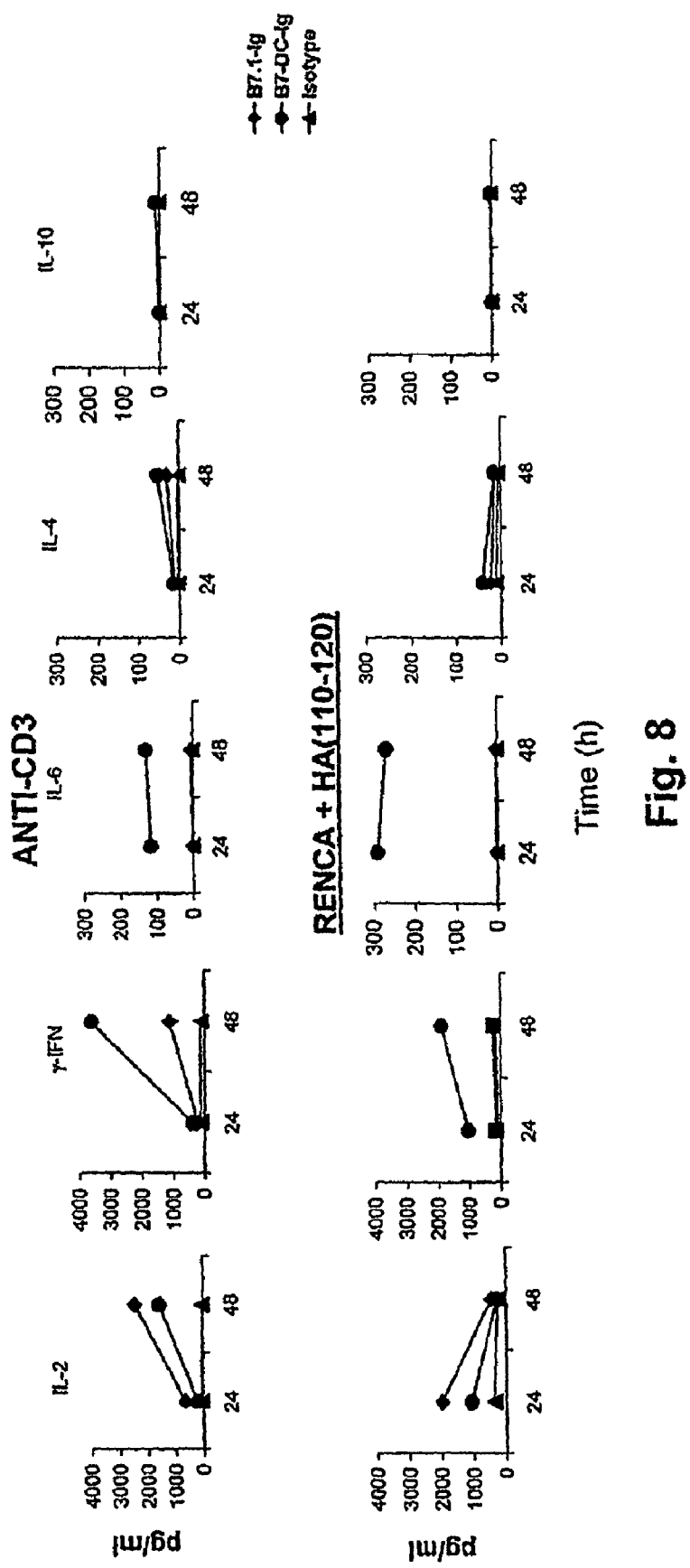
FIG. 8 shows cytokine secretion of T cells costimulated by B7-DC. Upper panels: purified T cells were cultured in wells pre-coated with anti-CD3 (0.12 μg/ml) and 0.1 μg/ml of immobilized B7.1-Ig (♦), B7-DC-Ig (●) or isotype control (▲) as in FIG. 6 (left). Results depict one representative experiment of three. Lower panels: γ-IFN treated RENCA cells loaded with 125 μg/ml HA(110-120) peptide were incubated with purified HA+I-E$^d$ specific transgenic T cells together with 2 μg/ml of soluble B7.1-Ig, B7-DC-Ig or isotype control (symbols as above). Results depict one representative experiment of two. Supernatants were collected after 24 h and 48 h culture and assayed for the indicated lymphokines using ELISA.

B7-DC also costimulated a proliferative responses when "signal 1" was provided by an MHC-peptide complex. RENCA cells (which express no endogenous B7.1, P7.2 or B7-DC by RT-PCR analysis) were treated with γ-IFN to induce MHC class II expression. These cells were loaded with the I-E$^d$ restricted HA 110-120 peptide (FERFEIFPKE)(35) [SEQ ID NO:15]. Purified splenic T cells from an I-E$^d$+HA 110-120 specific TCR transgenic mouse line were added and the proliferative response was measured in the presence of either B7-DC-Ig, B7.1-Ig or an isotype control. FIG. 7 shows that B7-DC possessed greater costimulatory activity than did B7.1.

Patterns of Lymphokine Production Costimulated by B7-DC

The best characterized T cell responses to costimulation by the B7 family molecules is lymphokine production. These lymphokines are important mediators of T cell effects. Studies were done to analyze production of a number of different lymphokines by T cells that had been stimulated with anti-CD3 or HA antigen (FIG. 8) costimulated with either B7-DC-Ig, B7.1-Ig or an isotype control. Patterns of lymphokine costimulation were fairly consistent whether anti-CD3 or an MHC-peptide complex was utilized as "signal 1". Significantly, B7-DC costimulated greater levels of γ-IFN than did B7.1. B7-DC also costimulated significant amounts of IL-6 production whereas B7.1 costimulated virtually none. While both molecules costimulated IL-2 production, B7.1 did so more efficiently than did B7-DC. Thus, the patterns of costimulation by B7-DC and P7.1 are distinct, with B7-DC being more efficient in costimulating important proinflammatory lymphokines.

Example V

B7-DC Enhances In Vivo Immune Responses

Figure 9:
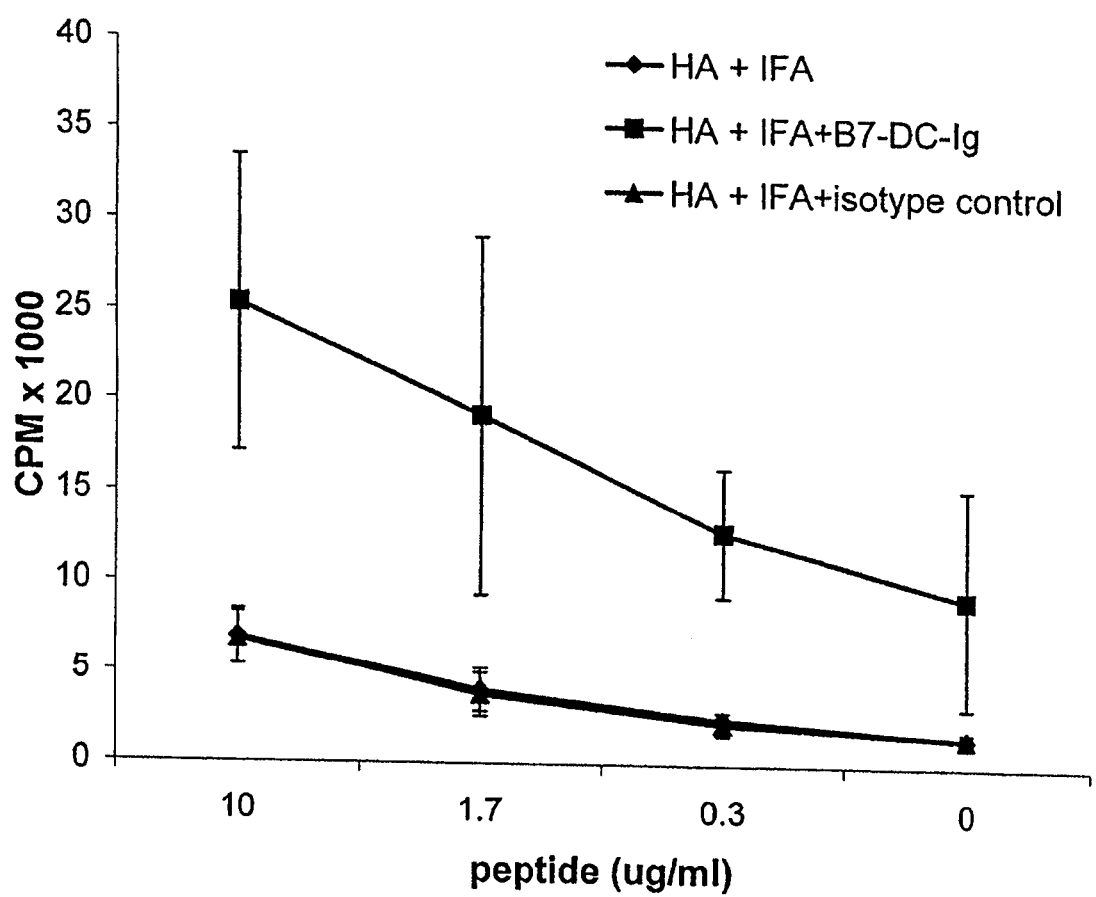
FIG. 9 shows that B7-DC-Ig greatly enhances antigen specific proliferation after in vivo co-stimulation. After adoptive transfer of 2.5×10⁶ TCR transgenic cells specific for HA, three groups of mice were immunized s.c., in their hind footpads with either HA peptide (110-120), incomplete Freund's adjuvant (IFA) alone or in combination with either B7-DC-Ig+IFA or an isotype control antibody with IFA. Draining lymph nodes were harvested on day 7.1.5×10⁵ LN cells were incubated with the HA peptide for 48 h, pulsed with 1 μCi [³H]thymidine and the radioactivity incorporated after 12 h was determined.

In order to determine whether B7-DC possesses in vivo biologic activity, the inventors asked whether B7-DC-Ig enhanced immune responses to peptide vaccines. B7-DC-Ig or an isotype control antibody was added to the immunogenic cocktail of HA 110-120 peptide and IFA. To permit enumeration of HA-specific CD4 T cells in vivo, $2.5 \times 10^6$ anti-HA 6.5 T cells were transferred into the mice 3 days before immunization. Seven days after immunization, draining LN cells were harvested and the cells stimulated in vitro for 2 days with varying amounts of HA110-120 peptide. FIG. 9 shows that addition of B7-DC-Ig indeed dramatically enhanced the proliferative response to HA. The total number of HA-specific T cells in draining LN was increased by roughly 2 fold in groups receiving B7-DC-Ig relative to isotype antibody controls. It was therefore concluded that B7-DC had the ability to enhance antigen-specific responses even on a per cell basis.

Example VI

Discussion and Conclusions

The present inventors have discovered and characterized a new B7 family member with expression highly restricted to DCs and having unique costimulatory properties for T cells. The human orthologue of B7-DC is also expressed in DCs.

This restricted expression pattern contrasts with the previously described B7 family members, suggesting that B7-DC participates in different immune responses than the known B7.1/2 pathways. While a weak B7-DC signal was detected by RT-PCR in activated macrophages, preliminary realtime RT-PCR analysis indicated that B7-DC mRNA expression in DCs was >15-fold higher than in activated macrophages. Antibody staining likewise detected very low levels of B7-DC on the surface of activated macrophages. It is unclear whether this is sufficient for significant T cell activation.

The unusual pattern of lymphokine production that B7-DC costimulates implies a unique biologic role compared to other B17 family members. The traditional classification of cytokines is as follows: Th1 cytokines include IL-2, γ-IFN and lymphotoxin; Th2 cytokines include IL-4, IL-S, IL-6 and IL-13 (36). B7-DC does not induce either a classic Th1 or Th2 lymphokine profile. B7-DC induces very little IL-4 and no IL-10. However, IL-6 is considered a Th2 cytokine. The lower IL-2 and higher γ-IFN costimulated by B7-DC relative to B7.1 does not conform to a classic Th1 pattern. Nonetheless, the high γ-IFN production suggests that B7-DC evokes important T cell effector function.

B7-DC is noteworthy in its ability to costimulate IL-6. The robust proliferative response of T cells induced by B7-DC is explained in part by its strong costimulation of IL-6 production, which is not observed with B7.1 IL-6 is a potent amplifier of T cell proliferation (in conjunction with other proliferative stimuli) (37, 38). IL-6 is a multifunctional cytokine that regulates not only T cell function but also proinflammatory responses, monocyte differentiation, B cell differentiation, thrombopoiesis, bone resorption, and the growth of certain hematopoietic tumors (39, 40). IL-6 can function in concert with soluble IL6 receptors (sIL-6R) in the induction of chemokines and leukocyte recruitment(41). It can mediate potent antiapoptotic effects via Stat-3 activation. IL-6 dependent Stat-3 activation in T cells has been reported to be an important pathway for the survival of activated T cells (42, 43) although other reports suggest that Stat-3 exerts its effect on resting T cells.

While B7-DC fails to bind CD28 or CTLA-4, it does bind PD-1, a receptor for B7-H1/PD-L1 (22, 47, 48). It has not yet been determined whether it binds ICOS, a receptor for B7h/B7RP-1 (23-25, 44-46). The marked homology between B7-DC and B7-H1/PD-L1 (greater than that between B7.1 and B7.2), the close physical linkage of hB7-H1/PD-L1 and B7-DC and their binding to a common receptor, suggests that they are related by a relatively recent gene duplication event. This is analogous to the relationship between B7.1 and B7.2, which both map to within one megabase on mouse chromosome 16 and on human chromosome 3 (49).

It will be important to discern the relative biologic roles of B7-DC vs B7-H1/PD-L1 as mediated by PD-1 and other putative receptor(s). PD-1 is expressed subsequent to, and appears to inhibit, T cells activation. PD-1 induces apoptosis under conditions of T cell stimulation with high concentrations of anti-CD3. PD-1 knockout mice develop an autoimmune syndrome (22) characterized by clinical manifestations of hypertrophic cardiomyopathy. In contrast, Dong et al. (21) reported that B7-H1/PD-L1 co-stimulated T cell proliferation and cytokine release at lower concentrations of anti-CD3. By analogy to the relationship of CD28/CTLA-4, PD-L1 may be a counterreceptor for an as yet unidentified activating receptor. Despite sharing the property of binding to PD-1, B7-DC and B7-H1 are distinct in their lymphokine costimulation patterns; B7-H1 costimulated T cell IL-10 production whereas B7-DC does not. The distinct cellular expression patterns and costimulatory functions of B7-DC suggest a unique role in immune function.

The references cited above and below are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

DOCUMENTS CITED

In Addition to Documents Cited Fully in the Text, Certain Documents are Cited by Number Only (Parenthetical); the Latter are Listed Below.

1. Hathcock, K. S., G. Laszlo, C. Pucillo, P. Linsley, and R. J. Hodes. 1994. Comparative Analysis of B7-1 and B7-2 costimulatory ligands: expression and function. *J Exp Med* 180, no. 2:631.
2. Razi-Wolf, Z., G. J. Freeman, F. Galvin, B. Benacerraf L. Nadler, and H. Reiser. 1992. Expression and function of the murine B7 antigen, the major costimulatory molecule expressed by peritoneal exudate cells. *Proc Natl Acad Sci USA* 89, no. 9:4210.
3. Steinman, R. M. 1991. The dendritic cell system and its role in immunogenicity. *Annu Rev Immunol* 9:271.
4. Banchereau, J., and R. M. Steinman. 1998. Dendritic cells and the control of immunity. *Nature* 392, no. 6673:245.
5. Patterson, S. 2000. Flexibility and cooperation among dendritic cells. *Nature Immunol.* 1, no. 4.273.
6. Langenkamp, A., M. Messi, A. Lanzavecchia, and S. Federica. 2000. Kinetics of dendritic cell activation: impact on priming of Th1, Th2 and nonpolarized T cells. *Nature Immunol.* 1, no. 4:311.
7. Thompson, C. B., F. Lindsten, J. A. Ledbetter, S. L. Kunel, H. A. Young, S. G. Emerson, J. M. Leiden, and C. H. June. 1989. CD28 activation pathway regulates the production of multiple T-cell-derived lymphokines/cytokines. *Proc Natl Acad Sci USA* 86, no. 4:1333.
8. Harding, F. A., J. G. McArthur, J. A. Gross, D. H. Raulet, and J. P. Allison. 1992. CD28-mediated signalling co-stimulates murine T cells and prevents induction of anergy in T-cell clones. *Nature* 356, no. 6370:607.
9. Linsley, P. S., W. Brady, L. Grosmaire, A. Aruffo, N. K. Damle, and J. A. Ledbetter. 1991. Binding of the B cell activation antigen B7 to CD28 costimulates T cell proliferation and interleukin 2 mRNA accumulation. *J Exp Med* 173, no. 3:721.
10. Fraser, J. D., B. A. Irving, G. R. Crabtree, and A. Weiss. 1991. Regulation of interleukin-2 gene enhancer activity by the T cell accessory molecule CD28. *Science* 251, no. 4991:313.
11. Lindstein, T., C. H. June, J. A. Ledbetter, G. Stella, and C. B. Thompson. 1989. Regulation of lymphokine messenger RNA stability by a surface-mediated T cell activation pathway. *Science* 244, no. 4902:339.
12. Linsley, P. S., W. Brady, M. Urnes, L. S. Grosmaire, N. K. Damle, and J. A. Ledbetter. 1991. CTLA-4 is a second receptor for the B cell activation antigen B7. *J Exp Med* 174, no. 3:561.
13. Waterhouse, P., L. E. Marengere, H. W. Mittrucker, and T. W. Mak. 1996. CTLA-4, a negative regulator of T-lymphocyte activation. *Immunol Rev* 153:183.
14. Kuchroo, V. K., M. P. Das, J. A. Brown, A. M. Ranger, S. S. Zamvil, R. A. Sobel, H. L. Weiner, N. Nabavi, and L. H. Glimcher. 1995. B7-1 and B7-2 costimulatory molecules activate differentially the Th1/Th2 developmental pathways: application to autoimmune disease therapy. *Cell* 80, no. 5:707.
15. Lanier, L. L., S. O'Fallon, C. Somoza, J. H. Phillips, P. S. Linsley, K. Okumura, D. Ito, and M. Azuma. 1995. CD80 (B7) and CD86 (B70) provide similar costimulatory signals for T cell proliferation, cytokine production, and generation of CTL. *J Immunol* 154, no. 1:97.
16. Van Parijs, L., M. P. Sethna, A. N. Schweitzer, F. Borriello, A. H. Sharpe, and A. K. Abbas. 1997. Functional consequences of dysregulated B7-1 (CD 80) and B7-2 (CD86) expression in B or T lymphocytes of transgenic mice. *J. Immunol* 159, no. 11:5336.
17. Abbas, A. K., and A. H. Shape. 1999. T-cell stimulation: an abundance of B7s [news; comment]. *Nal Med* 5, no. 12:1345.
18. Borriello, F., M. P. Sethna, S. D. Boyd, A. N. Schweitzer, E. A. Tivol, D. Jacoby, T. B. Strom, E. M. Simpson, G. J. Freeman, and A. H. Sharpe. 1997. B7-1 and B7-2 have overlapping, critical roles in immunoglobulin class switching and germinal center formation. *Immunity* 6, no. 3:303.
19. Sharpe, A. I. 1995. Analysis of lymphocyte costimulation in vivo using transgenic and 'knockout' mice. *Curr Opin Immunol* 7, no. 3:389.
20. Green, J. M., P. J. Noel, A. I. Sperling, T. L. Walunas, G. S. Gray, J. A. Bluestone, and C. B. Thompson. 1994. Absence of B7-dependent responses in CD28-deficient mice. *Immunity* 1, no. 6:501.
21. Dong, H., G. Zhu, K. Tamada, and L. Chen. 1999. B7-H1, a third member of the B7 family, co-stimulates T-cell proliferation and interleukin-10 secretion [see comments]. *Nat Med* 5, no. 12:1365.
22. Freeman, G. J., A. J. Long, Y. Iwai, K. Bourque, T. Chernova, H. Nishimura, L. J. Fitz, N. Malenkovich, T. Okazaki, M. C. Byrne, H. F. Horton, L. Fouser, L. Carter, V. Ling, M. R. Bowman, B. M. Carreno, M. Collins, C, R. Wood, and T. Honjo. 2000. Engagement of the PD-1 immunoinhibitory receptor by a novel B7 family member leads to negative regulation of lymphocyte activation. *J Exp Med* 192, no. 7:1027.
23. Swallow, M. M., J. J. Wallin, and W. C. Sha. 1999, B7h, a novel costimulatory homolog of B7.1 and B7.2, is induced by TNFalpha. *Immunity* 11, no. 4:423.
24. Wang, S., G. Zhu, A. S. Chapoval, H. Dong, K. Tamada, J. Ni, and L. Chen. 2000. Costimulation of T cells by B7-H2, a B7-like molecule that binds ICOS. *Blood* 96, no. 8:2808.
25. Yoshinaga, S. K., J. S. Whoriskey, S. D. Khare, U. Sarmiento, J. Guo, T. Horan, G. Shih, M. Zhang, M. A. Coccia, T. Kohno, A. Tafuri-Bladt, D. Brankow, P. Campbell, D. Chang, L. Chiu, T. Dai, G. Duncan G. S. Elliott, A. Hui, S. M. McCabe, S. Scully, A. Shahinian, C. L. Shaklee, G. Van, T. W. Mak, and et al. 1999. T-cell co-stimulation through B7RP-1 and ICOS. *Nature* 402, no. 6763:827.
26. Inaba, K., W. J. Swiggard, R. Steinman, N. Romani, and G. Schuler. 1998. Isolation of dendritic cells. John Wiley & Sons, Inc., New York.
27. Fortier, A. H., and L. A. Falk. 1994. Isolation of murine macrophages. John Wiley & Sons, Inc., New York.
28. Orimoto, K., H. Tsuchiya, J. Sakurai, M. Nishizawa, and O. Hino. 1998. Identification of cDNAs induced by the tumor suppressor Tsc2 gene using a conditional expression system in Tsc2 mutant (Eker) rat renal carcinoma cells. *Biochem Biophys Res Commun* 247, no. 3:728.
29. Romani, N., S. Gruner, D. Brang, E. Kampgen, A. Lenz, B. Trockenbacher, G. Konwalinka, P. O. Fritsch, R. M. Steinman, and G. Schuler. 1994. Proliferating dendritic cell progenitors in human blood. *J Exp Med* 180, no. 1:83.
30. Niwa, H., K. Yamamura, and J. Miyazaki. 1991. Efficient selection for high-expression transfectants with a novel eukaryotic vector, *Gene* 108, no. 2:193.
31. Hirolawa, T., S. Boon-Chieng, and S. Mitaku. 1998. SOSUI: Classification and secondary structure prediction system for membrane proteins. *Bioinformatics* 14, no. 4:378.
32. Linsley, P. S., R. Peach, P. Gladstone, and J. Bajorath. 1994. Extending the B7 (CD80) gene family. *Protein Sci* 3, no. 8:1341.

33. Henry, J., M. Ribouchon, D. Depetris, M. Mattei, C. Offer, R. Tazi-Ahnini, and P. Pontarotti. 1997. Cloning, structural analysis, and mapping of the 330 and B7 multigenic families to the major histocompatibility complex (MHC) and other chromosomal regions. *Immunogenetics* 46, no. 5:383.
34. Fargeas, C. A., A. Truneh, M. Reddy, M. Hurle, R. Sweet and R. P. Sekaly. 1995. Identification of residues in the V domain of CD80 (B7-1) implicated in functional interactions with CD28 and CTLA4. *J Exp Med* 182, no. 3:667.
35. Kirberg, J., A. Baron S. Jakob, A. Rolink, K. Karjalainen, and H. von Boehmer. 1994. Thymic selection of CD8+ single positive cells with a class II major histocompatibility complex-restricted receptor. *J Exp Med* 180, no. 125.
36. Mosmann, T. R., and R. L. Coffman. 1989. TH1 and TH2 cells: different patterns of lymphokine secretion lead to different functional properties. *Annu Rev Immunol* 7: 145.
37. Suda, T., A. O'Garra, 1. MacNeil, M. Fischer, M. W. Bond, and A. Zlotnik. 1990. Identification of a novel thymocyte growth-promoting factor derived from B cell lymphomas. *Cell Immunol* 129, no. 1:228.
38. Suda, T., R. Murray, C. Guidos, and A. Zlotnik. 1990. Growth-promoting activity of IL-1 alpha, IL-6, and tumor necrosis factor-alpha in combination with IL-2, IL4, or IL-7 on murine thymocytes. Differential effects on CD4/CD8 subsets and on CD3+/CD3− double-negative thymocytes. *J Immunol* 144, no. 8:3039.
39. Taga, T., and T. Kishimoto. 1997. Gp130 and the interleukin-6 family of cytokines. *Annu Rev Immunol* 15:797.
40. Chomarat, P., J. banchereau, J. Davoust, and A. K. Palucka. 2000. IL-6 switches the differentiation of monocytes from dendritic cells to macrophages. *Nature Immunol* 1, no. 6:510.
41. Romano, M., M. Sironi, C. Toniatti, N. Polentarutti, P. Fruscella, P. Ghezzi, R Faggioni, W. Luini, V. van Hinsbergh, S. Sozzani, F. Bussolino, V. Poli, G. Ciliberto, and A. Mantovani. 1997. Role of IL-6 and its soluble receptor in induction of chemokines and leukocyte recruitment. *Immunity* 6, no. 3:315.
42. Takeda, K., T. Kaisho, N. Yoshida, J. Takeda, T. Kishimoto, and S. Akira. 1998. Stat3 activation is responsible for IL-6-dependent T cell proliferation through preventing apoptosis: generation and characterization of T cell-specific Stat3-deficient mice. *J Immunol* 161, no. 9:4652.
43. Teague, T. K., B. C. Schaefer, D. Hildeman, J. Bender, T. Mitchell, J. W. Kappler, and P. Marrack. 2000. Activation-induced inhibition of interleukin 6-mediated T cell survival and signal transducer and activator of transcription 1 signaling. *J Exp Med* 191, no. 6:915.
44. Coyle, A. J., S. Lehar, C. Lloyd, J. Tian, T. Delaney, S. Manning, T. Nguyen, T. Burwell, H. Schneider, J. A. Gonzalo, M. Gosselin, L. R. Owen, C. E. Rudd, and J. C. Gutierrez-Ramos. 2000. The CD28-related molecule ICOS is required for effective T cell-dependent immune responses. *Immunity* 13, no. 1:95.
45. Hutloff A., A. M. Dittrich, K. C. Beier, B. Eljaschewitsch, R. Kraft. Anagnostopoulos, and R. A. Kroczek. 1999. ICOS is an inducible T-cell co-stimulator structurally and functionally related to CD28. *Nature* 397, no. 6716:263.
46. Yoshinaga, S. K., M. Zhang, J. Pistillo, T, Horan, S. D. Khare, K. Miner, M. Sonnenberg, T. Boone, D. Brankow, T. Dai, J. Delaney, H. Han, A. Hui, T. Kohno, R. Manoukian, J. S. Whoriskey, and M. A. Coccia. 2000. Characterization of a new human B7-related protein: B7RP-1 is the ligand to the co-stimulatory protein ICOS. *Int Immunol* 12, no. 10:1439.
47. Ishida, Y., Y. Agata, K Shibahara, and T. Honjo. 1992. Induced expression of PD-1, a novel member of the immunoglobulin gene superfamily, upon programmed cell death. *Embo J* 11, no. 11:3887.
48. Shinohara, T., M. Taniwaki, Y. Ishida, M. Kawaichi and T. Honjo. 1994. Structure and chromosomal localization of the human PD-1 gene (PDCD1). *Genomics* 23, no. 3:704.
49. Reeves, R. H., D. Patch, A. H. Sharpe, F. Borriello, O. J. Freeman, S. Edelhoff, and C. Disteche. 1997. The costimulatory genes Cd80 and Cd86 are linked on mouse chromosome 16 and human chromosome 3. *Mamm Genome* 8, no, 8:581.

What is claimed is:

1. A fusion polypeptide comprising a first fusion partner consisting of all or part of a B7-DC protein extracellular domain which
   (i) is fused directly to a second polypeptide or
   (ii) is fused to a linker peptide sequence that is fused to the second polypeptide,
   wherein the B7-DC protein has at least 70% sequence identity to SEQ ID NO:2.

2. A dimeric or trimeric fusion polypeptide which is a dimer or trimer of the fusion polypeptide of claim 1.

3. A vaccine composition useful for inducing an immune response against an antigen associated with a pathogenic cell or microorganism, comprising
   (a) the fusion protein of claim 1;
   (b) the antigen; and
   (c) a pharmaceutically and immunologically acceptable excipient or carrier.

4. The fusion protein of claim 1, wherein the second polypeptide comprises one or more domains of an Ig heavy chain constant region.

5. The fusion protein of claim 4, wherein the one or more domains of the Ig heavy chain comprise $C_H2$ or $C_H3$ regions of a human immunoglobulin Cγ1 chain.

6. The fusion protein of claim 1, wherein the first fusion partner is the extracellular domain encoded by nucleotides 58-663 of SEQ ID NO:1.

7. The fusion protein of claim 1, wherein the extracellular domain comprises amino acids from about position 20-221 of SEQ ID NO:2.

8. The fusion protein of claim 1, wherein the fusion protein binds to Programmed Death-1 (PD-1).

9. The fusion protein of claim 1, wherein the fusion protein co-stimulates T cells in the presence of an adequate stimulus to the T cell receptor to proliferate or to produce and secrete cytokines.

10. The fusion protein of claim 4, wherein the fusion protein is a dimeric fusion protein formed by covalent bonding of Cys residues in $C_H$ regions of two Ig heavy chains.

11. The fusion protein of claim 10 wherein the Cys residues are the same Cys residues that are disulfide linked in dimerized Ig heavy chains.

12. A fusion polypeptide of the extracellular domain of murine or human B7-DC, wherein the B7-DC polypeptide is selectively expressed on dendritic cells as compared to activated macrophages, wherein murine B7-DC polypeptide has 32% homology to human B7-H1, wherein the B7-DC polypeptide comprises single IgV and IgC domains, wherein the B7-DC polypeptide comprises a single transmembrane domain, wherein the murine B7-DC polypeptide comprises an intracytoplasmic tail 4 amino acids in length, wherein the B7-DC polypeptide does not bind to CD28 or CTLA-4 and does not include the CD28/CTLA-4 binding motifs, and wherein the 137-DC polypeptide is capable of co-stimulating T cells, with a second polypeptide.

13. The fusion polypeptide of claim 12 wherein the second polypeptide comprises: (a) one or more domains of an Ig heavy chain constant region; (b) two C domains of an IgG heavy chain constant region; or (c) the hinge, $C_H2$ and $C_H3$ regions of a human immunoglobulin Cγ1 chain.

14. The fusion polypeptide of claim 12 wherein the fusion polypeptide binds to a binding partner molecule on T cells and co-stimulates the T cells.

15. The fusion polypeptide of claim 14 wherein the binding partner molecule is a receptor on T cells that is not CD28 or CTLA-4.

16. The fusion polypeptide of claim 12, wherein the second polypeptide comprises one or more domains of an Ig heavy chain constant region.

17. A mature polypeptide comprising a first fusion partner and a second fusion partner, wherein the first fusion partner consists of an extracellular domain of a B7-DC protein comprising an IgV domain,
   wherein the B7-DC protein has at least 70% sequence identity to SEQ ID NO:2.

18. A mature polypeptide comprising a first fusion partner and a second fusion partner, wherein the first fusion partner consists of an extracellular domain of B7-DC comprising amino acid residues 20-221 of SEQ ID NO:2.

19. The mature polypeptide of claim 17, wherein the polypeptide co-stimulates T cells.

20. The fusion polypeptide of claim 1 wherein the extracellular domain comprises an amino acid sequence extending from the cysteine at position 42 of SEQ ID NO:2 to the cysteine at position 102 of SEQ ID NO:2.

21. The fusion polypeptide of claim 1 wherein the extracellular domain comprises an amino acid sequence extending from the cysteine at position 42 of SEQ ID NO:2 to the cysteine at position 192 of SEQ ID NO:2.

22. The fusion polypeptide of claim 1 wherein the extracellular domain comprises an IgV domain.

23. The fusion polypeptide of claim 1 wherein the extracellular domain comprises an IgV and an IgC domain.

24. The mature polypeptide of claim 17 wherein the extracellular domain of B7-DC comprises an IgV domain and an IgC domain.

25. The vaccine composition of claim 3 further comprising a general immunostimulatory agent or adjuvant.

26. A fusion polypeptide comprising a first fusion partner consisting of amino acids 20-221 of SEQ ID NO:2 and a second fusion partner consisting of the hinge, $C_H2$ and $C_H3$ regions of a human immunoglobulin Cγ1 chain.

27. The fusion polypeptide of claim 26 further comprising a linker between the first and second fusion partners.

28. The fusion polypeptide of claim 26 wherein the first fusion partner is directly linked to the second fusion partner.

29. The fusion polypeptide of claim 28, wherein the fusion polypeptide is a dimeric fusion protein formed by covalent bonding of Cys residues in at least one $C_H$ region of a first second fusion partner with at least one $C_H$ region of a second fusion partner.

30. A pharmaceutical composition comprising the fusion polypeptide of any one of claims 26 to 29.

31. The fusion polypeptide of claim 12, wherein the fusion protein binds to Programmed Death-1 (PD-1).

* * * * *

UNITED STATES PATENT AND TRADEMARK OFFICE
CERTIFICATE OF CORRECTION

| | | |
|---|---|---|
| PATENT NO. | : 8,053,558 B2 | Page 1 of 1 |
| APPLICATION NO. | : 11/931653 | |
| DATED | : November 8, 2011 | |
| INVENTOR(S) | : Drew M. Pardoll et al. | |

It is certified that error appears in the above-identified patent and that said Letters Patent is hereby corrected as shown below:

Claim 12, column 70, line 44, replace "137-DC" with --B7-DC--.

Signed and Sealed this
Twenty-ninth Day of May, 2012

David J. Kappos
*Director of the United States Patent and Trademark Office*